US008481487B2

(12) United States Patent
Blanche et al.

(10) Patent No.: US 8,481,487 B2
(45) Date of Patent: Jul. 9, 2013

(54) MODIFIED SOLUBLE FGF RECEPTOR FC FUSIONS METHOD

(75) Inventors: Francis Blanche, Paris (FR); Béatrice Cameron, Paris (FR); Sylvie Sordello, Paris (FR); Céline Nicolazzi, Paris (FR); Marc Trombe, Paris (FR); Mark Nesbit, Paris (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 13/348,297

(22) Filed: Jan. 11, 2012

(65) Prior Publication Data

US 2012/0195851 A1 Aug. 2, 2012

Related U.S. Application Data

(62) Division of application No. 12/515,463, filed as application No. PCT/IB2007/004354 on Nov. 28, 2007, now Pat. No. 8,119,770.

(30) Foreign Application Priority Data

Nov. 28, 2006 (EP) ..................................... 06291824
Jan. 11, 2007 (EP) ..................................... 07290042

(51) Int. Cl.
*A61K 38/18* (2006.01)
(52) U.S. Cl.
USPC ............. 514/9.1; 514/7.6; 530/395; 530/397; 530/399
(58) Field of Classification Search
None
See application file for complete search history.

(56) References Cited

U.S. PATENT DOCUMENTS

| | | | |
|---|---|---|---|
| 5,116,964 A | 5/1992 | Capon et al. | |
| 5,288,856 A | 2/1994 | Amiguet | |
| 5,349,053 A | 9/1994 | Landolfi | |
| 5,707,632 A | 1/1998 | Williams et al. | |
| 5,726,044 A | 3/1998 | Lo et al. | |
| 5,750,375 A | 5/1998 | Sledziewski et al. | |
| 5,772,997 A | 6/1998 | Hudziak et al. | |
| 6,656,728 B1 | 12/2003 | Kavanaugh et al. | |
| 2002/0045207 A1 | 4/2002 | Krummen et al. | |

FOREIGN PATENT DOCUMENTS

| | | |
|---|---|---|
| EP | 0529076 | 11/1991 |
| EP | 1331266 A1 | 7/2003 |
| EP | 1498490 A1 | 1/2005 |
| EP | 1498491 A1 | 1/2005 |
| EP | 1676910 A1 | 7/2006 |
| EP | 1792987 A1 | 6/2007 |
| WO | 91/00916 | 1/1991 |
| WO | 91/01753 | 2/1991 |
| WO | 92/00999 | 1/1992 |
| WO | 99/54342 | 10/1999 |
| WO | 00/46380 | 6/2000 |
| WO | 03/074679 A2 | 9/2003 |
| WO | 2004/029207 A2 | 4/2004 |
| WO | 2004/099249 A2 | 11/2004 |
| WO | 2005/113295 A1 | 1/2005 |
| WO | 2005/016966 A2 | 12/2005 |
| WO | 2006/019447 A1 | 2/2006 |
| WO | 2006/047350 A2 | 5/2006 |
| WO | 2006/105338 A2 | 10/2006 |
| WO | 2006/113277 A2 | 10/2006 |
| WO | 2007-014123 A2 | 2/2007 |
| WO | 2007/041635 A2 | 4/2007 |

OTHER PUBLICATIONS

Aigner et al., Ribozyme-targeting of a secreted EGF-binding protein (FGF-BP) inhibits proliferation of prostate cancer cells in vitro and in vivo, Oncogene, vol. 21, 2002, pp. 5733-5742.
Anderson et al., Apert syndrome mutations in fibroblast growth factor receptor 2 exhibit increased affinity for FGF ligand, Human Molecular Genetics, vol. 7, No. 9, Sep. 1998, pp. 1475-1483.
Anderson et al., The effect of cell-culture conditions on the oligosaccharide structures of secreted glycoproteins, Current Opinion in Biotechnology, vol. 5, 1994, pp. 546-549.
Anumula et al., High resolution and high sensitivity methods for oligosaccharide mapping and characterization by normal phase high performance liquid chromatography following derivatization with highly fluorescent anthranilic acid, Glycobiology, vol. 8, 1998, pp. 685-694.
Ashkenazi et al., Immunoadhesins as research tools and therapeutic agents, Current Opinion in Immunology. vol. 9, 1997, pp. 195-200.
Bieker et al., Overexpression of Basic Fibroblast Growth Factor and Autocrine Stimulation Acute Myeloid Leukemia, Cancer Research, vol. 63, 2003, pp. 7241-7246.
Birch et al., Antibody production, Advanced Drug Delivery Review, vol. 58. 2006, pp. 671-685.
Borys et al., Culture pH Affects Expression Rates and Glycosylation of Recombinant Mouse Placental Lactogen Proteins by Chinese Hamster Ovary (CHO) Cells, Bio/Technology, vol. 11, Jun. 1993, pp. 720-724.
Brattstrom et al., Basic fibroblast growth factor and vascular endothelial growth factor in sera from non-small cell lung cancer patients, Anticancer Research, vol. 18, Mar. 1998, pp. 1123-1127.
Capon et al., Designing CD4 immunoadhesins for AIDS therapy, Nature, vol. 337, Feb. 1989, pp. 525-531.
Chamow et al., Immunoadhesins: principles and applications, Trends in Biotechnology, vol. 14, 1996, pp. 52-60.
Chitlaru et al., Modulation of circulatory residence of recombinant acetylcholinesterase through biochemical or genetic manipulation of sialyation levels, Biochem. J. 1998, vol. 335, pp. 647-658.

(Continued)

*Primary Examiner* — Michael Pak
(74) *Attorney, Agent, or Firm* — Lathrop & Gage LLP; James H. Velema

(57) ABSTRACT

The invention relates to modified soluble FGF receptor Fc fusions comprising a fusion of a soluble fragment or domain of the FGF receptor part (targeting or binding moiety) with an Fc region of an immunoglobulin part (effector function moiety), having improved biological activity including ADCC/CDC activities, compositions containing them, and method of producing such modified soluble FGF receptor Fc fusion molecules.

26 Claims, 23 Drawing Sheets

OTHER PUBLICATIONS

Cockett et al., High level expression of tissue inhibitor of metalloproteinases in Chinese hamster ovary cells using glutamine synthetase gene amplification, Bio/Technology, vol. 8, No. 7, Jul. 1990, pp. 662-668.

Crouse et al., Expression and Amplification of Engineered Mouse Dihydrofoiate Reductase Minigenes, Molecular & Cellular Biology, vol. 3, No. 2, Feb. 1983, pp. 257-266.

Curling et al., Recombinant human interferon-y, Biochem. J. 1990, vol. 272, pp. 333-337.

Duchesne et al., N-Glycosylation of Fibroblast Growth Factor Receptor 1 Regulates Ligand and Heparan Sulfate Co-receptor Binding, Journal Biological Chemistry (2006), 281(37):27178-27189.

Ferrara et al., Modulation of therapeutic antibody effector functions by glycosylation engineering: Influence of Goigi enzyme localization domain and co-expression of heterologous Beta 1, 4-N-acetylglucosaminyltransferase III and Goigi-alpha mannosidase II, Biotechnology & Bioengineering, vol. 93, No. 5, Jan. 2006, pp. 851086.

Ferrara et al., The Carbohydrate at FcγRIIIa Asn-162, Journal of Biological Chemistry, vol. 281, No. 8, Feb. 2006, pp. 5032-5036.

Foecking et al., Powerful and versatile enhancer-promoter unit for mammalian expression vectors, Gene., vol. 45, 1986, pp. 101-105.

Folkman J., Angiogenesis in cancer, vascular, rheumatoid and other diseases, Nature Medicine, vol. 1, No. 1, 1995, pp. 27-31.

Gamsjaeger et al., Membrane binding of Beta2-glycoprotein I can be described by a two-state reaction model: an atomic force microscopy and surface plasmon resonance study, Biochem. J., vol. 389, Apr. 2005, pp. 665-673.

Gan et al., Expression of Basic Fibroblast Growth Factor Correlates with Resistance to Paclitaxel in Human Patient Tumors, Pharmaceutical Research, vol. 23, No. 6, Jun. 2006, pp. 1324-1331.

Gebert et al., Expression of FSH in CHO cells. II. Stimulation of hFSH expression levels by defined medium supplements, Cytotechnology, vol. 17, 1995, pp. 13-19.

Gillies et al., Antigen binding and biological activities of engineered mutant chimeric antibodies with human tumor specificities, Human Antibodies and Hydridomas, vol. 1, No. 1, 1990, pp. 47-54.

Goochee et al., The Oligosaccharides of Glycoproteins: Bioprocess Factors Affecting Oligosaccharide Structure and their Effect on Glycoprotein Properties, BioTechnology, vol. 9, Dec. 1991, pp. 1347-1355.

Grose et al., Fibroblast growth factor signaling in tumorigenesis, Cytokine & Growth Factor Reviews, vol. 16, 2005, pp. 179-186.

Halaban, Growth Factors and Melanomas, Seminars in Oncology, vol. 23, 1996, pp. 673-681.

Hanada et al., Identification of Fibroblast Growth Factor-5 as an Overexpressed Antigen in Multiple Human Adenocarcinomas, Cancer Research, vol. 61, 2001, pp. 5511-5516.

Hanahan et al., Patterns and Emerging Mechanisms of the Angiogenic Switch during Tumorigenesis, Cell, vol. 86, 1996, pp. 353-364.

Harris, Monoclonal antibodies as therapeutic agents for cancer, Lancet Oncology, vol. 5, 2004, pp. 292-302.

Hayter et al., Glucose-Limited Chemostat Culture of Chinese Hamster Ovary Cells Producing Recombinant Human Interferon-y, Biotechnology & Bioengineering, vol. 39, 1992, pp. 327-335.

Huck et al., Sequence of human immunoglobulin gamma 3 heavy chain constant region gene: comparison with other human C-y genes, Nucleic Acids Research, vol. 14, No. 4, 1986, pp. 1779-1789.

Ibrahimi et al., Analysis of Mutations in Fibroblast Growth Factor (FGF) and a Pathogenic Mutation in FGF Receptor (FGFR) Provides Direct Evidence for the Symmetric Tow-End Model for FGFR Dimerization, Molecular & Cellular Biology, vol. 25, No. 2, Jan. 2005, pp. 671-684.

Ji et al., Characterization of kringle domains of angiostatin as antagonists of endothelial cell migration, an important process in angiogenesis, FASEB J, vol. 12, 1998, pp. 1731-1738.

Jones et al., Controlling N-linked glycan site occupancy, Biochimica et Biophysica Acta., vol. 1726, 2005, pp. 121-137.

Kiefer et al., Molecular Cloning of a Human Basic Fibroblast Growth Factor Receptor cDNA and Expression of a Biologically Active Extracellular Domain in Baculovirus System, Growth Factors, vol. 5, 1991, pp. 115-127.

Krejci et al., FGF-2 abnormalities in B cell chronic lymphocytic and chronic myeloid leukemias, Leukemia, vol. 15, 2001, pp. 228-237.

Kunkel, T., Rapid and efficient site-specific mutagenesis without phenotypic selection, PNAS, vol. 82, Jan. 1985, pp. 488-492.

Kwabi-Addo et al., The role of fibroblast growth factors and their receptors in prostate cancer, Endocrine-Related Cancer, vol. 11, 2004, pp. 709-724.

Lara et al., Comparison of Two Immunomagnetic Separation Technologies to Deplete T Cells From Human Blood Samples, Biotechnology & Bioengineering, vol. 94, No. 1, May 2006, pp. 66-80.

Lazar et al., Engineered antibody Fc variants with enhanced effector function, PNAS, vol. 103, No. 11, Mar. 2006, pp. 4005-4010.

Lowy et al., Isolation of Transforming DNA: Cloning the Hamster aprt Gene, Cell, vol. 22, Dec. 1980, pp. 817-823.

Mulligan et al., Selection for animal ceis that express the *Escherichia coli* gene coding for xanthine-guanine phosphoribosyltransferase, PNAS, vol. 78, Apr. 1981, pp. 2072-2076.

Okazaki et al., Fucose Depletion from Human IgG1 Oligosaccharide Enhances Binding Enthalpy and Association Rate Between IgG1 and RcγRIIIa, J. Mol. Biol., vol. 338, 2004, pp. 1239-1249.

Pellegrini et al., Crystal Structure of Fibroblast Growth Factor Receptor Ectodomain Bound to Ligand and Heparin, Nature, vol. 407, Oct. 2000, pp. 1029-1034.

Powell et al., Fibroblast Growth Factor Receptors 1 and 2 Interact Differently with Heparin/Heparin Sulfate, Implications of dynamic assembly of a ternary signaling complex, J. of Biol. Chem., vol. 277, No. 32, Aug. 9, 2002, pp. 28554-28563.

Presta et al., Fibroblast growth factor/fibroblast growth factor receptor system in angiogenesis, Cytokine & Growth Factor Reviews, vol. 16, 2005, pp. 159-178.

Ripka et al., Two Chinese Hamster Ovary Glycosylation Mutants Affected in the Conversion of GDP-Mannose to GDP-Fucose, Archives of Biochem. & Biophys., vol. 249, Sep. 1986, pp. 533-545.

Saddic et al., Carbohydrate Composition Analysis of Glycoproteins Using Highly Sensitive Fluorescence Detection Methods, Methods in Molecular Biology, vol. 194, Apr. 2002, pp. 23-36.

Santerre et al., Expression of Prokaryotic Genes for Hygromycin B and G418 Resistance as Dominant-Selection Markers in Mouse L Cells, Gene, vol. 30, 1984, pp. 147-156.

Sharkey et al., Targeted Therapy of Cancer: New Prospects for Antibodies and Immunoconjugates, CA Cancer Journal Clinicians, 2006, vol. 56, pp. 225-243.

Shields et al., High Resolution Mapping of the Binding Site on Human igG1 for FcγRI, FcγRII, FcγRIII, and FcRn and Design of IgG1 Variants with Improved Binding to the FcγR, J. of Biol. Chem., vol. 276, No. 9, Mar. 2001, pp. 6591-6604.

Shinkawa et al., The Absence of Fucose but Not the Presence of Galactose or Bisecting N-Acetylglucosamine of Human IgG1 Complex-Type Oligosaccharides Shows the Critical Role of Enhancing Antibody-dependent Cellular Cytotoxicity, Journal of Biological Chemistry, vol. 278, No. 5, Jan. 2003, pp. 3466-3473.

Strome et al., A Mechanistic Perspective of Monoclonal Antibodies in Cancer Therapy Beyond Target-Related Effects, The Oncologist, vol. 12, 2007, pp. 1084-1095.

Surfluh et al., Auxin-induced changes in the patterns of protein synthesis in soybean hypocotyl, PNAS, vol. 77, Jan. 1980, pp. 357-361.

Szybalska et al., Genetics of Human Cell Lines, IV, DNA-Mediated Heritable Transformation of Biochemical Trait, PNAS, vol. 48, Dec. 1962, pp. 2026-2034.

Takanami et al., Expression of PDGF, IGF-II, bFGF and TGF-beta 1 in Pulmonary Adenocarcinoma, Pathology—Research & Practice, vol. 192, Iss. 11, Nov. 1996, pp. 1113-1120.

Tassi et al., Expression of a Fibroblast Growth Factor-Binding Protein during the Development of Adenocarcinoma of the Pancreas and Colon, Cancer Research, vol. 66, 2006, pp. 1191-1198.

Trueb et al., Characterization of FGFRL1, a Novel Fibroblast Growth Factor (FGF) Receptor Preferentially Expressed in Skeletal Tissues, Journal of Biological Chemistry, vol. 278, No. 36, Sep. 5, 2003, pp. 33857-33865.

Umana et al., Engineered glycoforms of an antineuroblastoma IgG1 with optimized antibody-dependent cellular cytotoxic activity, Nature Biotechnology, vol. 17, Feb. 1999, pp. 176-180.

Volm et al., Angiogenic Growth Factors and their Receptors in Non-Small Cell Lung Carcinomas and their Relationships to Drug Response in Vitro, Anticancer Research, vol. 17, Jan. 1997, pp. 99-103.

Von Heijne, G., A new method for predicting signal sequence cleavage sites, Nucleic Acids Research, vol. 14, No. 11, 1986, pp. 4683-4690.

Walsh et al., Post-translational modifications in the context of therapeutic proteins, Nature Biotechnology, vol. 24, 2006, pp. 1241-1252.

Webster et al., Evaluation of the role of the asialoglycoprotein receptor in the clearance of UK-279,276 (recombinant neutrophil inhibitory factor), Xenobiolica, vol. 33, Sep. 2003, pp. 945-956.

Whitworth et al., Regulation of Fibroblast Growth Factor-2 Activity by Human Ovarian Cancer Tumor Endothelium, Clinical Cancer Research, vol. 11, No. 12, Jun. 2005, pp. 4282-4288.

Wigler et al., Transfer of Purified Herpes virus Thymidine Kinase Gene to Cultured Mouse Cells, Cell, vol. 11, 1977, pp. 223-232.

Wu et al., Delivery systems for gene therapy, Biotherapy, vol. 3, 1991, pp. 87-95.

Yang et al., Effects of Ammonia on CHO Cell Growth, Erythropoietin Production, and Glycosylation, Biotechnology & Bioengineering, vol. 68, 2000, pp. 370-380.

Brooks, Protein Glycosylation in Diverse Cell Systems: Implications for Modification and Analysis of Recombinant Proteins, Expert Review of Proteomics (2006), 3(3):345-359.

Butler, Animal Cell Cultures: Recent Achievements and Perspectives in the Production of Biopharmaceuticals, Applied Microbiology and Biotechnology (2005), 68(3):283-291.

Declaration of Dr. Shawn Russell concerning inherent N-glycosylation site occupancy of FGFR1-IIIc-Fc of WO2007/014123 when expressed in CHO cells.

Kasturi et al., The Hydroxy Amino Acid in an Asn-X-Ser/Thr Sequon Can Influence N-Linked Core Glycosylation Efficiency and the Level of Expression of a Cell Surface Glycoprotein, Journal of Biological Chemistry (1995), 270 (24):14756-14761.

Sola et al., Effects of Glycosylation on the Stability of Protein Pharmaceuticals, Journal of Pharmaceutical Sciences (2009), 98(4):1223-1245.

Shriver et al., Glycomics: A Pathway to a Class of New and Improved Therapeutics, Nature Reviews: Drug Discovery (2004), 3:863-873.

Weikert et al., Engineering Chinese Hamster Ovary Cells to Maximize Sialic Acid Content of Recombinant Glycoproteins, Nature Biotechnology (1999),17:1116-21.

Fig. 2A

```
1281                     ATGAGG CTTCGGGAGC CGCTCCTGAG CGGCAGCGCC GCGATGCCAG GGCGTCCCT ACAGCGGGCC
        TACTCC GAAGCCCTCG CGAGGACTC GCCGTCGCGG GCGCGGGTC CGGCAGGGA TGTCGCCCGG
1361 TGCCGCCTGC TCGTGGCCGT CTGCCGCTCTG CACCTTGGCG TCACCCTCGT TACTACCTG GCTGGCGCG ACCTGAGCCG
     ACGGCCGACG AGCACCGGCA GACGGCAGAC GTGGAACCGC AGTGGGAGCA AATGATGGAC CGACGGGCGC TGGATCGGC
1441 CCTGCCCAA CTGGTCGGAG TCTCCACACC GCTGCAGGGC CGACGTTGT CACGGCGCG CATCGGGCAG TCCTCCGGGG
     GGACGGGGTT GACCAGCCTC AGAGGTGTGG CGGCCGCCGC CTCTCTAGG CGCTCCTCC CAGCCGCGCC GTAGCCCGTC AGGAGGCCCC
1521 AGCTCCGGAC CGGAGGGGCC CGGCCCGCCG CGGCGCTAGC GAGGAGATCC GCGGAGGAG GTCGGCGCGG GCCCACCGCT CTCCAGCCCA
     TCGAGGCCTG GCCTCCCCGG CCCGGCTAGC AACTTGACCT CGGTCCCAGT GCCCCACACC ACCGCACTGT GAGGTCGGGT
1601 GTCGTGGATT CTGGCCCTGG CTGGCCCGCC GGGCGATCG TGAACTGGA GCCAGGGTCA CGGGGTGTCG TGGCGTGACA GCCACGCGG
     CAGCACCTAA GAGCGGGACG TGCTTGTGGC ACGAACACCC GGGGTACGAC TAACTCAAAT TGTACGGACA CCTGACCTC GAGCACCGTT
1681 CTGCCCTGAG GAGTCCGGC CTCAGGGGCG ATGGCGGGCC GCTATGGGCGG GCTATCGCCC CAGGGACTGC GTCTCCTC ACAAGGTGGC CATCATCATT
     GACGGGACTC CTCAGGGCGC AATGTGAAG GTGCCGGCGC TACCCGCGGCC GATAGGGGGG GCTACGGGG CAGAGAGGAG TGTCCACGGG GTAGTAGTAA
1761 AGCAGAACCC AAATGAAG TTTACACTTC CCTACCGCGG CGACCTGAG TACCTGGGTAT AATCCGATA TACTGGCTAT ATTATTGCA YCCAGTCCTG CAGCGCCAGC AGCTGGACTA
     TCGTCTTGGG TTACACTTTC CCATTCCGCA ACCGGCAGGA GCACCTCAG CGTGGAGTTC ATGACCGATA CACTATATTC AATCGTGCTA AGCTCCTCAA TGTGCTTT CAAGAAGCCT
1841 CCATTCCGCA ACCGGCAGGA GCACCTCAG CGTGGAGTTC CGTGAGTTC ATGACCGATA CACTATATTC AATCGTGCTA AGCTCCTCAA TGTGCTTT CAAGAAGCCT
     GGTAAGGCGT TGGCGTCT GTTATCAACC AGGGCGGGGA TGCTTTGTGT TTAGTGACGT CGAATGAATG ACCATAATGC GTACAGGTGT
1921 TGGCATCTAT GTTATCAACC AGGGCGGGGA TGCTTTGTGT TTAGTGACGT TCGAGGAGTT ACAACCGAAA GTTCTTCGA
     ACCGTAGATA CAATAGTTGG TCGCCCCTCT GTGATATAAG AGCAACACCA CCTGGAGTAA GGTACCTAC TGGTATTACG CATGTCACA
2001 TGAAGGACTA TGACTACACC ACTGATGTGG AGAACACCA AATCACTGCA CCTGAGAAT TTGGATTCAG CCTACCTAT GTTCAGTATT TTGGAGTGT
     ACTTCCTGAT ACTGATGTGG AGGAACACA TTCCGTTGCA ATGGATCAAGT TACCTATCA AACCTAAGT GGATGGAATA CAAGTCATAA AACCTCCACA
2081 TTTTCACAGC CACGGCACAT TTCCGTTGCA AGGCAAGT AGTTTCTAAC CATCAATGGGA GTAGTTACCT AAAGGATTAT TAATAACCCC GAAGATAGT
     AAAAGTGTCG GTGCCGTGTA AGTAAACAC AGTTTCTAAC CATCAATGGGA TGTCTATATC ACAGATATAG CTGTGGTCG GGAGGTGTG CATGATCCGC
2161 CTCTGCTCTA AGTAAACAC TCATTGTTG TCAAGATTGG GTAGTTACCT ACAGATATAG AGCGGGTTTA TGACCGAAT TCCACCAGC CCTCCACAGC GTACTAGGCG
     GAGACGAGAT TCATTGTTG TCAAGATTGG TTTAGAGGCA AAATCCCGT ACTTGGGTTA GGACTCTCCA AACTGGCTTA ACGTGTGT TTCCTCTGT ACGAGAGACT
2241 TGTAAAAATT GTCTAATCAA ACAAGAAAAA TGAACCGAAT CCTCAGAGGT GGAATGCTGCT GGATACCCAT TGTATACCCA AATCACAGTG GACATCGGGA
     CACTCAAGAG ACAAGAAAAA TGAACCGAAT CCTCAGAGGT TGAACCGAAT GGATACCCAT TGTATACCCA AATCACAGTG GACATCGGGA
2321 GTGAGTCTC TGTTCTTTT ACTTGGGTTA GGACTCTCCA AACTGGCTTA ACGTGTGT TTCCTCTGT ACGAGAGACT
     TGGTTTGAAC TCACTCACCT ACCAGGTGCT GGATGCACA AGATACCCAT TGTATACCCA AATCACAGTG GACATCGGGA
2401 ACCAAACTTG AGTAGTGGA TGGTCCACGA CCTACACGTC TCTATGGGTA ACATATGGGT TTAGTGTCAC CTGTAGCCCT
     CACCCAGCTA G
2481 GTGGCTCGAT C
```

Fig. 2B

```
  1 MRLREPLLSG SAAMPGASLQ RACRLLVAVC ALHLGVTLVY YLAGRDLSRL
 51 PQLVGVSTPL QGGSNSAAAI GQSSGELRTG GARPPPLGA SSQPRPGGDS
101 SPVVDSGPGP ASNLTSVPVP HTTALSLPAC PEESPLLVGP MLIEFNMPVD
151 LELVAKQNPN VKMGGRYAPR DCVSPHKVAI IIPFRNRQEH LKYWLYYLHP
201 VLQRQQLDYG IYVINQAGDT IFNRAKLLNV GFQEALKDYD YTCFVFSDVD
251 LIPMNDHNAY RCFSQPRHIS VAMDKFGFSL PVVQYFGGVS ALSKQQFLTI
301 NGFPNNYWGW GGEDDDIFNR LVFRGMSISR PNAVVGRCRM IRHSRDKKNE
351 PNPQRFDRIA HTKETMLSDG LNSLTYQVLD VQRYPLYTQI TVDIGTPS
```

Fig. 3A

```
1281                  ATGGGA CTCTTGGTAT TTGTGCGCAA TCTGCTGCTA GCCCTCTGCC TCTTTCTCGT ACTGGGATTT
       TACCCT GAGAACCATA AACACGGGTT AGAGACGAT CGGGAGACGG CAATTCAGTG AGAAAGACCA TGACCCTAAA
1361   TTGTATTATT CTGCGTGGAA GCTACACTTA CTCCAGTGGG AGGAGGACTC TCCTCCTGAG GTTAAGTCAC GTTCTTTCCT TTGACTCCGC
       AACATAATAA GACCGACCTT CGATGTGAAT AGTATGATCG GTTGGGCTTC CTCTCGAAAT TGGACTCTAA ACTGCCTGCT CAAGAAAGGA AACTGAGGCG
1441   TGGACAAACA CTAGCCTCAG AGTATGATCG TCATACTAGC GCAAGCCTGG CAACCGGAAG ACCTGAGATT TGACGGACGA CTTAATCGGT
       ACCTGTTTGT GATCCGAGTC TCATACTAGC GAGGGAGCTT GCAAGCCTGG CGTTCGGACG GATACGAAGT CGGAACTACT GCCGGTAGAA GGGGCCAAG
1521   CCAAGTACGC AAACTTTTCA CTCCCTCGAA CGTTCGGACG GATACGAAGT CGGAACTACT GCCGGTAGAA CGGCATCTT CCCCCGGTTC
       GGTTCATGCG TTTGAAAAGT CCTGGATGAC TCCTTTCGCA AGTGGCTAG TCACCCGATC TTAGGCCCTC AAGCACGGCG GAAAACCCTA
1601   TCCAAGCCAG CACCCATGGT CCTGGATGAC TCCTTTCGCA AGTGGCTAG TCACCCGATC TTAGGCCCTC AAGCACGGCG GAAAACCCTA
       AGGTTCGGTC GTGGGTACAA GGACCTACTG AGGAAAGCGT TCAGCCGATC CTGTGAGTG TGCAACAAG TCTCTGGGGT CACGAATTGA CGACTATGAC
1681   CAAAGGTCAA GACAATCGA TCAAAGCCAT CTTGTCAGTC GAACAGCTCAG TGGTTCTCA TGCCAACAAG TCTCTGGGGT CACGAATTGA CGACTATGAC
       GTTTCCAGTT CTGTTAGACT AGTTTCGGTA GAACAGCTCAG GAGGCGCTCT TGCCAACAAG TCTCTGGGGT CACGAATTGA CGACTATGAC
1761   GCTGCGCGCG CTGCATCATC GTGGCAACAG GAGGCGCTCT CTCCGCAGAG ACGGTTGTTC AGAGACCCGA GTGCTTAACT GCTGATACTG
       CGACGGCGGC GACGTAGTAG CACCCGTTAC GAGGGCGCTCT TTTCCGAAAC TCTTCCTGCA CCGTCGTTT TGCTGTGACG CGTAGTGGAT
1841   ATTGCTGGCTGA GACTGAATTC AGCACCAGTG TCGTGGTCAC GGCCTGAGCA GTACGAGCGC GATTCTCTCT TTGTCCTCGC CGGCTTCAAG TGGCAGGACT
       TAACACCACT CTGACTTAAG TCGTGGTCAC GGCCTGAGCA GTACGAGCGC GATTCTCTCT TTGTCCTCGC CGGCTTCAAG TGGCAGGACT
1921   CCCCGAGGGC GCCATCCAGC CGGACGCGGT GTCTACAAGG AGAGACTGGAT TGCATCCACTC ACGTAGCCTA AACACAGGAGCG GCCGAAGTTC ACCGTCCTGA
       GGGCCTCCCG CGGTAGTCGC GAAATACATC CAGAGTTCC TCGAATCCTC AACCCATATT TCATCCAGGA GGCCGCCCTTC ACCCTCATGG GCCTGCCCTT
2001   TTAAGTGTTT GAAATACATC CAGAGTTCC TCGAATCCTC AACCCATATT TCATCCAGGA GGCCGCCCTTC ACCCTCATGG GCCTGCCCTT
       AATTCACCAA CTTTATGTAG CCCCTGAGAT TCGAATCCTC AGCTTAGGAG TTGGGTATAA AGTAGGTCCT GGCAGTGTGG CAGTGACCAT GGCACTACAC CGGACGGGAA
2081   CCCAAGGAGC CCCCTGAGAT TCGAATCCTC AGCTTAGGAG TTGGGTATAA AGTAGGTCCT GGCAGTGTGG CAGTGACCAT GGCACTACAC CGGACGGGAA
       GGGTTCCTCG GGGGACTCTA AGCTTAGGAG TTGGGTATAA AGTAGGTCCT GGCAGTGTGG CAGTGACCAT GGCACTACAC CGGACGGGAA
2161   CAACAATGGC CTCATGGGCC GGGGAACAT CCCTACCCTT GGGATGGGAA TGAGCACACC CAACCCACCC GTCACTGGTA CCGTGATGTG CCGACACTGC
       GTTGTTACCG GAGTACCCGG CCCCCTTGTA GCTATGACA CGATACTGT CAGCGAGAGA AAGAGTTTCT GGGAAGCTG GTGAAAGCTC GGTCATCAC
2241   AGGTGGCAGT CGCAGGATTT GCTATGACA CGATACTGT CAGCGAGAGA AAGAGTTTCT GGGAAGCTG GTGAAAGCTC GGTCATCAC
       TCCACCGTCA GCGTCCTAAA AGTCCTGGAC GCACAATATC CAGCGAGAGA AAGAGTTTCT GGGAAGCTG GTGAAAGCTC GGTCATCAC
2321   GCCATCAAAG AGTCCTGGAC GCACAATATC CAGCGAGAGA AAGAGTTTCT GGGAAGCTG GTGAAAGCTC GGTCATCAC
       CGGTAGTTTC TCAGGACCTG CGTGTTATAG GTCGCTCTCT TTCTCAAAGA CGCCTTCGAC CACTTTCGAG CGCAGTAGTG
2401   TGATCTAAGC AGTGGCATCT GA
       ACTAGATTCG TCACCGTAGA CT
```

Fig. 3B

```
  1   MGLLVFVRNL LLALCLFLVL GFLYYSAWKL HLLQWEEDSN SVVLSFDSAG
 51   QTLGSEYDRL GFLLNLDSKL PAELATKYAN FSEGACKPGY ASALMTAIFP
101   RFSKPAPMFL DDSFRKWARI REFVPPFGIK GQDNLIKAIL SVTKEYRLTP
151   ALDSLRCRRC IIVGNGGVLA NKSLGSRIDD YDIVVRLNSA PVKGFEKDVG
201   SKTTLRITYP EGAMQRPEQY ERDSLEVLAG FKWQDFKWLK YIVYKERVSA
251   SDGFWKSVAT RVPKEPPEIR ILNPYFIQEA AFFLIGLPFN NGLMGRGNIP
301   TLGSVAVTMA LHGCDEVAVA GFGYDMSTPN APLHYETVR MAAIKESWTH
351   NIQREKEFLR KLVKARVITD LSSGI
```

Fig. 4A

```
                   ACGTACA GGATGCAACT CCTGCCTTGC ATTGCACTAA GTCTTGCACT
                   TACATGT CCTACGTTGA GGACAGACG TAACGTGATT CAGAACGTGA
6241 TGTCACGAAT TCATTAGTTG AGGATACCAC ATTAGAGCCA GAAGAGCCAC CAACTAAATA CCAAATCTCT CAACCAGAAG
6321 ACAGTGCTTA AGTATCAAC TCCTATGCTG TAATCTCGGT CTTCTCGGTG GTTGATTTAT GGTTTAGAGA GTTGGTCTTC
6401 TGTACGTGGC TGCACCAGGG GAGTCGCTAG AGGTGCGCTG CCTGTTGAAA GATGCCGCCG TGATCAGTTG GACTAAGGAT
6481 ACATGCACCT ACGTGGTCCC CTCCACGGATC TCCACGCCAC GGACAACTTT CTACGGCGGC ACTAGTCAAC CTGATTCCTA
6561 GGGGTGCACT TGGGGCCCAA CAATAGGACA GTGCTTATTG GGGAGTACTT CCCTCATGAA CGTCTATTTC CGCGGGTGCG CTAGAGACTC
6641 CCCCACGTGA ACCCCGGGTT GTTATCCTGT CACGAATAAC TGTAGACAGT GAAACTTGTT ACTTCATGGT GAATGTCACA GATGCCATCT
6721 CGGCTTCTAT GCTTGTACTG CCAGTAGGAC ACATCCTG ACATCTGTCA CTTTGAACCA TGAAGTACCA CTTACAGTGT CTACGGTAGA
6801 GCCGGAGATA TGATGAGGAT GACACCGATG GGTCATCCTG GCGGGAAGA TTTTGTCAGT GAGAACAGTA ACAACAAGAG AGCACCATAC
6881 CATCCGGACA ACTACTCCTA CTGTGGCTAC CACGCCTTCT AAAACAGTCA CTCTTGTCAT TGTTGTTCTC TCGTGGTATG
6961 GTAGGCCTCT CAGAAAAGAT GGAAAAGCGG CTCCATGCTG TGCCTGCGGC CAACACTGTC CAACACTGTC AAGTTTCGCT GCCCAGCCGG
7041 TGGACCAACA GTCTTTTCTA CCTTTTCGCC GAGGTACGAC ACGGACGCCG GTTCTGACAG TTCAAAGCGA CGGGTCGGCC
7121 ACCTGGTTGT ATGCCAACCA TGCGGTGGCT GAAAAACGGG TTCCTCAAAT AGCAGGACCA TCGCATTGGA GGCTACAAGG
7201 CCCCTTGGGT TACGGTTGGT ACGGCACCGA CTTTTTGCCC CCCATCTGAC TCGTCCTCGT AGCGTACCT CCGATGTTCC
7281 TACGAAACCA GGACTGGAGC CTCATTATGG AAAGTGTGT GGGTAGACTG TTCCCTTTAA TATGGACACA GGTGGAGAAT
7361 ATGCTTTGGT CGTGACCTCG GAGTAATACC TTTCACACCA CTGATGTTG TGGAGCGATC GCCTCACCGG CCCATCTCC CCACCTCTTA
7441 GAATACGGGT CCATCAATCA CACGTACCAC GACCTACAAC ACCTCGCTAG CGGAGTGCC GGGTAGGAGG AAGCCGGACT
7521 CTTATGCCCA GGTAGTTAGT GTGCATGGTG GCCGCCAAAT GCCTCCACAG TGGTCGGAGG AGACGTAGAG TTTGTCTGCA AGGTTTACAG TGATGCCCAG TTCGGCCTGA
7601 CGGACCTTTA CGGAGGTGTC ACCAGCCTCC TCTGCATCTC AACAGACGT TCCAAATGTC AACACTCTCC ACTACGGGTC GGGTGTAGG
7681 AGTGGATCAA GCACGTGGAA AAGAACGGCA GTAAATACGG GCCCGACGGG CTGCCCTACC TCAAGGTTCT CAAGCCCGCC
7761 TCAACTAGTT CGTCCACCTT TTCTTGCCGT CATTTATGCC CGGGCTGCCC GACGGATGG AGTTCCAAGA GACGCTGGGG AATATACCTG
7841 GGTGTTAACA CACCGACAGA AGAGATTGAG GTTCTCTATA CAAGAGATAT AAGCCTTACA TTGAAAACTC CTGCGACCCC TTATATGCAC
7921 CCACAATTGT GGTGCCTGTT TCTCTAACTC CAAGAGATAT AAGCCTTACA TGGTTGACAG TTCTCCCAGC CCTGGAAGA GAAAAGAGA
8001 CTTGGCGGGT AATTCTATTG GGATATCCGT TCACTCTGCA AGTGAGACGT ACCAACTGTC AAGACGGTCG CGGACCTTCT CTTTTCCTCT
8081 GAACCGCCCA TTAAGATAAC CCTATAGGAA CTGTCAGCGC TAGAGCCCAA ATCTTGTGAC AAAACTCACA CATGCCCACC GTGCCCAGCA
     TTAAGCTTC CCCAGACTAC CTGTCAGCGC GACACGTCGG ATCTCGGGTT TAGACACTG TTTTGAGTGT GTACGGGTGG CACGGTCGT
     AATGTCGAAG GGGTCTGATG GACAGTTCTC CTCTTCCCCC CAAAACCCGA GGACACCCTC ATGATCTCCC GGACCCCTGA
     CCTGAACTCC TGGGGGGACC GTCAGTCTTC CTCTTCCCCC GAGAAGGGGG GTTTTGGGTT CCTGTGGGAG TACTAGGGG CCTGGGACT
     GGACTTGAGG ACCCCCCTGG CAGTCAGAAG GAGAAGGGGG GTTTTGGGTT CCTGTGGGAG TACTAGGGG CCTGGGACT
     GGTCACATGC GTGGTGGTGG ACGTGAGCCA CGAAGACCCA GAGGTCAAGT TCAACTGGTA CGTGGACGGC GTGGAGGTGC
     CCAGTGTACG CACCACCACC TGCACCACC CGGGAGGAGC AGTACAACAG CACGTACCGT GTGGTCAGCG TCTTCACCGT CCTCCACCAG
     ATAATGCCAA GACAAAGCCG CGGGAGGAGC AGTACAACAG CACGTACCGT GTGGTCAGCG AGGAGTGGCA GGACGTGGTC
     TATTACGGTT CTGTTTCGGC AAGATAGGGT CGCTGTAGCG CGCCTCGTTC TCCTCTACAC CAAAGCCCC ATCAGAAAA CCATCCTCAA
     GACTGCCTCA ATGCAAGGA GTACAAGGA CGACTCCGAC AAGGTCTCCA ACAAAGCCCT CCCAGCCCCC ATCGAGAAAA CCATCTCCAA
     CTGACCGACT TACCCTTCCT CATGTTCACG TTCCAGAGGT TGTTTCGGAG GGGTCGGGGG TAGCTCTTT GGTAGAGGTT
     AGCCAAAGGG CAGGCCCGAG AACCACAGT GTACACCCTG CCCCCATCCC GGGATGAGCT GACCAAGAAC CAGGTCAGCC
     TCGGTTTCCC GTCCGGGCTC TTGGTGTCCA CATGTGGGAC GGGGTAGGG CCCTACTGA CTGGTTCTTG GTCCAGTCGG
     TGACCTGCCT GTCAAAGGC TTCTATCCCA AGATAGGGT CGTGAGTGG GCCACGCAT GGCAGCCGGA GAACAACTAC
     ACTGCGGAGA CCAGTTTCCG AAGATAGGGT CGCTGTAGCG CGCCTCGTTC TCCTCTACAC CAAAGCCCC CAGTCGGTCC
     AAGACCACGC CTCCGTGCT GGACTCCGAC GGCTCCTTCT TCCTCTACAC CAAGCTCACC GTGGACAAGA GCAGGTGGCA
     TTCTGTGTCG GAGGGGCAGA CCTCAGGCTG CCGAGGGAAGA GGAGATGTC GTTGGGGCAC CACCCGTCCT CTGCCACCGT
     CGTCCCCCTG CAGAAGAGTA CGGAGCACTA CGGACTCCGA GACGTGTTGG TGATGTGGCC GTCGACGATG AGGGACAGAG
     CGGGTTGA
     GCCCAACT
```

Fig. 4B

```
  1  LVEDTTLEPE EPPTKYQISQ PEVYVAAPGE SLEVRCLLKD AAVISWTKDG
 51  VHLGPNNRTV LIGEYLQIKG ATPRDSGLYA CTASRTVDSE TWYFMVNVTD
101  AISSGDDEDD TDGAEDFVSE NSNNKRAPYW TNTEKMEKRL HAVPAANTVK
151  FRCPAGGNPM PTMRWLKNGK EFKQEHRIGG YKVRNQHWSL IMESVVPSDK
201  GNYTCVVENE YGSINHTYHL DVVERSPHRP ILQAGLPANA STVVGGDVEF
251  VCKVYSDAQP HIQWIKHVEK NGSKYGPDGL PYLKVLKAAG VNTTDKEIEV
301  LYIRNVTFED AGEYTCLAGN SIGISFHSAW LTVLPAPGRE KEITASPDYL
351  SALEPKSCDK THTCPPCPAP ELLGGPSVFL FPPKPKDTLM ISRTPEVTCV
401  VVDVSHEDPE VKFNWYVDGV EVHNAKTKPR EEQYNSTYRV VSVLTVLHQD
451  WLNGKEYKCK VSNKALPAPI EKTISKAKGQ PREPQVYTLP PSRDELTKNQ
501  VSLTCLVKGF YPSDIAVEWE SNGQPENNYK TTPPVLDSDG SFFLYSKLTV
551  DKSRWQQGNV FSCSVMHEAL HNHYTQKSLS LSPG
```

Fig. 4C

```
  1  LVEDTTLEPE EPPTKYQISQ PEVYVAAPGE SLEVRCLLKD AAVISWTKDG
 51  VHLGPNNRTV LIGEYLQIKG ATPRDSGLYA CTASRTVDSE TWYFMVNVTD
101  AISSGDDEDD TDGAEDFVSE NSNNKRAPYW TNTEKMEKRL HAVPAANTVK
151  FRCPAGGNPM PTMRWLKNGK EFKQEHRIGG YKVRNQHWSL IMESVVPSDK
201  GNYTCVVENE YGSINHTYHL DVVERSPHRP ILQAGLPANA STVVGGDVEF
251  VCKVYSDAQP HIQWIKHVEK NGSKYGPDGL PYLKVLKAAG VNTTDKEIEV
301  LYIRNVTFED AGEYTCLAGN SIGISFHSAW LTVLPAPGRE KEITASPDYL
```

Fig. 4D

```
  1  EPKSCDKTHT CPPCPAPELL GGPSVFLFPP KPKDTLMISR TPEVTCVVVD
 51  VSHEDPEVKF NWYVDGVEVH NAKTKPREEQ YNSTYRVVSV LTVLHQDWLN
101  GKEYKCKVSN KALPAPIEKT ISKAKGQPRE PQVYTLPPSR DELTKNQVSL
151  TCLVKGFYPS DIAVEWESNG QPENNYKTTP PVLDSDGSFF LYSKLTVDKS
201  RWQQGNVFSC SVMHEALHNH YTQKSLSLSP G
```

Fig. 4E

```
  1  SAL
```

Fig. 4F

```
  1  MYRMQLLSCI ALSLALVTNS
```

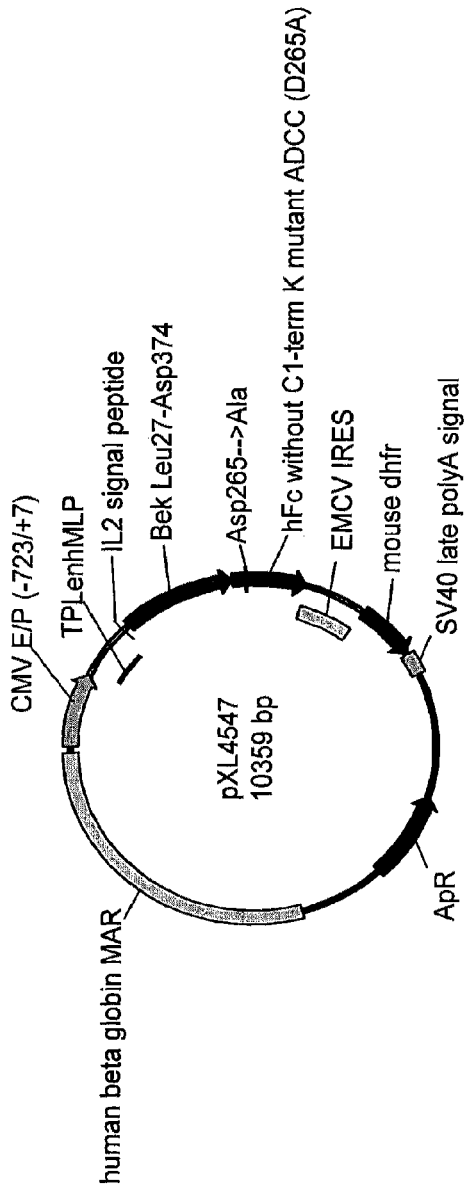

```
  1  LVEDTTLEPE EPPTKYQISQ PEVYVAAPGE SLEVRCLLKD AAVISWTKDG
 51  VHLGPNNRTV LIGEYLQIKG ATPRDSGLYA CTASRTVDSE TWYFMVNVTD
101  AISSGDEDD  TDGAEDFVSE NSNNKRAPYW TNTEKMEKRL HAVPAANTVK
151  FRCPAGGNPM PTMRWLKNGK EFKOEHRIGG YKVRNQHWSL IMESVVPSDK
201  GNYTCVVENE YGSINHTYHL DVERSPHRP  ILQAGLPANA STVVGGDVEF
251  VCKVYSDAQP HIQWIKHVEK NGSKYGPDGL PYLKVLKAAG VNTTDKEIEV
301  LYIRNVTFED AGEYTCLAGN SIGISFHSAW LTVLPAPGRE KEITASFDKT
351  HTCPPCPAPE LLGGPSVFLF PPKPKDTLMI SRTPEVTCVV VAVSHEDPEV
401  KFNWYVDGVE VHNAKTKPRE EQYNSTYRVV SVLTVLHQDW LNGKEYKCKV
451  SNKALPAPIE KTISKAKGQP REPQVYTLPP SRDELTKNQV SLTCLVKGFY
501  PSDIAVEWES NGQPENNYKT TPPVLDSDGS FFLYSKLTVD KSRWQQGNVF
551  SCSVMHEALH NHYTQKSLSL SPG
```

MODIFIED SOLUBLE FGF RECEPTOR FC FUSIONS METHOD

This application is a divisional application of U.S. patent application Ser. No. 12/515,463, filed on May 19, 2009, now U.S. Pat. No. 8,119,770, which is a national stage application of international application number PCT/IB2007/004354, filed Nov. 28, 2007, which claims priority to European patent application no. 06291824.8, filed on Nov. 28, 2006, and to European patent application no. 07290042.6, filed on Jan. 11, 2007.

FIELD OF THE INVENTION AND INTRODUCTION

The invention relates to modified soluble FGF receptor Fc fusions comprising a fusion of a soluble fragment or domain of the FGF receptor with an Fc region of an immunoglobulin, having improved biological activity, compositions containing them, and method of producing such modified soluble FGF receptor Fc fusion molecules. Particularly, the modified soluble FGF receptor Fc fusions have improved anti-angiogenic activity and anti-tumoral antibody-dependent cell mediated cytotoxicity activities, namely ADCC (antibody-dependent cellular cytotoxicity) and/or CDC (complement-dependent cytotoxicity), and are thus useful in the treatment of cancer, metastatic tumors and for reducing tumor growth in a subject. The invention further relates to methods of inhibiting tumor growth and methods for the treatment or prevention of pathological situations including, but not limited to, breast cancer, melanoma, leukemia, brain metastases, renal cancer, primary melanoma, primary colon cancer, primary bladder cancer, infantile hemangioma, ovarian cancer, prostate cancer and lung cancer.

BACKGROUND OF AND RELEVANCE OF THE INVENTION

Angiogenesis, i.e., the formation of new blood vessels from pre-existing ones, involves a complex coordination of endothelial cell proliferation, migration, basement membrane degradation and neovessel organization (Ji et al., 1998, *FASEB J.* 12:1731-1738). The local, uncontrolled release of angiogenic growth factors and/or alterations of the production of natural angiogenic inhibitors, with a consequent alteration of the angiogenic balance (Hanahan et al, 1996, *Cell.* 86: 353-64) are responsible for the uncontrolled endothelial cell proliferation that takes place during tumor neovascularization and in angiogenesis-dependent diseases (Folkman, 1995, *Nat. Med.* 1:27-31).

Numerous natural inducers of angiogenesis have been identified, including members of the vascular endothelial growth factor (VEGF) family, angiopoietins, transforming growth factor-α and -β (TGF-α and -β), platelet-derived growth factors (PDGF), tumor necrosis factor-α (TNF-α), interleukins, chemokines, and the members of the fibroblast growth factor (FGF) family. These potent angiogenic factors are often over-expressed by tumor tissues (Presta, 2005, *Cytokine & Growth Factors Reviews.* 16: 159-178; Grose, 2005, *Cytokine & Growth Factors Reviews.* 16: 179-186).

Indeed, FGFs, and more specially FGF2, are over-expressed in numerous human cancer including melanoma (Halaban, 1996, *Semin Oncol.* 23:673-81; Hanada, 2001, *Cancer Res.* 61: 5511-5516), leukemia (Krejci et al, 2001 *Leukemia.* 15:228-37, Bieker et al, 2003, *Cancer Res.* 63: 7241-7246) renal cancer (Hanada, 2001, *Cancer Res.* 61: 5511-5516), colon cancer (Tassi, 2006, *Cancer Res.* 66:1191-1198), ovarian cancer (Whitworth et al, 2005, *Clin Cancer Res.* 11:4282-4288, Gan et al, 2006, *Pharm Res.* 23:1324-31), prostate cancer (Aigner et al, 2002 *Oncogene*, 21:5733-42; Kwabi-Addo et al, 2004, *Endocr Relat Cancer.* 11:709-24) and lung cancer (Takanami et al, 1996, *Pathol Res Pract.* 192:1113-20; Volm et al, 1997, *Anticancer Res.* 17:99-103; Brattstrom et al, 1998, *Anticancer Res.* 18: 1123-1127). In addition, FGF2 over-expression can be correlated with a chemoresistance in certain cancers including bladder, breast, head and neck cancers (Gan et al, 2006, *Pharm Res.* 23:1324-31). With respect to FGF family members, as FGFs secreted by tumor cells have affinities for the glycosaminoglycan side-chains of cell surface and matrix proteoglycans, these secreted FGFs are most likely sequestered nearby tumor cells forming FGF reservoirs. This particularity makes FGF addressing a good strategy to direct an active molecule that needs a target molecule stably expressed and easily accessible.

Various antibody-based products are currently used as therapeutic drugs and several monoclonal antibodies (mAbs) are now approved in various therapeutic areas such as oncology, inflammation, infectious disease and cardiovascular disease. These mAbs induce tumor cells killing by multiple mechanisms including recruitment of immune system (Harris, 2004, *Lancet Oncol*, 5: 292-302). The Fc moiety of mAbs is responsible for these immune-mediated effector functions that include two major mechanisms: Antibody-Dependent Cell-mediated Cytotoxicity (ADCC) and Complement-Dependent Cytotoxicity (CDC). ADCC occurs when an mAb first binds via its antigen-binding site to its target on tumor cells, and then the Fc portion is recognized by specific Fc receptors (FcR) on effector cells (i.e. NK, neutrophiles, macrophages . . . ) that attack the target cell. CDC is a process where a cascade of different complement proteins become activated when an mAb binds to C1q leading to formation of C3b on the surface of antibody-coated tumor cells near the site of complement activation. The presence of C3b controls formation of the C5-C9 membrane attack complex that can insert into the membrane to lyse tumor cells (Sharkey, 2007, *CA Cancer J Clin*, 56: 226-243). The ability of mAbs to stimulate ADCC depends on their isotype. IgG1 and IgG3 antibodies bind highly to FcRs, while IgG4 and IgG2 antibodies bind weakly. CDC capacity of mAb also depends on mAb isotype. IgG3 and, to a lesser extent, IgG1 are the most effective isotypes for stimulating the classic complement cascade. IgG2 mAbs are less efficient in activating the complement cascade, whereas IgG4 is unable to do so (Strome, 2007, *The Oncologist*, 12:1084-1095).

The use of a fusion protein that can have, as antibodies, a dual functionality with a binding part exhibiting a specific targeting and an effector part able to induce the lysis of target cells by recruitment of immune system, is one aspect of these therapeutic strategies. In addition, to be useful in therapy, this molecule would need to have advantageous pharmacokinetic properties PK. The Fc moiety can detectably increase the serum half life of the modified soluble FGF receptor Fc fusion, but there is still a need for fusion protein with a longer serum half life. Finally, if this fusion protein is to be used as a drug, it is necessary that it is produced reliably, efficiently and with appropriate productivity.

Thus there is a need for a fusion protein with ADCC and/or CDC activities targeting FGF for treatment of cancer, metastatic tumors and for reducing tumor growth in a subject, with improved PK features, and which can be produced efficiently.

The applicants have now discovered that soluble fusion proteins between soluble FGF receptor part (binding or targeting moiety) and Fc part (effector function moiety) (sF- GFR-Fc) that are modified to have a particular glycan profile have in fact substantially improved biological activities, including ADCC and/or CDC activities, and may thus be used as efficacious anti-angiogenic and anti-tumoral drugs, for the treatment of uncontrolled cell growth or cancer. These modified soluble fusion proteins have advantageous PK properties due to their sialylation rate, and can be produced with appropriate productivity and minimal aggregation because of their glycosylation pattern.

SUMMARY OF THE INVENTION

The present invention is thus directed to a modified soluble FGF receptor Fc comprising a fusion of a soluble fragment or domain of a FGF receptor with an Fc region of an immunoglobulin, wherein at least the $5^{th}$ N-glycosylation site of the FGF receptor moiety is occupied, and wherein at most 45% of the N-glycans of the FGF receptor moiety have no sialyl group. In addition, according to a further preferred embodiment of the invention, the $3^{rd}$, $4^{th}$, $6^{th}$ and $7^{th}$ N-glycosylation sites of the FGF receptor moiety are occupied. Preferably, all N-glycosylation sites are occupied. In a further preferred embodiment, the average number of sialic acid per N-glycan in the FGF receptor moiety of the fusions of the invention is at least 0.9; even more
preferably, it is at least 1.2. Each N-glycan molecule of the modified soluble FGF receptor Fc fusion according to the present invention comprises 3 mannose residues, on average 1.5 to 3.0 galactose residues, 3.5 to 5 of N-acetylglucosamine, and 0.6 to 1 fucose residues.

The present invention is also directed to modified soluble FGF receptor Fc fusions comprising a fusion of a soluble fragment or domain of a FGF receptor with an Fc region of an immunoglobulin, wherein all N-glycosylation sites are occupied, and wherein at most 45% of the N-glycans of the FGF receptor moiety have no sialyl group and wherein the N-glycan of the Fc region is 60 to 100% fucosylated.

In one embodiment, the soluble fragment or domain of the FGF receptor is the soluble or extracellular domain of FGF receptor 1 (sFGFR1) or of FGF receptor 2 (sFGFR2).

In another embodiment, the soluble fragment or domain of the FGF receptor is the soluble or extracellular domain of FGF receptor 1 isotype or variant IIIc (sFGFR1(IIIc)) or of FGF receptor 2 isotype IIIc (sFGFR2(IIIc)).

According to a preferred embodiment, the modified soluble FGF receptor Fc fusion is encoded by a polynucleotide having the nucleotide sequence as set forth in the SEQ ID NO: 1, or a polynucleotide having at least 80% identity with the nucleotide sequence of SEQ ID NO: 1. In a further preferred embodiment, the modified soluble FGF receptor Fc fusion of the invention has the amino acid sequence as set forth in the SEQ ID NO: 2 or a sequence having at least 95%, 97%, 98%, or 99% identity with the sequence as set forth in SEQ ID NO: 2.

The modified soluble FGF receptor Fc fusion of the invention has ADCC and/or CDC activity and is thus useful for the treatment of diseases such as cancer.

The present invention also relates to pharmaceutical compositions comprising such modified soluble FGF receptor Fc fusions.

The present invention further relates to the combination of the modified soluble FGF receptor Fc fusion with a chemotherapeutic agent or a biotherapeutic agent with anti-tumoral and/or anti-angiogenic properties.

Another object of the present invention is a method of treatment of cancer, or a method of preventing or reducing tumor growth and volume and metastatic tumors comprising administering to a subject the modified soluble FGF receptor Fc fusion of the present invention in a therapeutically effective amount.

BRIEF DESCRIPTION OF THE FIGURES

FIGS. 2 A and B show the nucleic acid (SEQ ID No. 9) and amino acid (SEQ ID No. 10) sequences of B4GT1 (B4GALT1) for expression from pXL4551

FIGS. 3 A and B show the nucleic acid (SEQ ID No. 11) and amino acid (SEQ ID No. 12) sequences of SIAT6 (ST3GAL3) for expression from pXL4544

FIG. 4 A corresponds to the nucleic acid sequence of sFGFR2-Fc for expression from pXL4410, pXL4429 or pXL4636 (SEQ ID No. 1), FIG. 4 B to the amino acid sequence of sFGFR2-Fc (the N-glycosylation sites are indicated in bold type) encoded by pXL4410 pXL4429 or pXL4636 (SEQ ID No. 2), FIG. 4 C to the amino acid sequence of sFGFR2 (SEQ ID No. 4), FIG. 4 D to the amino acid sequence of Fc (SEQ ID No. 6), FIG. 4 E to the amino acid sequence of the linker, and FIG. 4F to the amino acid sequence of the signal peptide (SEQ ID No. 8). It is the signal peptide described for interleukin-2. It was observed that fusion of this peptide upstream of the sequence represented by SEQ ID No. 2 leads to a secreted protein with a homogeneous N-terminal amino acid sequence.

FIG. 19A shows a map of the plasmid encoding sFGFR2-Fc (A265 in Fc), and FIG. 19B shows the protein sequence of sFGFR2-Fc (A265 in Fc) (SEQ ID No. 14). Position 392 is the position of the mutation in the Fc domain (Asp265Ala) and is represented in bold type.

DETAILED DESCRIPTION

Figures 1A, 1B:
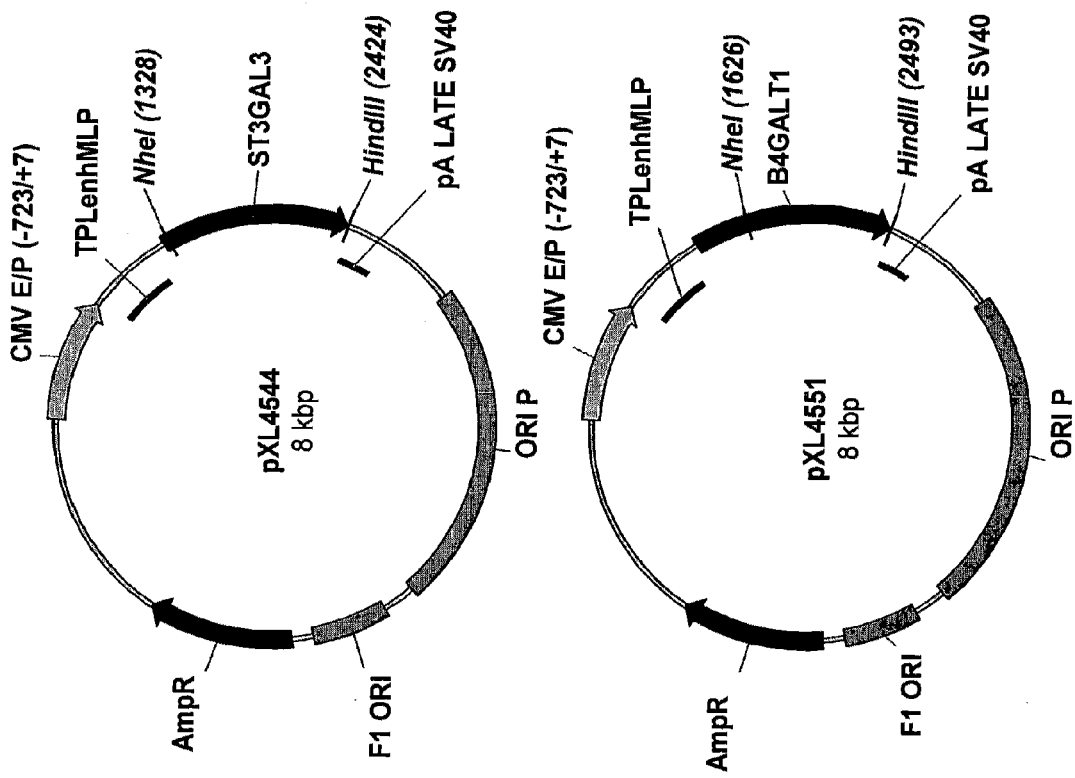
FIGS. 1A and B show maps of the expression vectors for SIAT6 (ST3GAL3) and B4GT1(B4GALT1), respectively.

Throughout this disclosure, applicants refer to journal articles, patent documents, published references, web pages, sequence information available in databases, and other sources of information. One skilled in the art can use the entire contents of any of the cited sources of information to make and use aspects of this invention. Each and every cited source of information is specifically incorporated herein by reference in its entirety. Portions of these sources may be included in this document as allowed or required. However, the meaning of any term or phrase specifically defined or explained in this disclosure shall not be modified by the content of any of the sources. The description and examples that follow are merely exemplary of the scope of this invention and content of this disclosure. One skilled in the art can devise and construct numerous modifications to the examples listed below without departing from the scope of this invention.

The present invention relates to soluble protein fusions comprising domains of FGF receptors. The invention generally encompasses FGF receptor fragments, domains, and especially soluble or extracellular domains. The extracellular domain of the FGF receptor is linked to an appropriate fusion partner, such as an immunoglobulin Fc unit. Therefore, in the broadest sense, the modified soluble FGF receptor fusions of the invention can be FGF receptor (FGFR) proteins, fragments, domains, extracellular domains, soluble domains, and any of these linked to a fusion partner, especially an Fc region fusion partner.

This applicant has found that a modified soluble FGF receptor Fc fusion comprising a fusion of a soluble domain of a FGF receptor with an Fc region of an immunoglobulin wherein at most 45% of the N-glycans have no sialyl group have advantageous properties. Advantages of the sialylation pattern of the modified soluble FGF receptor Fc fusion of the invention include a better pharmacokinetic profile and an improved resistance to cleavage in vivo.

Typically N-glycans are attached cotranslationally through specific asparagine (Asn) residues. The consensus sequence Asn-X-Ser/Thr (where X is any amino acid except Pro) is essential but not sufficient in that local secondary structure may determine addition (Jefferis et al., 2006, *Nature Biotechnology* 24:1241). Several factors are believed to account for unoccupied N-glycosylation sites (Jones et al., 2005, *Biochimica et Biophysica Acta* 1726: 121). Several N-glycosylation sites are present within the soluble FGF receptors of the invention. For example, there are 8 N-glycosylation sites in the extracellular domain of FGFR2IIIc (see FIG. 9). The N-glycans contain a conserved oligosaccharide core linked to Asn. This core is composed of three mannose (Man) and two N-acetylglucosamine (GlcNAcs) monosaccharide residues. Additional GlcNAcs are normally linked to β1,2-linked to the α6 Man or α3 Man, while the N-acetylneuraminic acid (NeuAcα2,6), galactose (Galβ1,4), fucose (Fucα1,6) and bisecting GlcNAc (β1,4) can be present or absent (Jefferis et al., 2006, *Nature Biotechnology* 24:1241).

The applicant has demonstrated that the presence of a N-glycan on the $5^{th}$ N-glycosylation site from the N-terminus of the FGFR moiety confers advantageous properties for productivity and low aggregation, as shown in the Experimental Examples. In particular, in the absence of glycosylation on this particular site, productivity drops dramatically, while aggregation is increased. In addition, the presence of this N-glycan was found to be necessary for FGF binding.

The present invention is thus directed to a modified soluble FGF receptor Fc fusion comprising a fusion of a soluble domain of a FGF receptor with an Fc region of an immunoglobulin, wherein at least the $5^{th}$ N-glycosylation site of the FGF receptor moiety is occupied, and at most 45% of the N-glycans of said FGF receptor moiety have no sialyl group.

According to a further embodiment of the invention, the $3^{rd}$, $4^{th}$, $6^{th}$ and $7^{th}$ N-glycosylation sites of the FGF receptor moiety are occupied. When at least 7 of the N-glycosylation sites of the FGF receptor moiety are glycosylated, the fusion of the invention has even better properties as regards productivity and low aggregation. Thus, in another aspect, the invention is directed to a fusion of a soluble fragment or domain of a FGF receptor with an Fc region of an immunoglobulin, wherein at least 7 N-glycosylation sites are occupied and at most 45% of the N-glycans of the FGF receptor Fc fusion have no sialyl group. In a specific embodiment of the invention, all the N-glycosylation sites are occupied.

In another aspect, the modified soluble FGF receptor Fc fusion of the invention has an average number of sialic acid per N-glycan of the FGF receptor moiety is at least 0.9, i.e. this number can be 0.9 or any value above 0.9. In a preferred embodiment, the modified soluble FGF receptor Fc fusion of the invention has an average number of sialic acid per N-glycan of at least 1.2. Such a ratio was found by the applicant to ensure a maximized concentration in the blood of the soluble FGF receptor fusion of the invention, that would be comparable to the optimal concentration in the blood found for Fc molecules.

The present invention is further directed to a modified soluble FGF receptor Fc fusion comprising a fusion of a soluble fragment or domain of a FGF receptor with an Fc region of an immunoglobulin, wherein all N-glycosylation sites are occupied, and wherein at most 45% of the N-glycans of the FGF receptor moiety have no sialyl group and wherein the N-glycans of the Fc region are not fucosylated. In another embodiment, the modified soluble FGF receptor Fc fusion of the invention is partially fucosylated, e.g., 0 to 60% fucosylated. In yet another embodiment, the modified soluble FGF receptor Fc fusion of the invention is entirely fucosylated. In a preferred embodiment, the modified soluble FGF receptor Fc fusion of the invention is 60 to 100% fucosylated. In a further preferred embodiment, each N-glycan molecule of the modified soluble FGF receptor Fc fusion according to the present invention further comprises 3 mannose residues, and a mean of 1.5 to 3.0 galactose residues, 3.5 to 5 of N-acetylglucosamine per molecule of glycan, and 0.6 to 1 fucose residues.

According to the invention, the modified soluble FGF receptor Fc fusion binds FGF ligand with high affinity. For example, said fusion binds FGF2 with a $K_D$ value measured by Biacore™ comprised between 1 and 5 nM. In a preferred embodiment of the invention, the $K_D$ value of said fusion for FGF2 measured by Biacore™ is around 1.5 nM.

Such modified fusions as described above are useful as potent and therapeutically effective inhibitors of tumor growth. Indeed the applicant has demonstrated that the modified soluble FGF receptor Fc fusions of the invention are capable of inhibiting tumor growth in vivo. Moreover, said modified soluble FGF receptor Fc fusions of the invention are capable of triggering ADCC and/or CDC responses both in vitro and in vivo. As effective ADCC and/or CDC mediating molecules, these compounds are especially useful to treat FGF-overexpressing cancerous tumors.

The FGFR sequences used for the FGFR compounds, full length or fragments of an FGFR, synthetic FGFR sequences, extracellular domains, soluble domains, or fusions of these, can be selected from any available or known sequences. FGFR belongs to the tyrosine kinase family of receptors and to the immunoglobulin (Ig) supergene family. In transmembrane forms of the receptor, the tyrosine kinase domain is intracellular and the Ig-like domains are extracellular. Both transmembrane and secreted forms bind FGF. There are at least four genes that encode FGFRs that have a common structure of two or three extracellular immunoglobulin (Ig)-like loops (IgI-IgIII) and one intracellular tyrosine kinase domain. Alternative splicing products are also known, from exons encoding the extracellular region, resulting in multiple receptor forms. The third Ig-like loop leads to at least three receptor variants and two membrane-spanning forms are produced by alternative splicing of two exons (IIIb and IIIc) encoding the second half of loop III. For example, a selective polyadenylation site preceding exons IIIb and IIIc is used to produce a soluble form of FGFR1 (IIIa). In humans and mice, the IgIIIa splice variant of FGFR1 encodes a protein that apparently has no hydrophobic membrane-spanning domain and may therefore be a secreted or soluble form of the receptor. The FGFR compounds may also utilize sequences from FGFR1 (Protein locus on NCBI, NP_075598); FGFR2 (Protein locus on NCBI, NP_000132); FGFR3 (Protein locus on NCBI, P22607); and FGFR4 (Protein locus on NCBI, NP_002002) (Kiefer et al., 1991, *Growth Factors* 5:115-127).

Soluble forms of FGF receptors, comprising the extracellular domains, have also been discussed in U.S. Pat. Nos. 5,288,855; 6,656,728; WO 91/00916; WO 92/00999; WO 00/46380; WO 2005/016966; WO 2005/113295; WO 2006/113277; WO 2007/014123; and European Patent 529 076. The FGFR fragments, domains, or soluble or extracellular domains as used in the invention may include the fragment of an FGFR that is extracellular in its native form or consists of all or part of the naturally secreted form. Furthermore, the FGFR sequences as used in this invention can be those specifically described or listed and sequences having about 98%, 97%, 96%, 95%, 94%, 93%, 92%, 91%, or 90% amino acid sequence identity over the full length of the polypeptide sequence described or depicted, or having about 95%, 90%, 85%, 80%, or 75% nucleic acid sequence identity over the polypeptide encoding region for nucleic acids encoding the FGFR sequences of the invention. The fragment or domain could also include additional amino acids or other regions of the FGFR as long as these additional amino acids or regions do not prevent or significantly reduce the ability of the FGFR compound to be used as described in this invention. A polypeptide or fusion protein consisting essentially of a FGFR domain or fragment may contain other amino acids as long as the ability to be expressed in a mammalian cell and bind to FGF are retained, and optionally, in addition, as long as the ability to reduce cell growth or reduce vascularization is retained.

In one embodiment, the soluble fragment or domain of the FGF receptor is the soluble or extracellular domain of FGF receptor 1 (sFGFR1) or FGF receptor 2 (sFGFR2).

The fragments of FGFR1 and FGFR2 selected can have one or more of the following mutations, an N-terminal deletion; of 1-7 amino acids; or N-term substitution; a deletion of the loop1 sequence; a deletion of the acidic box sequence. Polynucleotides encoding amino acid sequence mutants can be prepared by a variety of methods known in the art, including, but not limited to, oligonucleotide-mediated (or site-directed) mutagenesis, PCR mutagenesis and cassette mutagenesis of an earlier prepared mutant or a non-mutant version of the molecule of interest (see, e.g., Kunkel, 1985, *Proc Natl Acad Sci USA* 82:488).

In another embodiment, the soluble fragment or domain of the FGF receptor is the soluble or extracellular domain of FGF receptor 1 isotype IIIc (sFGFR1(IIIc)) and FGF receptor 2 isotype IIIc (sFGFR2(IIIc)).

Preferred embodiments include soluble fragment or domain of the FGF receptor 2 isotype or variant IIIc encoded by a polynucleotide having the sequence of SEQ ID NO: 3, and/or having the amino acid sequence of SEQ ID NO: 4 or a sequence with at least 95%, 97%, 98%, or 99% identity with the SEQ ID NO: 4.

According to this latest embodiment, the modified soluble FGF receptor Fc fusion (sFGFR2-Fc) of the present invention advantageously has a high affinity for its natural ligand FGF2 or high $K_D$ value of the order of the nanomolar, comprised between 1 and 5 nM and more precisely around 1.5 nM.

Specific examples of immunoglobulin domains include, but are not limited to, the Fc region of an immunoglobulin molecule; the hinge region of an immunoglobulin molecule; the $CH_1$ region of an immunoglobulin molecule; the $CH_2$ region of an immunoglobulin molecule; the $CH_3$ region of an immunoglobulin molecule; the $CH_4$ region of an immunoglobulin molecule; and the light chain of an immunoglobulin molecule, and humanized variants of any of these. The sequences for these regions are also available to one of skill in the art (see, for example, Huck et al., 1986, *Nucleic Acids Res.* 14:1779).

As used in the specification and claims, "immunoglobulin Fc region or Fc" means the carboxyl-terminal portion of an immunoglobulin heavy chain constant region. The Fc regions are particularly important in determining the biological functions of the immunoglobulin and these biological functions are termed effector functions. As known in the art, the heavy chains of the immunoglobulin subclasses comprise four or five domains: IgM and IgE have five heavy chain domains, and IgA, IgD and IgG have four heavy chain domains. The Fc region of IgA, IgD and IgG is a dimer of the hinge-$CH_2$—$CH_3$ domains, and in IgM and IgE it is a dimer of the hinge-$CH_2$—$CH_3$—$CH_4$ domains. Further the $CH_3$ domain of IgM and IgE is structurally equivalent to the $CH_2$ domain of IgG, and the $CH_4$ domain of IgM and IgE is the homolog of the $CH_3$ domain of IgG (see, W. E. Paul, ed., 1993, Fundamental Immunology, Raven Press, New York, N.Y.). Any of the known Fc regions would be useful as the Fc region in the modified soluble FGF receptor Fc fusions of the invention.

In one embodiment, the gene encoding the Fc region of human IgG (Fc$_\gamma$) is obtained by reverse transcription and PCR using RNA prepared from human leukocytes and appropriate 5' and 3' primers. The resulting DNA fragments contain complete sequences of the hinge, $CH_2$, and $CH_3$ domains of IgG and can be used as the template to generate variants in which certain amino acids are substituted, as known in the art. A primer encoding a peptide linker, including an optional restriction enzyme site, can be incorporated into the PCR process. The resulting DNA fragments are inserted into a holding vector and confirmed by DNA sequencing.

Preferably, the Fc region of immunoglobulin gamma-1 is used, which includes at least part of the hinge region, $CH_1$ region, $CH_2$ region, and $CH_3$ region. In addition, the Fc region of immunoglobulin gamma-1 can be a $CH_1$-deleted -Fc or a $CH_2$-deleted-Fc, and includes a part of a hinge region and a $CH_3$ region wherein the $CH_1$ and/or $CH_2$ region has been deleted. A $CH_2$-deleted-Fc has been described by Gillies et al., (1990, *Hum. Antibod. Hybridomas*, 1:47).

Most preferably, the Fc region of IgG1 comprises the sequence encoded by a polynucleotide having the sequence of SEQ ID NO: 5, and/or the amino acid sequence as set forth in SEQ ID NO: 6 or a sequence with at least 95% identity with SEQ ID NO: 6. However, Fc regions from the other classes of immunoglobulins, IgA, IgD, IgE, and IgM, would also be useful as the Fc region.

Further, deletion constructs of these Fc regions, in which one or more of the constant domains are deleted, may be prepared. One of ordinary skill in the art could prepare such deletion constructs using well known molecular biology techniques. In addition, the Fc region used can be one that has about 99%, or about 98%, or about 95%, or about 90%, or about 85%, or about 80%, or about 75% amino acid identity to that shown in SEQ ID NO:6.

Specific mutations as compared to SEQ ID NO: 6 that can be selected from and used individually or in any combination are: a deletion or substitution of one of the Cys within the first 20 N-term amino acids; a deletion of Cys at position 5 in SEQ ID NO: 6; or a substitution of Cys at position 5. The Fc region sequence chosen can detectably increase the serum half life of the modified soluble FGF receptor Fc fusion.

The modified soluble FGF receptor Fc fusion of the invention may comprise a hinge or a spacer region can be used between the soluble receptor part and the Fc region, (Ashkenazi et al., 1997, *Current Opinion in Immunology*, 9:195-200). Examples include a flexible peptide linker of about 20 or fewer amino acids in length. More preferably, the peptide linker may be at least three amino acids in length, and/or a peptide linker comprising two or more of the following amino acids: glycine, serine, alanine, and threonine. In a preferred embodiment, the peptide linker does not include a protease cleavage site. Most preferred linker is SAL (Ser-Ala-Leu).

The present invention also provides for the construction of polynucleotides encoding the modified soluble FGF receptor Fc fusion according to the present invention as well as a vector capable of expressing the modified soluble FGF receptor Fc fusion when introduced into an appropriate host cell. According to the preferred embodiment, the polynucleotide encoding the modified soluble FGF receptor Fc fusion has the sequence of SEQ ID NO: 1, or a sequence sharing at least 80% identity with SEQ ID NO: 1. As used herein, "vector" is understood to mean any nucleic acid comprising a nucleotide sequence of interest and capable of being incorporated into a host cell, and optionally to express an encoded protein or polypeptide. Vectors include linear nucleic acids, plasmids, phagemids, cosmids and the like, all within the knowledge of a person skilled in the art. Polynucleotides encoding the FGFR or fusion compound of the invention, as well as vectors containing these nucleic acids and host cells wherein these vectors have been introduced, are also specifically incorporated into the scope of the invention.

Most preferably, the fusion molecules of the invention are encoded by DNA comprising an extracellular domain of an FGFR fused at the C terminus to the Fc$\gamma$1 region of the human immunoglobulin $\gamma$1 gene. The Fc$\gamma$1 region of the immunoglobulin $\gamma$1 gene includes at least a portion of the hinge domain and $CH_3$ domain, or at least a portion of the hinge domain, $CH_2$ domain and $CH_3$ domain. The DNA encoding the chimeric polypeptide molecules according to the present invention can be in its genomic configuration or its cDNA configuration. Signal peptides may be used to efficiently initiate the transport of a protein across the membrane of the endoplasmic reticulum. Signal sequences have been well characterized in the art and are known typically to contain 16 to 30 amino acid residues, although other sizes are possible. A detailed discussion of signal peptide sequences is provided by von Heijne (1986, *Nucleic Acids Res.*, 14:4683). According to a preferred embodiment, the signal peptide is taken from Interleukin-2 signal peptide (SEQ ID No. 8) as known in the art. The applicant has observed that fusing this peptide to an extracellular domain of an FGFR leads to a secreted protein with a homogenous N-terminal amino acid sequence, which is not the case when the endogenous FGFR signal peptide is used.

An expression vector containing the coding sequences of the modified soluble FGF receptor Fc fusion of the invention placed under the control of appropriate transcriptional and translational regulatory sequences can be constructed by recombinant DNA technology as known in the art. Such expression vector is introduced into a host cell by any technique known to the person skilled in the art. The resulting vector-containing cell is then grown to produce a modified soluble FGF receptor Fc fusion or fragment thereof, using any technique known to the person skilled in the art.

According to the invention, a variety of expression systems may be used to express the modified soluble FGF receptor Fc fusion molecules. In one aspect, such expression systems represent vehicles by which the coding sequences of interest may be produced and subsequently purified, but also represent cells which may, when transiently transfected with the appropriate nucleotide coding sequences, express a modified soluble FGF receptor Fc fusion molecule of the invention in situ. Mammalian cells are commonly used for the expression of a recombinant modified soluble FGF receptor Fc fusion molecule, especially for the expression of whole recombinant modified soluble FGF receptor Fc fusion molecule. For example, mammalian cells such as HEK293 or CHO cells, in conjunction with a vector, containing the expression signal such as one carrying the major intermediate early gene promoter element from human cytomegalovirus, are an effective system for expressing the modified soluble FGF receptor Fc fusions of the invention (Foecking et al., 1986, *Gene* 45:101; Cockett et al., 1990, *Bio/Technology* 8:2).

In addition, a host cell is chosen which modulates the expression of the inserted sequences, or modifies and processes the gene product in the specific fashion desired. Such modifications (e.g., glycosylation) and processing of protein products may be important for the function of the protein. Different host cells have features and specific mechanisms for the post-translational processing and modification of proteins and gene products. Appropriate cell lines or host systems are chosen to ensure the correct modification and processing of the expressed modified soluble FGF receptor Fc fusion of interest. Hence, eukaryotic host cells which possess the cellular machinery for proper processing of the primary transcript, glycosylation of the gene product may be used. Such mammalian host cells include, but are not limited to, CHO, COS, HEK293, 3T3 or myeloma cells. The host cell may be co-transfected with two or more expression vectors, including the vector expressing the protein of the invention. For example, a host cell can be transfected with a first vector encoding a modified soluble FGF receptor Fc fusion polypeptide, as described above, and a second vector encoding a glycosyltransferase polypeptide. Alternatively, the second vector could express a small interfering RNA against a glycosyltransferase.

For long-term, high-yield production of recombinant proteins, stable expression is preferred. In one embodiment of the invention, cell lines which stably express the modified soluble FGF receptor Fc fusion molecule may be engineered. Rather than using expression vectors which contain viral origins of replication, host cells are transformed with DNA under the control of the appropriate expression regulatory elements, including promoters, enhancers, transcription terminators, polyadenylation sites, and other appropriate sequences known to the person skilled in art, and a selectable marker. Following the introduction of the foreign DNA, engineered cells may be allowed to grow for one to two days in an enriched media, and then are moved to a selective media. The selectable marker on the recombinant plasmid confers resistance to the selection and allows cells to stably integrate the plasmid into a chromosome and be expanded into a cell line.

A number of selection systems may be used according to the invention, including but not limited to the Herpes simplex virus thymidine kinase (Wigler et al., 1977, *Cell* 11:223), hypoxanthine-guanine phosphoribosyltransferase (Szybalska et al., 1992, Proc Natl Acad Sci USA 48:202), glutamate synthase selection in the presence of methionine sulfoximine (*Adv Drug Del Rev,* 2006, 58: 671, and website or literature of Lonza Group Ltd.) and adenine phosphoribosyltransferase (Lowy et al., 1980, *Cell* 22:817) genes in tk, hgprt or aprt cells, respectively. Also, antimetabolite resistance can be used as the basis of selection for the following genes: dhfr, which confers resistance to methotrexate (Wigler et al., 1980, *Proc Natl Acad Sci USA* 77:357); gpt, which confers resistance to mycophenolic acid (Mulligan et al., 1981, *Proc Natl Acad Sci USA* 78:2072); neo, which confers resistance to the aminoglycoside, G-418 (Wu et al., 1991, *Biotherapy* 3:87); and hygro, which confers resistance to hygromycin (Santerre et al., 1984, *Gene* 30:147). Methods known in the art of recombinant DNA technology may be routinely applied to select the desired recombinant clone, and such methods are described, for example, in Ausubel et al., eds., *Current Protocols in Molecular Biology*, John Wiley & Sons (1993). The expression levels of a modified soluble FGF receptor Fc fusion molecule can be increased by vector amplification. When a marker in the vector system expressing a modified soluble FGF receptor Fc fusion is amplifiable, an increase in the level of inhibitor present in the culture will increase the number of copies of the marker gene. Since the amplified region is associated with the gene encoding the modified soluble FGF receptor Fc fusion of the invention, production of said modified soluble FGF receptor Fc fusion will also increase (Crouse et al., 1983, *Mol Cell Biol* 3:257).

A number of factors are known to the person skilled in the art to influence the glycosylation level of a glycoprotein. For example, modified mammalian host cells can be used to alter the glycosylation profile of modified soluble FGF receptor Fc fusion by increasing or diminishing the expression of glycosyltransferase. Such modified mammalian host cells include, but are not limited to, CHO, COS, HEK293, PER.C6, 3T3, YB2/0 and myeloma cells (Stanley et al., 1986, *Archives of Biochemistry and Biophysics,* 249:533; Mori et al., 2006, *Biotechnology and Bioengineering* 94:68; Chitlaru et al., 1998, *Biochem. J.* 336:647; Umana et al., 1999 *Nature Biotechnology* 17:176). It is also known to the person skilled in the art that bioprocess factors affect glycoprotein oligosaccharide biosynthesis (Goochee et al., 1994, *Curr Opin Biotechnol.* 5:546). The effect of cell culture conditions, such as glucose or ammonium ions concentration, pH, serum, and the effects of other bioprocess factors, such as cell growth rate, cultivation time, influence N-linked glycosylation (*Biotechnol. Bioeng.* 39:327 (1993); *Biotechnol. Bioeng.* 68:370 (2000); *Bio/technology* 11:720 (1993); *Cytotechnology* 17:13 (1995); *Biochem J.* 272:333 (1990)). It is also known that in addition to the host cells and the bioprocess factors, the oligosaccharide processing is influenced by the local environment at each N-glycosylation site pending on the local glycoprotein environment. Site-to-site differences may be extensive as was observed with t-PA or may involve more subtle differences in branching and terminal processing as observed for the three N-glycosylation sites of EPO (Goochee et al, 1991, *Bio/Technology* 9: 1347).

After it has been produced, a modified soluble FGF receptor Fc fusion of the invention may be purified by any method known in the art for purification of an immunoglobulin molecule, for example, by chromatography (e.g., ion exchange, affinity, particularly by Protein A affinity for Fc after and so on), centrifugation, differential solubility or by any other standard technique for the purification of proteins.

Quantitative sialic acid identification (N-acetylneuraminic acid residues), carbohydrate composition analysis and quantitative oligosaccharide mapping of N-glycans in the purified modified soluble FGF receptor Fc fusion proteins can be performed essentially as described previously (Saddic et al. Methods Mol. Biol. 194:23-36 (2002) and Anumula et al. Glycobiology 8:685-694 (1998)).

Fusion proteins incorporating soluble FGF receptor domains can be produced by methods familiar to those in the art for any other mammalian, expressible or biologically active fusion, mutatis mutandis. For example, methods reported to combine the Fc regions of IgG with the domains of cytokines and soluble receptors can be adopted to design and produce the FGFR compounds of the invention (see, for example, Capon et al., Nature, 337:525-531 (1989); Chamow et al., Trends Biotechnol., 14:52-60 (1996); U.S. Pat. No. 5,116,964, U.S. Pat. No. 5,349,053 and U.S. Pat. No. 5,541,087). Other examples of receptor-Ig fusion proteins that can be adopted include those of U.S. Pat. No. 5,726,044; U.S. Pat. No. 5,707,632; and U.S. Pat. No. 5,750,375. Because FGF receptor extracellular domains share a significant degree of homology to the immunoglobulin gene family and the FGFR extracellular domain contains Ig-like segments, the use of Fc regions is especially preferred. In one example, the fusion is a homodimeric protein linked through cysteine residues in the hinge region of IgG Fc, resulting in a molecule with similar characteristics to an IgG molecule. One advantage to using an Fc region is extended circulating half-life. In addition, the glycosylation modifications of the modified soluble FGF receptor Fc fusion proteins of the invention lead to improved pharmacokinetic properties, as the fusions of the invention exhibit in vivo pharmacokinetic profiles comparable to human IgG of a similar isotype.

A further embodiment of the present invention provides a method for making a modified soluble FGF receptor Fc fusion protein comprising a FGFR fragment or domain, a flexible peptide linker, and a human IgG Fc variant, which method comprises: (a) generating a CHO-derived cell line;

(b) growing the cell line under conditions such that the recombinant fusion protein is expressed; and (c) purifying the expressed protein from step (b). In this case, preferably, the flexible peptide linker comprising at least about 3 amino acids between the soluble FGF receptor and the human IgG Fc variant comprises two or more amino acids selected from the group consisting of glycine, serine, alanine, and threonine. In additional and related embodiments, the linker peptide is not present or is only one amino acid in length. In a preferred embodiment, the peptide linker does not include a protease cleavage site. The most preferred linker is SAL (Ser-Ala-Leu).

Preferably, the modified soluble FGF receptor fusion protein is produced in CHO cells in a suspension mode as described in the Examples herein.

As shown in the Examples herein, the modified soluble FGF receptor Fc fusions of the present invention have antitumoral activity, at least through induction of ADCC and/or CDC responses, and are thus useful in the treatment of metastatic tumors and diseases such as cancer. One aspect of the invention is thus directed to a modified soluble FGF receptor Fc fusion as described above with ADCC and/or CDC activities.

Of special interest are modified soluble FGF receptor Fc fusions with enhanced ability to mediate cellular cytotoxic effector functions such as ADCC. Such proteins may be obtained by making single or multiple substitutions in the Fc region of the molecule, thus altering its interaction with the Fc receptors. Methods for designing such mutants can be found for example in Lazar et al. (2006, *Proc. Natl. Acad. Sci. U.S.A.* 103(11): 4005-4010) and Okazaki et al. (2004, *J. Mol. Biol.* 336(5):1239-49). See also WO 03/074679, WO 2004/029207, WO 2004/099249, WO2006/047350, WO 2006/019447, WO 2006/105338, WO 2007/041635. It is also possible to use cell lines specifically engineered for production of improved modified soluble FGF receptor Fc fusions. In particular, these lines have altered regulation of the glycosylation pathway, resulting in modified soluble FGF receptor Fc fusions which are poorly fucosylated or even totally defucosylated. Such cell lines and methods for engineering them are disclosed in e.g. Shinkawa et al. (2003, *J. Biol. Chem.* 278(5): 3466-3473), Ferrara et al. (2006, *J. Biol. Chem.* 281(8): 5032-5036; 2006, *Biotechnol. Bioeng.* 93(5): 851-61), EP 1331266, EP 1498490, EP 1498491, EP 1676910, EP 1792987, and WO 99/54342.

Methods of inhibiting tumor growth in a subject, and methods for the treatment or prevention of metastasis in a subject, comprising administering an efficient amount of such modified soluble FGF receptor Fc fusions as described above, are an aspect of the invention. The invention thus also relates to the modified soluble FGF receptor Fc fusion as described above as a medicament. The present invention also relates to the use of the modified soluble FGF receptor Fc fusion as described above for the preparation of a medicament for treating or inhibiting tumor growth in a subject.

Another aspect of the invention relates to pharmaceutical compositions of the modified soluble FGF receptor Fc fusion of the invention. The pharmaceutical compositions of the invention typically comprise the modified soluble FGF receptor Fc fusion of the invention and a pharmaceutically acceptable carrier. As used herein, "pharmaceutically acceptable carrier" includes any and all solvents, buffers, salt solutions, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of media and agents for pharmaceutically active substances is well known in the art. As detailed herebelow, additional active compounds can also be incorporated into the compositions, such as anti-cancer and/or anti-angiogenesis agents; in particular, the additional active compound can be an anti-angiogenic agent, a chemotherapeutic agent, or a low-molecular weight agent. A typical pharmaceutical composition for intravenous infusion could be made up to contain 250 ml of sterile Ringer's solution, and 100 mg of the combination. Actual methods for preparing parenterally administrable compounds will be known or apparent to those skilled in the art and are described in more detail in for example, Remington's Pharmaceutical Science, 17th ed., Mack Publishing Company, Easton, Pa. (1985), and the 18$^{th}$ and 19$^{th}$ editions thereof, which are incorporated herein by reference.

The modified soluble FGF receptor Fc fusion of the invention can also be prepared with carriers and controlled-release formulations, including implants and microencapsulated delivery systems. Biodegradable and biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

The modified soluble FGF receptor Fc fusion in the composition preferably is formulated in an effective amount. An "effective amount" refers to an amount effective, at dosages and for periods of time necessary, to achieve the desired result, such as modulation of FGF and/or FGFR activities and induction of ADCC and/or CDC responses. A "therapeutically effective amount" means an amount sufficient to influence the therapeutic course of a particular disease state. A therapeutically effective amount is also one in which any toxic or detrimental effects of the agent are outweighed by the therapeutically beneficial effects.

For therapeutic applications, the modified soluble FGF receptor Fc fusions of the invention are administered to a mammal, preferably a human, in a pharmaceutically acceptable dosage form such as those discussed above, including those that may be administered to a human intravenously as a bolus or by continuous infusion over a period of time, by intramuscular, intraperitoneal, intracerobrospinal, subcutaneous, intraarticular, intrasynovial, intrathecal, oral, topical, or inhalation routes. The modified soluble FGF receptor Fc fusions also are suitably administered by intratumoral, peritumoral, intralesional, or perilesional routes, to exert local as well as systemic therapeutic effects. The intraperitoneal route is expected to be particularly useful, for example, in the treatment of ovarian tumors.

Dosage regimens may be adjusted to provide the optimum response. For example, a single bolus may be administered, several divided doses may be administered over time, or the dose may be proportionally reduced or increased. The compositions of the invention can be administered to a subject to effect cell growth activity in a subject. As used herein, the term "subject" is intended to include living organisms in which an FGF-dependent cell growth exists and specifically includes mammals, such as rabbits, dogs, cats, mice, rats, monkey transgenic species thereof, and humans.

The modified soluble FGF receptor Fc fusions and the pharmaceutical compositions of the invention are useful in the treatment or prevention of a variety of cancers, including (but not limited to) the following: carcinoma, including that of the bladder, breast, colon, head and neck, kidney, including renal cell carcinoma, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyosarcoma, and osteosarcoma; and other tumors, including melanoma, xeroderma pigmentosum, keratoctanthoma, seminoma, thyroid follicular cancer and teratocarcinoma, and other cancers yet to be determined which are caused by FGF overexpression. In a preferred embodiment, the modified soluble FGF receptor Fc fusion of the invention is used to treat melanoma, leukemia, renal cancer, colon cancer, ovarian cancer, prostate cancer, lung cancer, bladder cancer, breast cancer, or head and neck cancer.

The present invention thus relates to the use of the modified soluble FGF receptor Fc fusion described above for the preparation of a medicament for treating or inhibiting cancer-related diseases in a subject. It is an aspect or object of the present invention to provide a method of treating diseases and processes that result from cancer cell proliferation, and a composition for treating or repressing the growth of a cancer. Yet another aspect of the invention is to provide compositions and methods useful for gene therapy for the modulation of cancer. The method of the present invention may be used in particular for the treatment of melanoma, leukemia, renal cancer, colon cancer, ovarian cancer, prostate cancer, lung cancer, bladder cancer, breast cancer, or head and neck cancer.

The effectiveness of the modified soluble FGF receptor Fc fusion in preventing or treating disease may be improved by administering said fusion serially or in combination with another agent that is effective for those purposes, such as tumor necrosis factor (TNF), an antagonist capable of inhibiting or neutralizing the angiogenic activity of acidic or basic fibroblast growth factor (FGF), platelet-derived growth factor (PDGF), or hepatocyte growth factor (HGF), an antagonist capable of inhibiting or neutralizing the coagulant activities of tissue factor, protein C, or protein S (see WO 91/01753), an antagonist such as an antibody capable of binding to HER2 receptor (see U.S. Pat. No. 5,772,997), or one or more conventional therapeutic agents such as, for example, alkylating agents, folic acid antagonists, anti-metabolites of nucleic acid metabolism, antibiotics, pyrimidine analogs, 5-fluorouracil, cisplatin, purine nucleosides, amines, amino acids, triazol nucleosides, or corticosteroids.

In another aspect of the invention, the administration is combined with an administration of therapeutically effective amount of chemotherapeutic agent, such as for example, taxol (paclitaxel) or taxotere (docetaxel).

Chemotherapeutic agents include without any limitations, anti-microtubule agents such as diterpenoids and vinca alkaloids; platinum coordination complexes; alkylating agents such as nitrogen mustards, oxazaphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and antifolate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors. In addition, the methods of the invention can be combined with another anti-cancer treatment, anti-angiogenic agent, or chemotherapeutic agent or radiation therapy. A preferred example is docetaxel or taxotere. Other examples include, gemcitabine, cisplatin diterpenoids and vinca alkaloids, paclitaxel, vinblastine, vincristine, and vinorelbine, carboplatin, cyclophosphamide, melphalan, and chlorambucil, busulfan, carmustine, dacarbazine, cyclophosphamide, melphalan, chlorambucil, busulfan, carmustine, dacarbazine, anti-neoplastic agents including, but not limited to, actinomycins such as dactinomycin, anthrocyclins such as daunorubicin and doxorubicin, bleomycins, epipodophyllotoxins, etoposide and teniposide; antimetabolite neoplastic agents, 5-fluorouracil, methotrexate, cytarabine, mercaptopurine, thioguanine, camptothecins, irinotecan HCl, and topotecan HCl.

A variety of different chemotherapeutic agents or anti-cancer polypeptides can also be selected. Information sources such as www.clinicaltrials.gov, www.ncbi.nlm.nih, and www.drugs.com, include references to polypeptides and agents that can be selected.

Such other agents, e.g. anti-angiogenic agents or chemotherapeutic agents may be present in the composition being administered or may be administered separately. In one aspect of the invention, the administration is performed with the other active principle, either simultaneously, separately or sequentially over time. When the administration is performed simultaneously, the two active principles may be combined in a single pharmaceutical composition, comprising the two compositions, such as a tablet or a gel capsule. On the other hand, the two active principles may, whether or not they are administered simultaneously, be present in separate pharmaceutical compositions. To this end, the combination may be in the form of a kit comprising, on the one hand, the modified soluble FGF receptor Fc fusion as described above and, on the other hand, the second active principle, the modified soluble FGF receptor Fc fusion as described above and the second active principle being in separate compartments and being intended to be administered simultaneously, separately, or sequentially over time.

The combination according to the present invention can be administered especially for tumor therapy in combination with chemotherapy, protein therapy (i.e. using a therapeutic agent such as an antibody or recombinant protein), gene therapy, radiotherapy, immunotherapy, surgical intervention, or a combination of these. Long-term therapy is equally possible as is adjuvant therapy in the context of other treatment strategies, as described above.

The examples that follow are merely exemplary of the scope of this invention and content of this disclosure. One skilled in the art can devise and construct numerous modifications to the examples listed below without departing from the scope of this invention.

EXAMPLES

Example 1

Production in HEK293 of sFGFR2-Fc with a High Sialic Acid Content and Low Blood Clearance cDNAs encoding human α-1,4-galactosyltransferase (B4GT1) (SEQ ID No. 9) or human β-2,3-sialyltransferase (SIAT6) (SEQ ID No. 11) were retrieved from clone collection (Invitrogen) and cloned into the mammalian expression vector pXL4214 from which expression is driven from the CMV promoter. The same expression vector was also used to clone the protein fusion sFGFR2-Fc and generate pXL4410. Map of plasmids pXL4551 encoding B4GT1, pXL4544 encoding SIAT6 and pXL4410 encoding the modified soluble FGFR2IIIc-Fc fusion (herein designated as sFGFR2-Fc) are presented on FIGS. 1 and 5 as well as the nucleic acid and corresponding amino acid sequence of B4GT1 (FIG. 2), SIAT6 (FIG. 3) and sFGFR2-Fc (FIGS. 4A and B). sFGFR2-Fc was produced in adherent HEK293 EBNA cells (Invitrogen) by transient transfection of one to three expression plasmids encoding sFGFR2-Fc, B4GT1 or SIAT6 complexed with JET PEI (Q-Biogen). Plasmid ratio was 90/5/5 for pXL4410/pXL4544/pXL4551. Plasmid ratio had to be optimized to ensure optimal productivity and quality of the sFGFR2-Fc polypeptide. Secreted proteins were harvested eight days post-transfection and centrifuged. Proteins were purified by affinity chromatography on Protein G Sepharose (Amersham Biosciences) after elution from the column with 100 mM glycine/HCl pH 2.7. The sFGFR2-Fc proteins were formulated in PBS and 0.22 μm filtered. Protein concentration was determined by the microBC Assay (Interchim). Quantitative sialic acid identification, carbohydrate composition analysis and quantitative oligosaccharide mapping of N-glycans in the sFGFR2-Fc purified proteins were performed essentially as described previously (Saddic et al. 2002. Methods Mol. Biol. 194:23-36 and Anumula et al. 1998. Glycobiology 8:685-694). First, sialic acid residues were released after mild hydrolysis of sFGFR2-Fc and fluorescently labeled with ortho-phenylenediamine and separated by reversed-phase HPLC. Individual peaks were detected by fluorescence detection (excitation, 230 nm; emission, 425 nm), identified and quantitated by comparison with N-acetylneuraminic and N-glycolylneuraminic acid standards. Second, the carbohydrate composition was determined after acid hydrolysis of sFGFR2-Fc samples to release the individual monosaccharides. After hydrolysis, the monosaccharides (neutral and amino sugars) were derivatized with anthranilic acid and then separated by reversed-phase HPLC and detected by fluorescence detection (excitation, 360 nm; emission, 425 nm). Individual peaks were identified and quantitated by comparison with monosaccharide standards. Third, oligosaccharides were enzymatically released with PNGase F and fluorescently labeled with anthranilic acid before separation according to their number of sialic acid residues by normal phase-anion exchange HPLC on an Asahipak-NH2P (Phenomenex) column. Labeled glycans were detected and quantitated by fluorescence detection (excitation, 360 nm; emission, 425 nm). The average number of sialic acid per N-glycan in the FGFR2 domain was calculated based on the total amount of moles of N-glycan per mole of FGFR2-Fc and the moles of N-glycan per Fc mole obtained after release of the Fc by papain.

The purified sFGFR2-Fc proteins were injected in the tail of Swiss Nude mice (Charles River). A total of three mice were used per protein batch. Blood was collected 6-hour post injection of 500 μg of sFGFR2-Fc, plasma was obtained and FGFR2-Fc concentration was determined by ELISA utilizing the sandwich method with an anti-human FGFR2 monoclonal antibody (R&D system) and an anti-human IgG-HRP conjugate polyclonal antibody (Pierce) (2 analysis at 2 dilutions in triplicate). In the control experiments mice were pretreated with fetuin and asiolofetuin one hour prior to injection of sFGFR2-Fc.

Table 1 summarizes the condition of production of the different sFGFR2-Fc batches, the N-glycan profile and monosaccharide composition of each batch and the plasma concentration of sFGFR2-Fc 6-hour post intravenous injection in mice.

TABLE 1

N-Glycan content and pharmacokinetic of FGFR2-Fc produced in HEK293

| Expressed protein in HEK293EBNA | sFGFR2-Fc | sFGFR2-Fc + SIAT6 | sFGFR2-Fc + SIAT6 & B4GT1 |
|---|---|---|---|
| % sFGFR2-Fc sialylated species: | | | |
| 1-non sialylated | 69% | 46% | 34% |
| 2-monosialylated | 23% | 19% | 22% |
| 2-disialylated | 6% | 26% | 35% |
| 3-trisialylated | 1.5% | 10% | 10% |
| Sialic acid content: | | | |
| 1-pmol of N-acetylneuraminic acid per pmol of sFGFR2-Fc | 3.4 | 6.4 | 6.8 |
| 2-Average number of sialic acid per sFGFR2 N-glycan | 0.4 | | 1 |
| Monosaccharide composition of sFGFR2-Fc N-glycans for 3 mannoses | | | |
| 1-Glucosamine (number per 3 mannoses) | 4.3 | 4.1 | 4.1 |
| 2-Galactose (number per 3 mannoses) | 1.5 | 1.4 | 1.6 |
| Number of fucose in Fc N-glycans for 3 mannoses | 0.73 | 0.61 | 0.63 |
| Blood clearance | | | |
| [sFGFR2-Fc] in plasma 6-hour post i.v. injection (ng/mL) | 258 | | 20000 |
| [sFGFR2-Fc] in plasma 6-hour post i.v. injection (ng/mL) when mice were pretreated with fetuin | 229 | Not done | Not done |
| [sFGFR2-Fc] in plasma 6-hour post i.v. injection (ng/mL) when mice were pretreated with asialofetuin | 19276 | Not done | Not done |

Improved sialylation pattern of sFGFR2-Fc fusion proteins produced in HEK293EBNA has been demonstrated by transient co-expression of the fusion protein with human α-1,4-galactosyltransferase or human β-2,3-sialyltransferase. This large improvement of sialylation status was evidenced by a 2-fold reduction of the percentage of non-sialylated glycans, a 2-fold increase in the total sialic acid content per mol of protein and a 2.5-fold increase in the average number of sialic acid per N-glycan. Of note the monosaccharide content was not affected (see Table 1).

This 2.5-fold increase in sialylated N-glycan is directed correlated with the significantly improved pharmacokinetic parameters of sFGFR2-Fc. In particular a 100-fold increase of the sFGFR2-Fc presence in the plasma has been measured 6-hour post iv injection in mice. The pharmacokinetic was also improved by 100-fold when mice were pretreated with asialofetuin compared to the pretreatment with fetuin. Asia- CHO/GS semi-clones (SC#9, 11, 26, 58, 112, 118, 170) were screened for the sialic acid content of the purified sFGFR2-Fc molecules. The two semi-clones with the highest sialic acid content (SC #11 and 118) were selected for cloning and up-scale production; in particular clone from SC#118 was further described as GC111.

Although sFGFR2-Fc molecules produced from all the semi-clones had a high sialic acid content, they did not lead to the same pharmacokinetics. Interestingly, it was observed that from two semi-clones (SC#11 and 118), sFGFR2-Fc with the highest sialic acid content led to the highest sFGFR2-Fc concentration in the blood 6-hour post iv injection in mice, as described on Table 2. And from the two clones (SC#9 and 170) sFGFR2-Fc with the lowest sialic acid content had the lowest sFGFR2-Fc concentration in the blood 6-hour post iv injection in mice.

TABLE 2

CHO stable clones expressing sFGFR2-Fc protein with a ratio of sialic acid residues per sFGFR2 N-glycan greater than 1.2 for optimal pharmacokinetics

| | Purified sFGFR2-Fc from CHO-GS semi-clone SC# | | | | | | |
|---|---|---|---|---|---|---|---|
| | SC# 9 | SC# 11 | SC# 26 | SC# 58 | SC# 112 | SC# 118 | SC# 170 |
| % sFGFR2-Fc sialylated species | | | | | | | |
| 1-non sialylated | 50 | 42 | 48 | 48 | 45 | 43 | 53 |
| 2-monosialylated | 28 | 30 | 30 | 30 | 30 | 30 | 28 |
| 3-disialylated | 14 | 18 | 14 | 15 | 16 | 17 | 13 |
| 4-trisialylated | 8 | 10 | 7 | 8 | 9 | 10 | 6 |
| Average number of sialic acid per sFGFR2 N-glycan | 1.07 | 1.45 | | | | 1.29 | 0.98 |
| [sFGFR2-Fc]/[sFGFR2-Fc]max [sFGFR2-Fc] found in plasma 6-hour post i.v. injection [sFGFR2-Fc]max found for SC#11 | 55% | 100% | | | | 81% | 45% | lofetuin, but not fetuin, is known to bind to the hepatic asialoglycoprotein receptor (ASGPR) (Webster et al., 2003, *Xenobiotica* 33:945)

Taken together, these results indicate that specific binding to asialoglycoprotein receptor via exposed terminal galactose residues from N-glycan are responsible for clearance of sFGFR2-Fc whereas the presence of one sialic acid per N-glycan on sFGFR2-Fc decreased significantly this clearance.

Example 2

Figure 5:
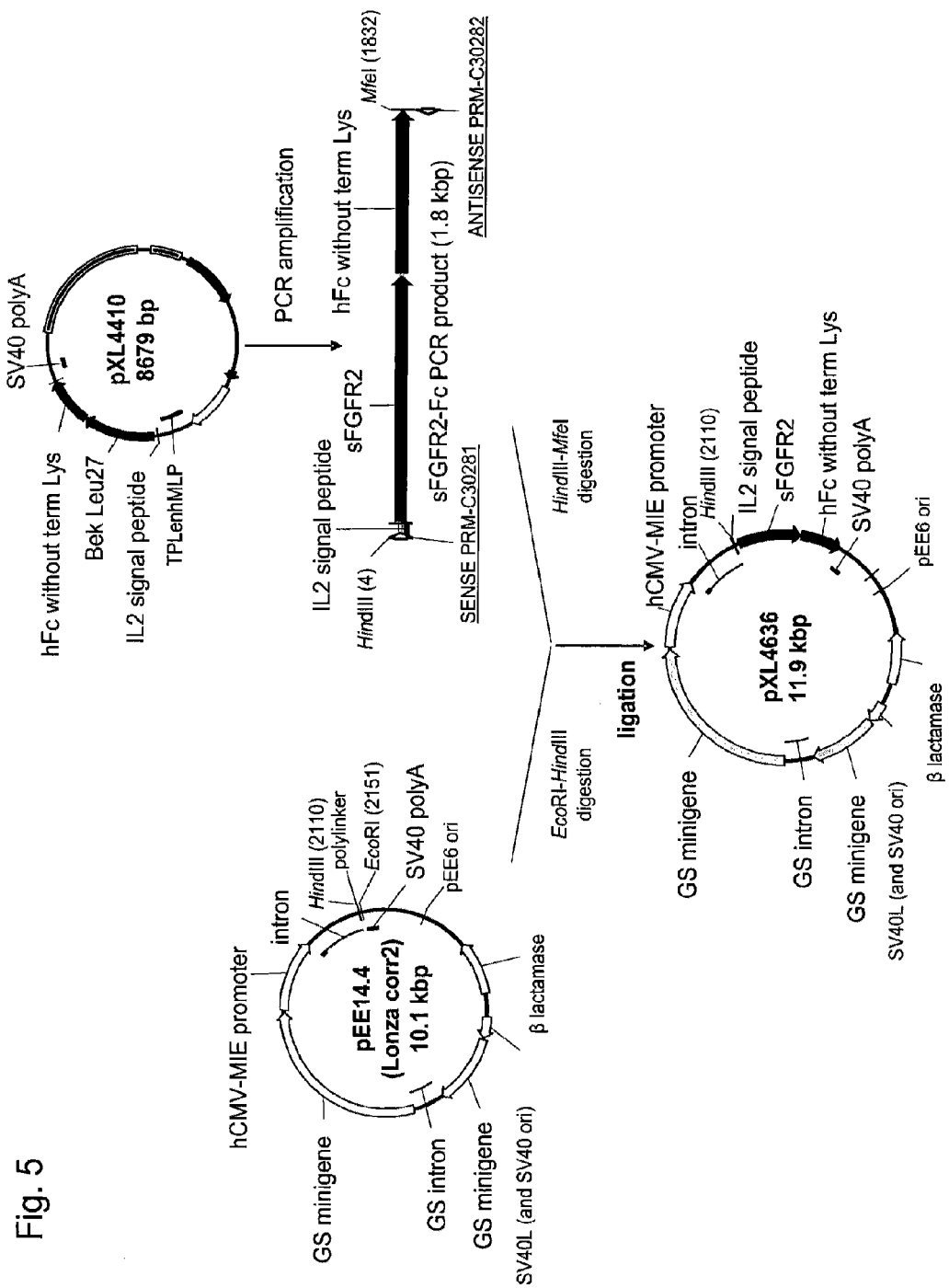
FIG. 5 is a schematic representation of the strategy used for constructing pXL4636, encoding sFGFR2-Fc and Glutamine Synthetase FIGS. 6 A and B show maps of the expression vectors pXL4429 for sFGFR2-Fc and DHFR and pXL4417 encoding neomycin resistance gene

Screening of CHO Stable clones expressing sFGFR2-Fc Protein with an Average Number of Sialic Acid Residues Per FGFR2 N-Glycan Greater than 1.2 for Optimal Pharmacokinetics Mammalian expression plasmid pXL4636 for stable expression of sFGFR2-Fc in CHO cells was generated from plasmid pEE14.4 encoding glutamine synthetase selection marker (Lonza) and plasmid pXL4410 containing the cDNA sequence encoding sFGFR2-Fc, FIG. 5. Plasmid pXL4636 was introduced into CHO K1 cells by nucleofection utilizing AMAXA cell line Nucleofactor kit as recommended by the supplier. Transfected cells were transferred into selective medium and after cell amplification the seven best producer The screening of clones based on high sialylated N-glycan of sFGFR2-Fc is predictive of optimal pharmacokinetics parameters of sFGFR2-Fc.

Example 3

Figure 6A:
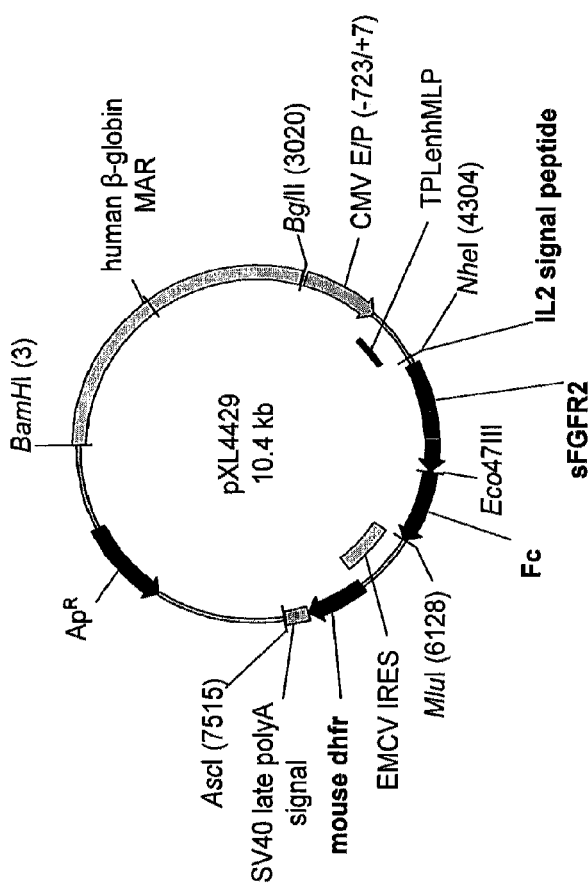
Figure 6B:
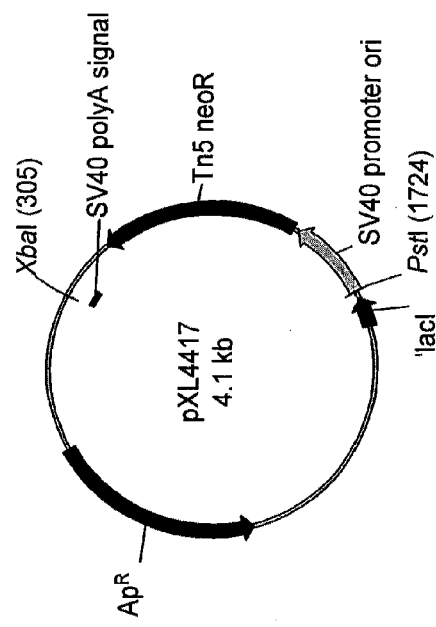

Correlation Between the Average Number of Sialic Acid Per sFGFR2-Fc N-Glycan and the Clearance of sFGFR2-Fc in Blood In other experiment similar to the experiment described in Example 2, stable CHO/DHFR clones expressing sFGFR2-Fc were generated using the DHFR selection and amplification system with the appropriate mammalian expression plasmids pXL4429 and plasmid pXL4417 (FIG. 6). These CHO-DHFR clones have also been screened for the content of sialic acid per sFGFR2-Fc molecule and the clearance of sFGFR2-Fc produced by these clones was also assayed.

Figure 7:
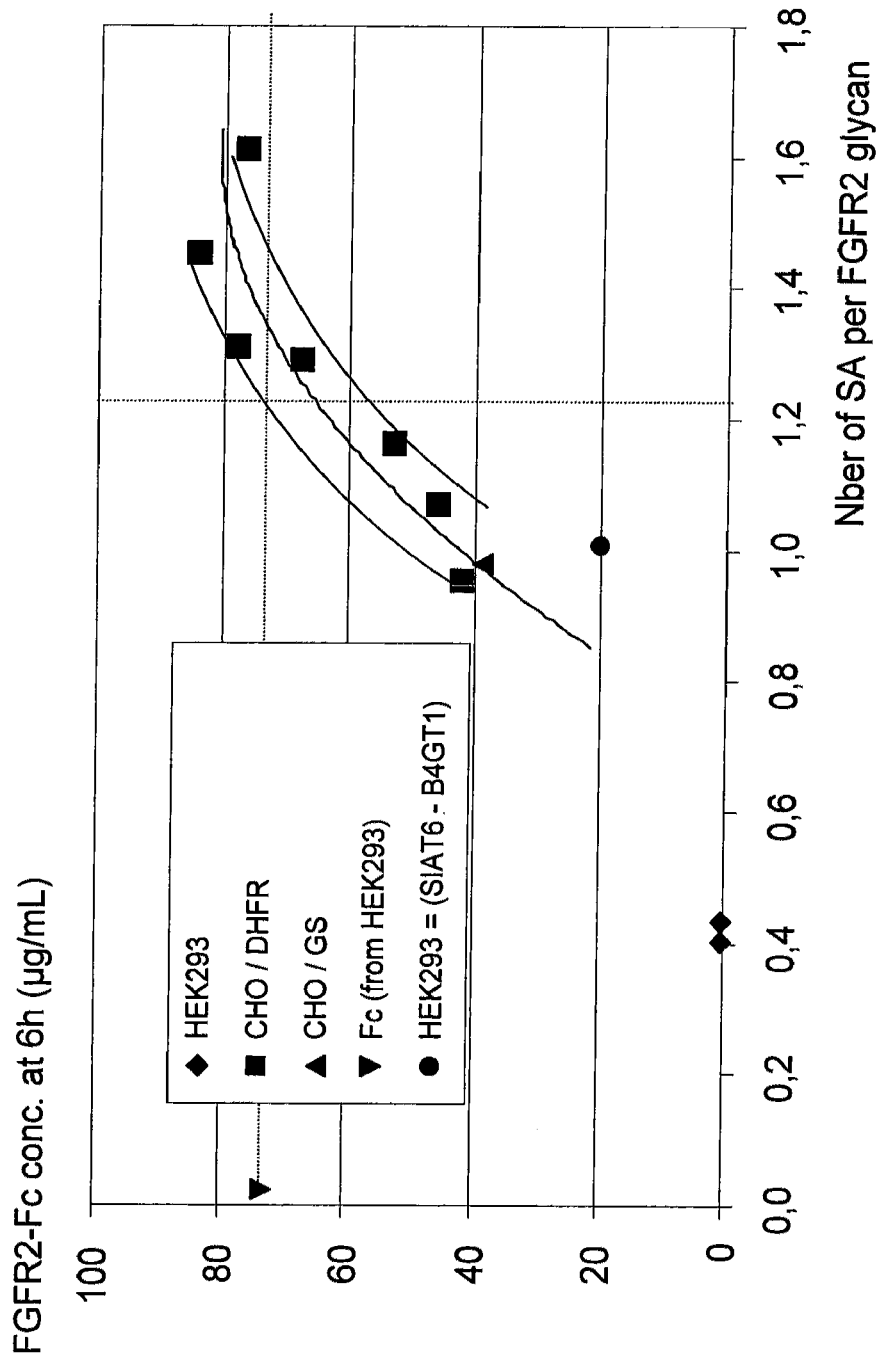
FIG. 7 is a graph showing the correlation between the average number of sialic acid per sFGFR2 N-glycan and clearance of sFGFR2-Fc in blood—Optimal ratio>1.2. preferred ratio>0.9.

The average number of sialic acid per N-glycan in the FGFR2 domain was calculated based on the total amount of moles of N-glycan per mole of FGFR2-Fc and the moles of N-glycan per Fc mole obtained after release of the Fc by papain. The results presented on FIG. 7 showed that a ratio of sialic acid residues per FGFR2 N-glycan greater than 1.2 ensured optimal sFGFR2-Fc concentration in the blood as compared to the optimal concentration in the blood found for Fc molecules. Only the selected clones reached this optimal ratio.

Therefore screening clones by the ratio of sialic acid residues per FGFR2 N-glycan allows the skilled person to predict the low clearance of sFGFR2-Fc in blood.

Example 4

Amino Acid Sequence of the sFGFR2-Fc Fusion Protein

The protein sFGFR2-Fc encoded by plasmid pXL4410 or pXL4636 or pXL4429 (FIGS. 5 and 6) is a fusion protein of the soluble FGFR2 human sequence with the Fc fragment derived from the human IgG1 sequence.

The sequence of the polynucleotide encoding sFGFR2-Fc is set forth in SEQ ID NO: 1 and in FIG. 4A. Likewise, the full amino acid sequence of the sFGFR2-Fc protein is set forth in SEQ ID NO: 2 in FIG. 4B. Amino acids from positions 1 to 350 correspond to the FGFR2IIIc isotype (see FIG. 4 C SEQ ID; NO: 4) and are the amino acids from position 27 to 376 described in SwissProt (FGFR2_HUMAN). Amino acids from positions 354 to 584 are amino acids of IgG1 from position 99 to 329 as described in SwissProt (IGHG1_HUMAN); see FIG. 4 D and SEQ ID NO: 6. Amino acids from positions 351 to 353 are amino acids of a synthetic linker: SAL (Ser Ala Leu) see FIG. 4 E.

Example 5

Defined N-Glycan Content of sFGFR2-Fc Produced in CHO Stable Clone GC111

Conditions have been optimized to produce sFGFR2-Fc such that the ratio of sialic acid residues per sFGFR2 N-glycan would be higher than 1.2. This example provides conditions to reach this condition.

A 5-L Celligen bioreactor (New Brunswick) filled with 4.4 L of CD-CHO protein-free media, supplemented with 100 µM MSX and 1×GS supplements was seeded at an initial cell density of $3.5 \times 10^5$ cells/mL of clone GC111 and cultured at 37° C. Sparger aeration was employed using a mixture of oxygen, nitrogen, air and carbon dioxide or pur oxygen, and dissolved oxygen was maintained at 30% of air saturation. The pH was maintained at 7.2 by addition of carbon dioxide and injection of 1 M sodium bicarbonate in the culture medium. The agitation rate used was 110 rpm using a Cell Lift Impeller. The feed solution (450 g/L glucose) was continuously fed to maintain the glucose at a target level of 2-3 g/L. Feeding was started at day 5 when residual glucose concentration reached 2.5 g/L. Continuous nutrient feeding was based on the predicted cell growth and glucose consumption with a nutrient feeding rate equal to the glucose consumption rate. The glutamate concentration was maintained at 1-3 mmol/L by pulse addition following daily off-line control. The cell culture was monitored for cell count, viability and metabolites (glucose, lactate, glutamine, ammonia and glutamate) and for product concentration during the production phase. The culture was stopped when cell viability dropped down to 55%, and the culture harvest was collected.

The cell culture harvest was clarified and sFGFR2-Fc was purified by affinity chromatography (ProsepvA, Millipore) and two ion-exchange chromatography steps then filtered sterile and stored in phosphate buffer saline before further analysis and in vivo testing.

The apparent molecular mass of sFGFR2-Fc obtained from SDS-PAGE analysis under non-reducing conditions was 180 kDa. This was in contrast with the theoretical molecular mass of 130 kDa calculated based on the amino acid sequence of the sFGFR2-Fc homodimer. This large difference between apparent and calculated molecular masses was attributed to the additional presence of about 30% of N-glycans, see Table 3. Indeed upon digestion of the sFGFR2-Fc by Peptide-N-glycosidase F (PNGase F, Roche) followed by analysis by SDS-PAGE under non-reducing conditions, the molecular mass of deglycosylated sFGFR2-Fc was around 160 kDa (FIG. 7).

The carbohydrate composition and the N-glycan profile of sFGFR2-Fc was analyzed as described on Example 1 and reported on Table 3.

TABLE 3

| Carbohydrate composition and N-glycan profile of sFGFR2-Fc produced in optimal conditions | |
|---|---|
| Expressed protein from stable CHO-GS clone GC111 | sFGFR2-Fc |
| % sFGFR2-Fc sialylated species: | |
| 1-non sialylated | 30% |
| 2-Monosialylated | 34% |
| 3-Disialylated | 23% |
| 4-trisialylated | 13% |
| Average number of sialic acid per sFGFR2 N-glycan | 1.34 |
| Monosaccharide composition of sFGFR2-Fc N-glycans per 3 mannoses | |
| 1-Glucosamine (number per 3 mannoses) | 4.9 |
| 2-Galactose (number per 3 mannoses) | 2.7 |
| 3-Fucose (number per 3 mannoses) | 0.96 |
| Fucose composition of Fc N-glycan per 3 mannoses | 1.1 |

Compared to the results obtained on Table 2, sFGFR2-Fc, produced from clone GC111 in the optimal conditions, had more sialylated N-glycan than sFGFR2-Fc produced from the semi-clone SC#118, parent of clone GC111 produced in standard conditions. For example the % of non-sialylated species decreased from 43% to 30%.

Based on the total amount of moles of N-glycan per mole of FGFR2-Fc and the moles of N-glycan per Fc mole obtained after release of the Fc by papain, it was measured that there were seven N-glycans per FGFR2. Therefore most the sites of the FGFR2 domain are almost all fully occupied.

Example 6

N-Glycosylation Sites Important for FGF Affinity and Productivity

Figure 8:
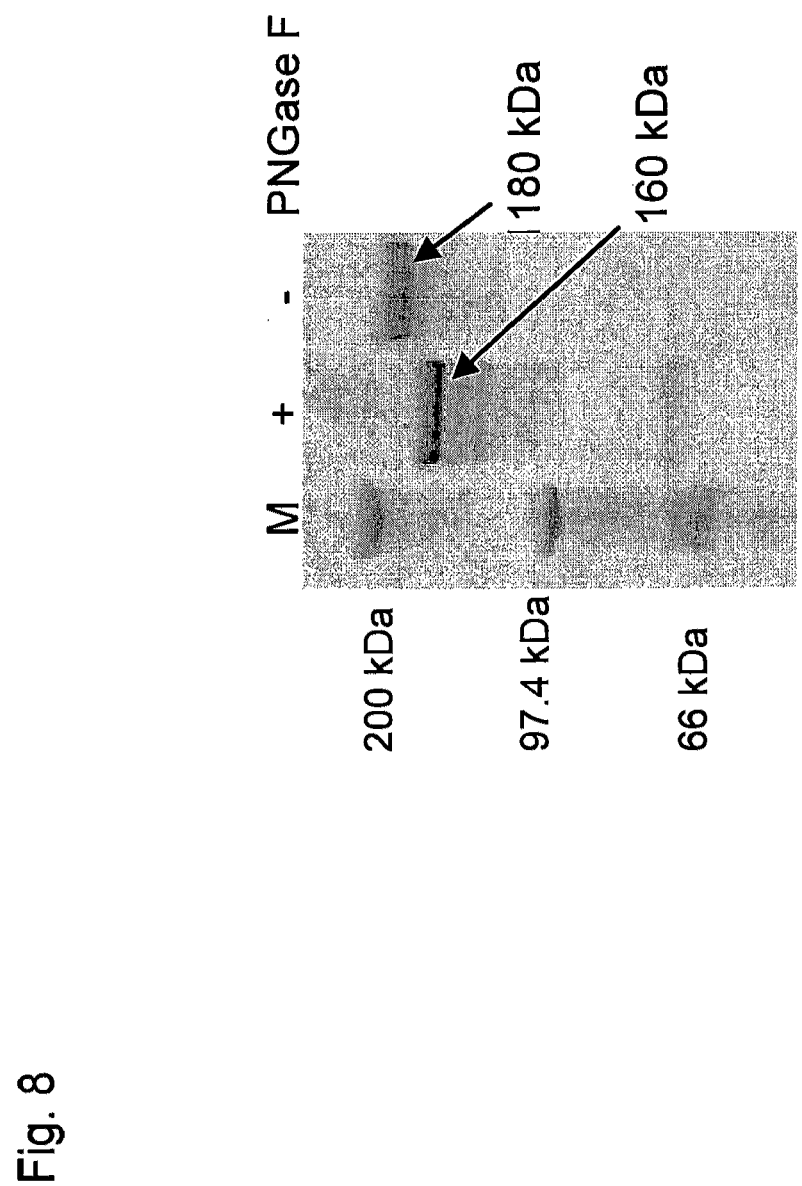
FIG. 8 shows SDS-PAGE (non reducing conditions) of 1 µg of sFGFR2-Fc incubated in the absence (−) or in the presence (+) of PNGase F. M: molecular weight marker

The sFGFR2-Fc fusion protein has eight N-glycosylation sites in the FGFR2 domain and one in the Fc domain, see FIG. 8 and Table 5 for definition of N-glycan positions N1 to N8. Proteins 4493 and 4565, two variants of sFGFR2-Fc no longer having Ig-like domain 1, were produced. 4493 exhibited characteristics similar to wild type FGFR2-Fc derived from pXL4636 in terms of productivity and binding to FGF-2 or heparin. In contrast, 4565 in which all glycosylation sites in the sFGFR2 domain were mutated (N- to Q substitution) could not be characterized due to the more than 50-fold reduction in productivity of the mutant, see Table 4.

TABLE 4

Physico-chemical characteristics of sFGFR2-Fc variants

| Protein ID | N-Glycosylation sites in FGFR2 domain | Amino acid residue at N-glycosylation site | Production (mg/L) | FGF-2 binding $K_D$ ($10^{-9}$M) | Heparin binding [NaCl] for elution from heparin (mM) |
|---|---|---|---|---|---|
| 4410 | 8 (N1 to N8) | N | 75 | 1.39 | 370 |
| 4493 | 6 (N3 to N8) | N | 67 | 1.19 | 442 |
| 4565 | 6 (N3 to N8) | Q | <1 | ND | ND |

** Binding to FGF-2 was determined on a BIAcore ™ instrument utilizing a "two-state reaction with conformation change" model as described by Gamsjaeger et al., Biochem. J. 7 Apr. 2005/BJ20050156. In brief, integration was performed on the entire sensogram except in the "bulk effect" areas. Concentration range was selected between 1 to 8 nM. The simultaneous ka/kd kinetics method allows the measurements of two ka and two kd assuming the following equations:

ka1 and kd1 for A + B ⇌ AB ka2 and kd2 for AB ⇌ AB* that may represent dimerization of (FGF - FGFR2-Fc) complexes The dissociation constant $K_D$ was calculated from the following formula:

$$\frac{1}{(ka_1/kd_1) \times (1 + ka_2/kd_2)}.$$

According to the two competing models reported (the symmetric two-end model from Mohammadi and the asymmetric model from Pellegrini), sites N3 to N7 could potentially interact with amino acid residues of either FGF1 or FGFR2c and/or interact with heparin, whereas site N8 is unlikely to be involved in interactions in all crystal structures (Pellegrini et al. 2000. *Nature* 407: 1029; Ibrahimi et al. 2005 *Mol. Cell. Biol.* 25: 671).

Based on the above information, it was relevant to study the N-glycosylation sites at positions N3 to N7 by substitution of the corresponding Asn to Gln and by keeping position N8 unchanged to allow for significant productivity. The positional influence of N-glycans on physico-chemical characteristics of sFGFR2-Fc was evaluated statistically with a two-level fractional factorial experiment. Five variables (glycosylation site occupancy at positions N3 to N7) were selected and 16 independent constructs were studied. The experimental $2^{5-1}$ fractional design and data analysis were performed as described (Statistics for Experimenters, G. Box Ed., Willey, 1978).

Fractional Factorial Design

Site-specific N-glycosylation variants were designed based on 4493 and the factorial design at two levels with five variables (N3 to N7) that could either be at a plus level (N) or a minus level (Q). The design was fractional with 16 constructs ($2^{5-1}$, i.e. resolution V design), allowing the identification of the main effects and of 2-factor interactions but confounding 2-factor with 3-factor interactions.

The 16 plasmid constructs were obtained by sequential PCR and cloning to generate the N to Q substitution at position N3, N4, N5, N6 or N7 but keeping position N8 and the N-glycosylation site of the Fc domain unchanged. These protein variants only differed from 4493 by the 2- or 4-point mutations listed on Table 5.

TABLE 5

Design matrix

Figure 9:
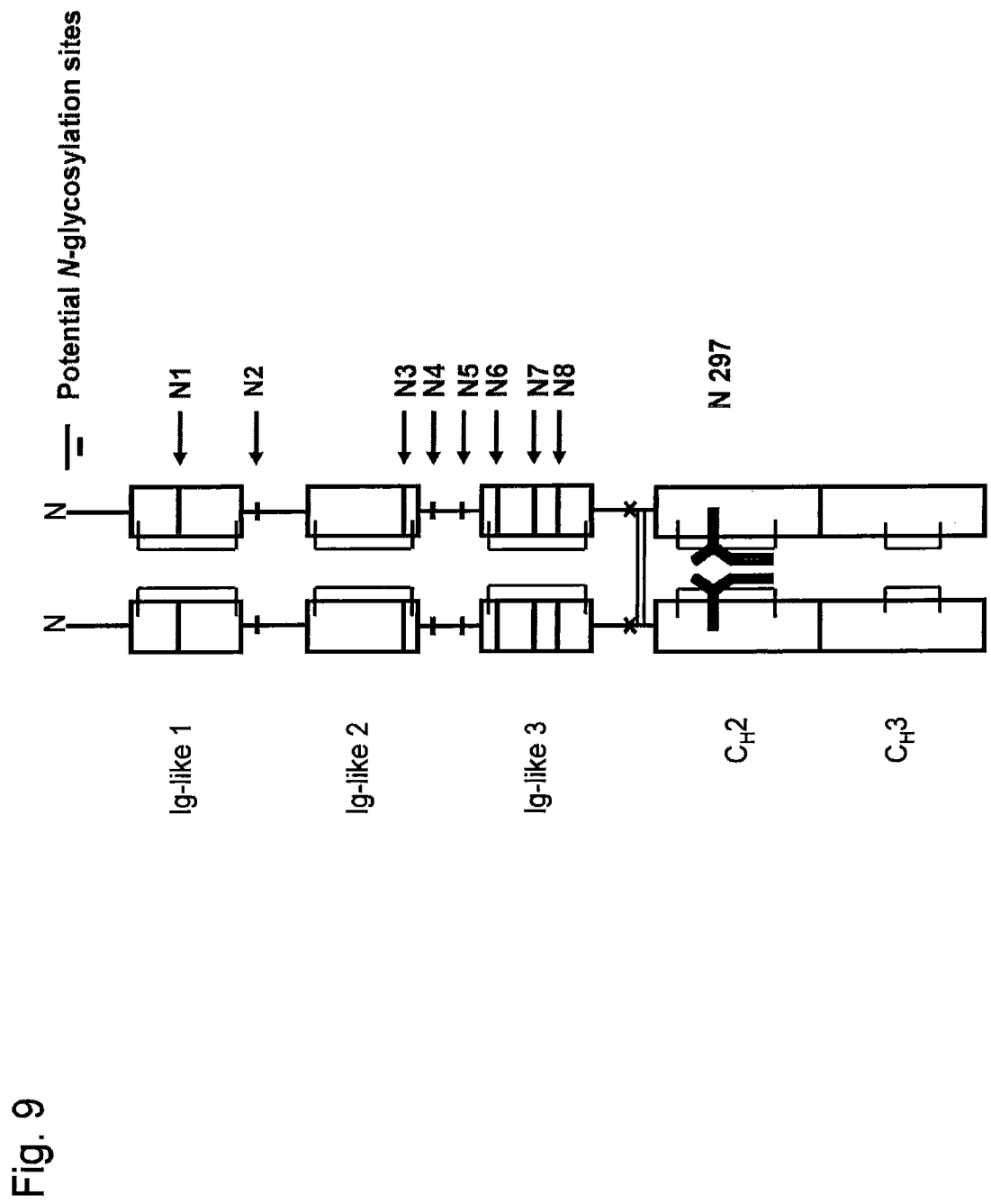
FIG. 9 shows the N-glycan position and numbering in sFGFR2-Fc dimer. The numbering starts from the N-terminal amino acid sequence of FGFR2 (FGFR2HUMAN) such that position N1 correspond to Asn83, N2 to Asn123, N3 to Asn228, N4 to Asn241, N5 to Asn 265, N6 to Asn 297, N7 to Asn318, N8 to Asn331. Position N297 correspond to the Asn position on human Fc (IgG1).

| | N-glycosylation position status Asn position on FIG. 9 | | | | | | |
|---|---|---|---|---|---|---|---|
| | N3 | N4 | N5 | N6 | N7 | N8 | N 297 (Fc) |
| | Asn position on FGFR2_HUMAN | | | | | | |
| Construct | 228 | 241 | 265 | 297 | 318 | 331 | |
|---|---|---|---|---|---|---|---|
| 4572 | − | − | − | − | + | + | + |
| 4570 | + | − | − | − | − | + | + |
| 4577 | − | + | − | − | − | + | + |
| 4571 | + | + | − | − | + | + | + |
| 4587 | − | − | + | − | − | + | + |
| 4585 | + | − | + | − | + | + | + |
| 4586 | − | + | + | − | + | + | + |
| 4573 | + | + | + | − | − | + | + |
| 4574 | − | − | − | + | − | + | + |
| 4575 | + | − | − | + | + | + | + |
| 4588 | − | + | − | + | + | + | + |
| 4576 | + | + | − | + | − | + | + |
| 4579 | − | − | + | + | + | + | + |
| 4569 | + | − | + | + | − | + | + |
| 4578 | − | + | + | + | − | + | + |
| 4493 | + | + | + | + | + | + | + |

The 16 designed constructs were tested for production at small scale. Two variants (4572 and 4574) were very low producers (around 2 mg/L). The remaining 14 constructs were produced at liter-scale and purified in parallel under standard conditions with reasonable product recovery. They were then analyzed by SDS-PAGE, gel filtration, BIAcore™. Results were analyzed with the statistical fractional factorial resolution—$2^{5-1}$ DOE.

Productivity

N-glycosylation at N3, N4, N5, N6, N7 had a positive contribution on productivity. There was a similar quantitative effect for all the positions studied (i.e. N3, N4, N5, N6 and N7) and no significant effect of two-factor interactions.

TABLE 6

Productivity

| Construct | Titer (mg/L) from production at 1-L | Response (mg/L) | Variable |
|---|---|---|---|
| 4572 | 0 | 28 | Mean |
| 4570 | 13 | 17 | N3 |
| 4577 | 9 | 14 | N4 |
| 4571 | 34 | 20 | N5 |
| 4587 | 5 | 13 | N6 |
| 4585 | 40 | 13 | N7 |
| 4586 | 42 | −8 | N3-N4 |
| 4573 | 32 | 3 | N3-N5 |
| 4574 | 0 | 1 | N3-N6 |
| 4575 | 30 | −2 | N3-N7 |
| 4588 | 37 | −2 | N4-N5 |
| 4576 | 27 | −1 | N4-N6 |
| 4579 | 30 | 6 | N4-N7 |
| 4569 | 54 | 4 | N5-N6 |
| 4578 | 37 | 0 | N5-N7 |
| 4493 | 67 | −1 | N6-N7 |

Aggregation

Purified proteins were analyzed by gel filtration (Superdex 2000) to quantitate the percentage of high molecular weight species (HMW; %) in purified preparations. The highest value (worst-case) of 80.2% HMW was obtained for 4587 and was used in the DOE analysis for the two constructs (4572 and 4574) that could not be produced (the mean percentage of HMW value obtained from the 14 constructs was also used for comparison, giving a similar conclusion). N-glycosylation at position N5 and to a lesser extent at position N6 disfavored the appearance of HMW species. The N5-N6 interaction exhibited a similar effect on aggregation.

TABLE 7

Aggregate formation

| Construct | HMW (%) | Response (%) | Variable |
|---|---|---|---|
| 4572 | 80 | 57 | Mean |
| 4570 | 73.0 | −12 | N3 |
| 4577 | 71.6 | −5 | N4 |
| 4571 | 72.1 | −33 | N5 |
| 4587 | 80.2 | −18 | N6 |
| 4585 | 47.5 | −7 | N7 |
| 4586 | 47.7 | 6 | N3-N4 |
| 4573 | 57.5 | −8 | N3-N5 |
| 4574 | 80 | −5 | N3-N6 |
| 4575 | 69.6 | 2 | N3-N7 |
| 4588 | 71.8 | −2 | N4-N5 |
| 4576 | 72.9 | 3 | N4-N6 |
| 4579 | 35.2 | −4 | N4-N7 |
| 4569 | 12.0 | −18 | N5-N6 |
| 4578 | 39.4 | −6 | N5-N7 |
| 4493 | 3.6 | 1 | N6-N7 |

Binding to FGF-2

The binding affinity to FGF-2 was determined with BIAcore™ for each construct. Dissociation constant ($K_D$) values between 0.49 and 2.31 nM were obtained for constructs showing measurable affinity. For constructs that did not bind to FGF-2 or could not be produced, a value of 10 nM was used for the DOE analysis. N-glycosylation at positions N5 and to a lower extent at positions N6 and N3 had a positive effect on binding to FGF-2. Interactions N3-N5 & N5-N6 had a significant positive effect on binding whereas interactions N3-N6 and N4-N7 had a negative effect on binding.

TABLE 8

Binding to FGF-2

| Construct | $K_D$ (nM) | Response(nM) | Variable |
|---|---|---|---|
| 4572 | 10 | 6.8 | Mean |
| 4570 | 10 | −2.2 | N3 |
| 4577 | 10 | −0.5 | N4 |
| 4571 | 10 | −6.5 | N5 |
| 4587 | 10 | −2.3 | N6 |
| 4585 | 2.7 | 0.5 | N7 |
| 4586 | 10 | 0.0 | N3-N4 |
| 4573 | 0.49 | −2.2 | N3-N5 |
| 4574 | 10 | 2.0 | N3-N6 |
| 4575 | 10 | 0.1 | N3-N7 |
| 4588 | 10 | −0.5 | N4-N5 |
| 4576 | 10 | 0.1 | N4-N6 |
| 4579 | 2.31 | 2.0 | N4-N7 |
| 4569 | 0.99 | −2.3 | N5-N6 |
| 4578 | 0.66 | 0.5 | N5-N7 |
| 4493 | 1.19 | 0.0 | N6-N7 |

This resolution-V $2^{5-1}$ D.O.E. revealed that N-glycosylation had a positive contribution on productivity, at positions N3, N4, N5, N6, N7; had a positive impact on binding to FGF-2, at positions N5>>N6 and N3; and disfavored the appearance of high molecular-weight molecules at all positions, especially N5>N6.

Therefore N-glycan occupancy is mandatory at position N5, and recommended at positions N3, N4, N6 and N7 respectively (position 265, 228, 241, 297 and 318 respectively on FGFR2_HUMAN (Swissprot).

Example 7

Pharmacokinetics of sFGFR2-Fc Fusion Protein

Figure 10:
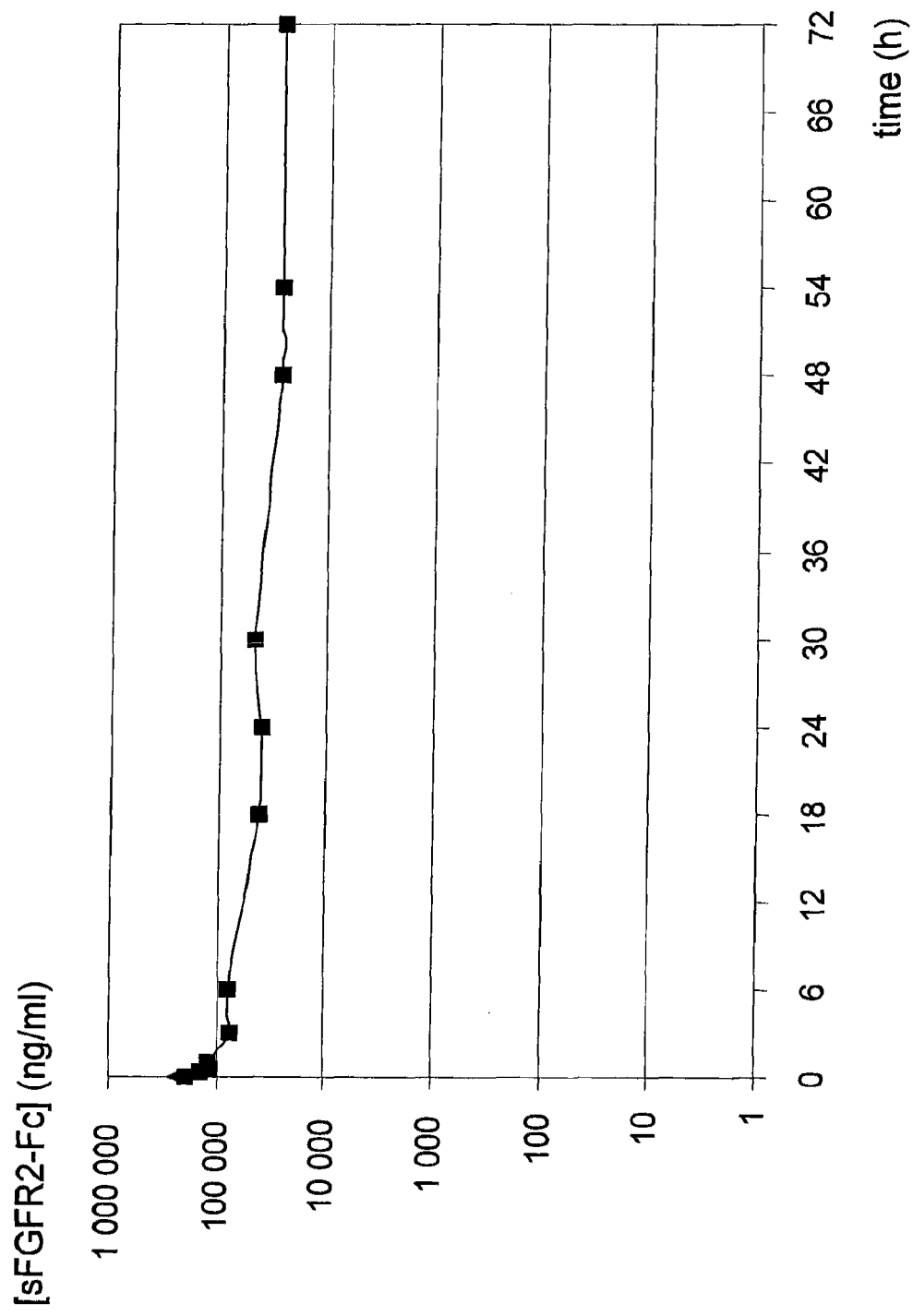
FIG. 10 is a graph showing the kinetics of disappearance of protein sFGFR2-Fc (squares) in blood over time up to 72 hours.
Figure 11:
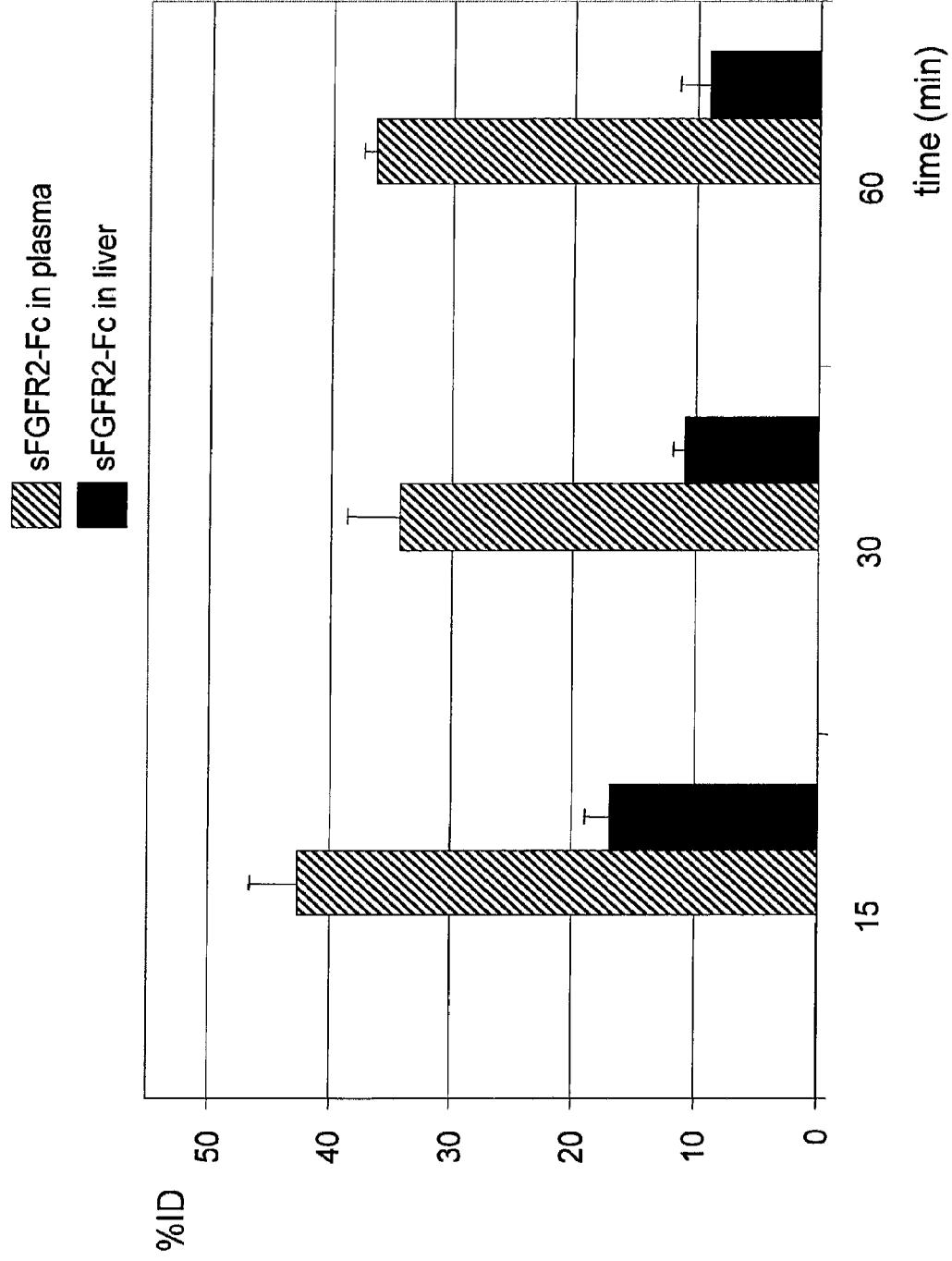
FIG. 11 shows the amount of recoveries of protein sFGFR2-Fc in plasma and liver expressed in % of injected dose.

In example 7, sFGFR2-Fc is the fusion protein corresponding to amino acid sequence SEQ ID No. 2 with an average number of sialic acid per sFGFR2 N-glycan of 1.3. Three mice per time point were injected with 500 µg of the fusion protein in the tail vein. At various time points after injection of the product, blood was collected, FIG. 10 shows protein concentration in plasma and liver. FIG. 11 shows the amount of protein recovery at early time points in plasma and liver expressed in percentage of injected dose.

Pharmacokinetic parameters were calculated using non-compartmental analysis. Elimination half-life was calculated with the last 6 data points that provided the best fit of the log-linear terminal phase (Table 9).

TABLE 9

| Parameter | Units | sFGFR2-Fc |
|---|---|---|
| t½ | hr | 70.1 |
| Tlast | hr | 72.0 |
| Clast | µg/mL | 27.6 |
| AUClast | hr*µg/mL | 3138 |
| Clobs | mL/hr/kg | 4.2 |
| Vss | mL/kg | 406 |

| | |
|---|---|
| AUClast | Area under the curve from the time of dosing to the last measurable concentration. |
| Clobs | Total body clearance for extravascular administration |
| Clast | Concentration corresponding to Tlast |
| t½ | Terminal half-life |
| Tlast | Time of last measurable (non-zero) concentration. |
| Vss | an estimate of the volume of distribution at steady state |

Following intravenous administration, sFGFR2-Fc showed a favorable pharmacokinetic profile with a long elimination half-life (almost 3 days) and a reduced total body clearance. The volume of distribution was limited and lower than total body water volume, suggesting limited tissue distribution. At 72 h, sFGFR2-Fc plasma concentration stays at a very high concentration and clearance is also good.

Pharmacokinetic parameters of sFGFR2-Fc are very compatible with the use of this fusion protein as a therapeutic. In effect as shown in the Examples, plasma concentration after intravenous injection in mice is substantially high, and clearance stays very low at 72 h after injection. Importantly, the kinetics of sFGFR2-Fc cleavage in vivo is also very low, since the sFGFR2-Fc was only partially cleaved (40% after 18 h) and the full-length molecule concentration remained unchanged until 72 h. Therefore, the fusion molecule, as listed in SEQ ID NO: 2 and an average number of sialic acid per sFGFR2 N-glycan of 1.3, showed a favorable pharmacokinetic profile with a long elimination half-life (almost 3 days) and a satisfactory total body clearance.

Example 8

Efficacy of the sFGFR2-Fc Fusion Protein in A549 Subcutaneous Tumor Model

In this example, sFGFR2-Fc is the fusion protein corresponding to amino acid sequence SEQ ID No. 2 with an average number of sialic acid per sFGFR2 N-glycan of 1.3. A549 Subcutaneous Tumor Model A549 cells line had been identified as a tumor cell line to assess the efficacy of sFGFR2-Fc. It has been demonstrated in vitro by the Applicant that this cell line expresses FGF2 and also that sFGFR2-Fc can abrogate autocrine proliferation of these cells. A subcutaneous A549 tumor model was set up by the Applicant in Balb/c nude mice. Moreover the tumor in vivo expresses FGF2.

In this experiment, the efficacy of sFGFR2-Fc molecule was assessed on A549 tumor growth model. Products were injected subcutaneously twice a week. Different doses, i.e. 25, 15, and 5 mg/kg of the sFGFR2-Fc were assessed.

After overall analysis of tumor volume evolution of the three treated group with sFGFR2-Fc were statically different to the tumor evolution of the group treated with PBS. sFGFR2-Fc is efficient on tumor growth in this model at the dose of 5 mg/kg twice a week.

Experimental Design $5.10^6$ A549 cells in 200 µl were injected subcutaneous in Balb/c nude mice at day 0. After cell injection the same day, mice were randomized per block of 4 in four groups based on body weight. The treatments started after randomization the day after cell injection. Each group received subcutaneously 500, 300 or 100 µg/mouse/administration corresponding respectively to 25, 15 and 5 mg/kg, two times per week: Monday and Friday, during 39 days.

Results

Tumor Volume Analysis

Figure 12:
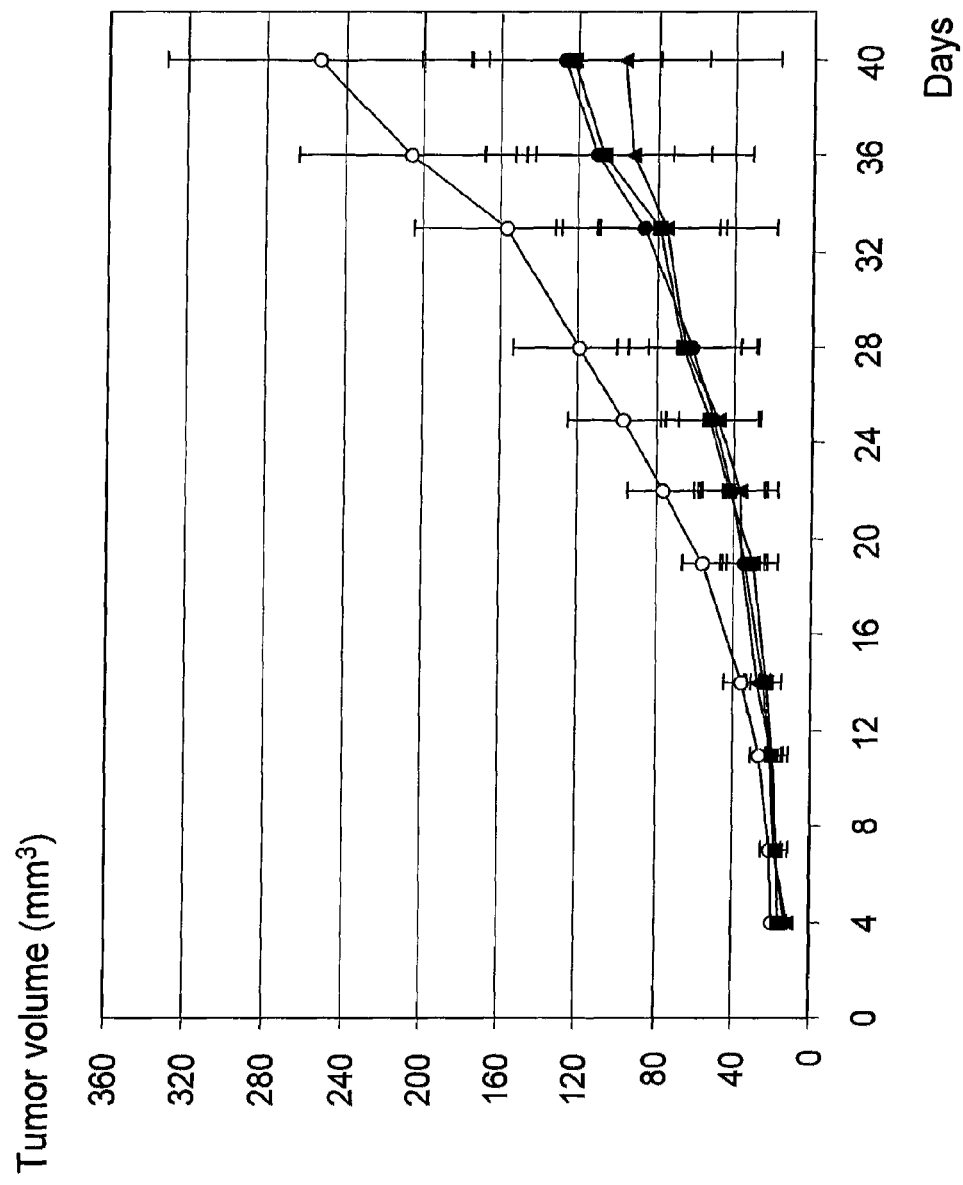
FIG. 12 is a graph of the A549 tumor volume analysis after treatment up to day 40 (100 µg/mouse/admin: triangles; 300 µg/mouse/admin: squares; 500 µg/mouse/admin: closed circles; PBS control: open circles).

As shown in FIG. 12, the volume of the tumor was analyzed up to day 40. The groups 100 µg (triangle), 300 µg (squares) and 500 µg/mouse/administration (closed circles) were statistically different from group PBS (open circles). We concluded that sFGFR2-Fc decreased tumor growth at the dose 25, 15 and 5 mg/kg.

Tumor Weight at Day 40

Figure 13:
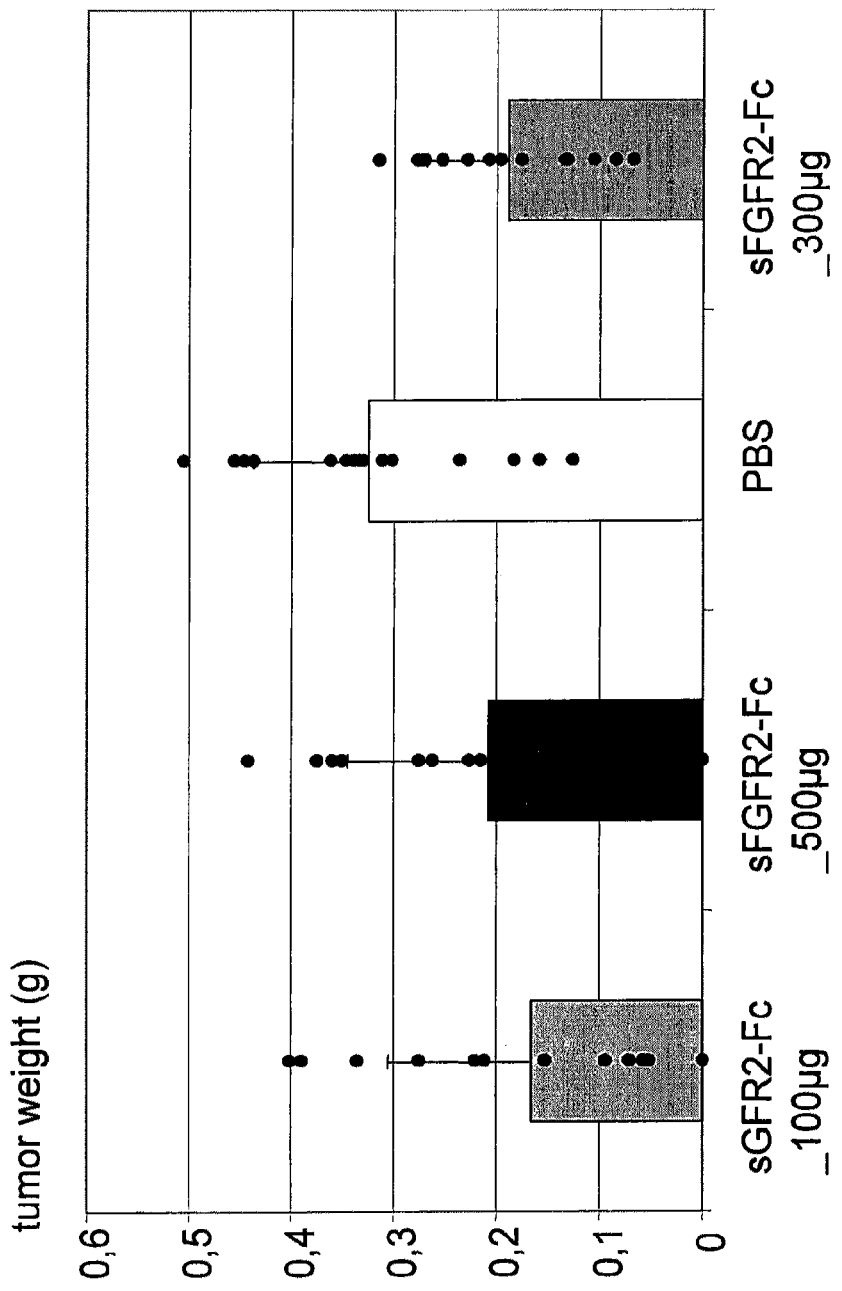
FIG. 13 is a graph of the A549 tumor weight analysis after treatment at day 40.

As shown in FIG. 13, the tumors were harvested and weighed at the end of the experiment. The groups 100 µg, 300 µg and 500 µg/mouse/administration were statically different to group PBS. We concluded that sFGFR2-Fc according to the present invention decreased tumor weight at the dose 25, 15 and 5 mg/kg.

Evolution of tumor growth of sFGFR2-Fc_100, sFGFR2-Fc_300 and sFGFR2-Fc_500 groups were statistically different to the evolution of the group treated with PBS. The sFGFR2-Fc fusion protein according to the present invention (amino acid sequence SEQ ID No. 2 with an average number of sialic acid per sFGFR2 N-glycan of 1.3, is able to substantially decrease tumor growth at the dose of 5 mg/kg.

Example 9

Efficacy of sFGFR2-Fc Fusion Protein in H460 Subcutaneous Tumor Model

In example 9, sFGFR2-Fc is the fusion protein corresponding to amino acid sequence SEQ ID No. 2 with an average number of sialic acid per sFGFR2 N-glycan of 1.6.

H460 Subcutaneous Tumor Model

H460 cells line had been identified as a tumor cell line to assess the efficacy of sFGFR2-Fc. It has been demonstrated in vitro that this cell line expresses FGF2. In this experiment the efficacy of sFGFR2-Fc was assessed on tumor growth. Products were injected subcutaneously twice a week at the dose of 25 mg/kg. After overall analysis of tumor volume evolution, sFGFR2-Fc decreased tumor growth.

Experimental Design $5.10^6$ H460 cells in 200 µl were injected subcutaneous in right flank of Balb/c nude mice at day 0. After cells injection, on the day of cell inoculation (Day 0) mice were randomized on the body weight measured and will be allocated to the treatments groups.

Treatments were administered twice a week by subcutaneously injections (200 µl) for 3 consecutive weeks (Monday and Friday). The first administration was performed on Day 1 after cell inoculation to maximize the exposure of the cells to the treatment.

Results

Tumor Volume Analysis

Figure 14:
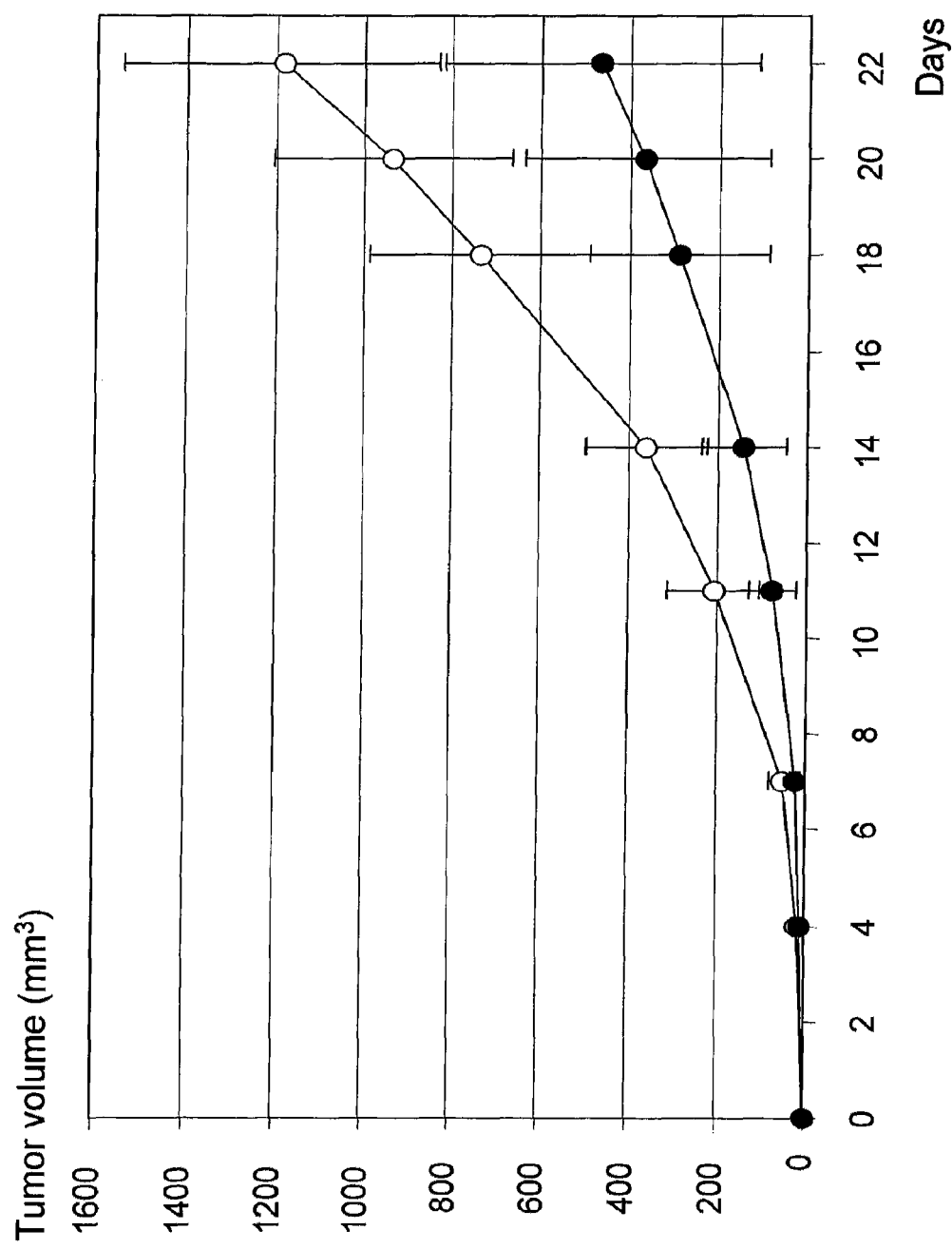
FIG. 14 is a graph of the H460 tumor volume analysis after treatment up to day 22 (treated group: closed circles; PBS control group: open circles).

FIG. 14 shows the tumor volume analysis up to day 22. We concluded that sFGFR2-Fc substantially decreased the tumor growth.

Tumor Weight Analysis

Figure 15:
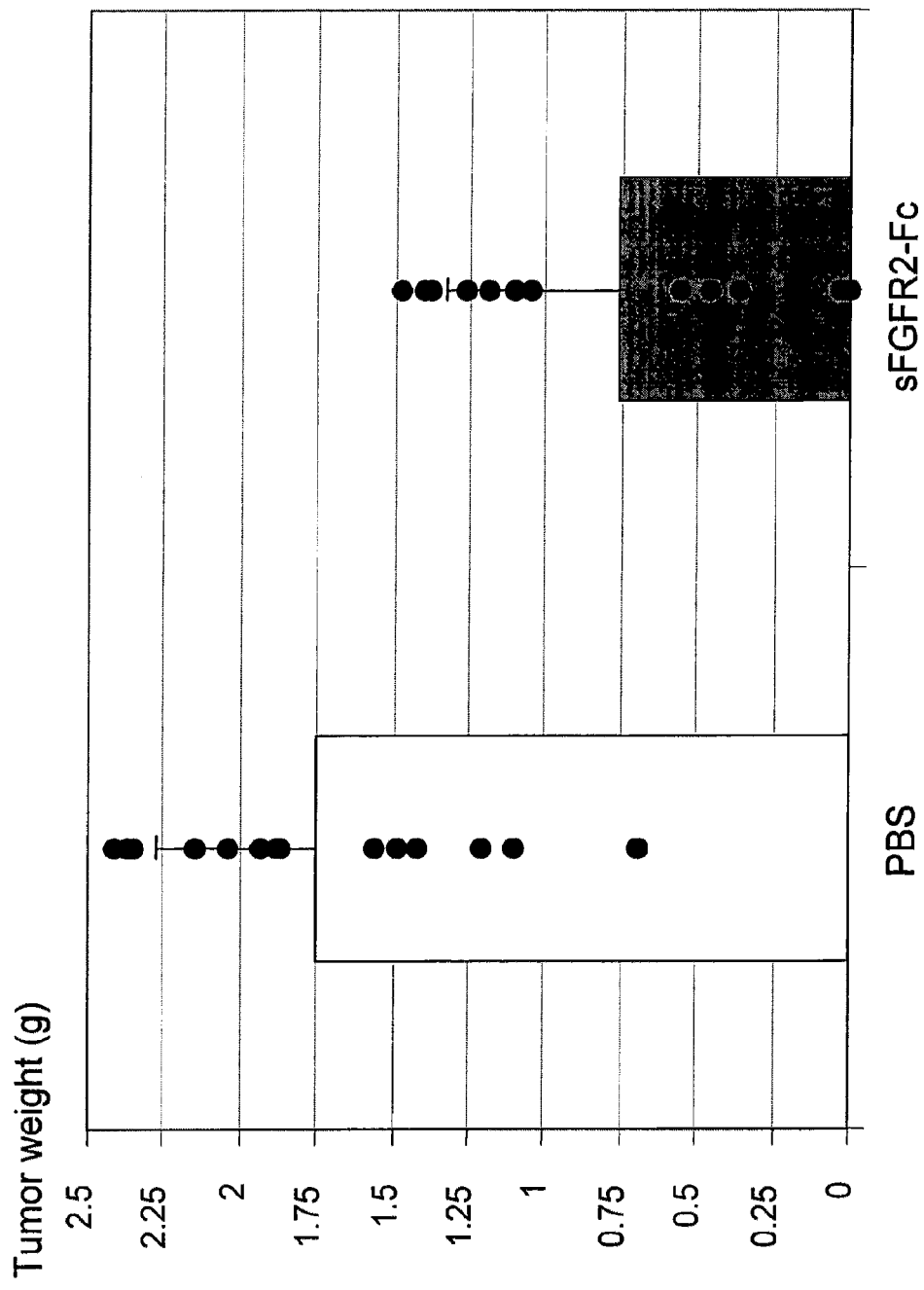
FIG. 15 is a graph of the H460 tumor weight analysis after treatment at day 22.

FIG. 15 shows the tumor weight analysis at day 22. We concluded that sFGFR2-Fc substantially decreased the tumor weight.

Evolution of tumor growth of sFGFR2-Fc group was statically different of evolution of group treated with PBS. We clearly concluded that the fusion protein according to the present invention (amino acid sequence SEQ ID No. 2 with an average number of sialic acid per sFGFR2 N-glycan of 1.6 is able to substantially decrease H460 tumor growth at the dose of 25 mg/kg.

Example 10

Evaluation of In Vitro ADCC Activity of sFGFR2-Fc Fusion Protein on A549 and H460 Cell Lines In this example sFGFR2-Fc is the fusion protein corresponding to amino acid sequence SEQ ID No. 2 with an average number of sialic acid per sFGFR2 N-glycan greater than 1.6. The capacity of sFGFR2-Fc to mediate an in vitro ADCC activity has been evaluated in both selected models H460 and A549 tumor cells (see examples 8 and 9).

Experimental Design

Tumor cells (A549 and H460) in PBS 2% BSA (1 million/mL) have been incubated 30 min at 4° C. with 500 ng/mL of FGF2 (R&DSystems) and 2 µg/mL of sFGFR2-Fc or control human IgG1 (Sigma). Tumor cells have been diluted in RPMI 1% FBS and incubated in 96-well plate at 5000 cells per well. Purified NK have been added in ratio NK/tumor cells 20/1 and 6/1. Plates have been incubated 4 hours at 37° C., then centrifuged and lactate dehydrogenase has been titrated in the supernatant (kit ROCHE). 100% lysis was obtained using triton X100 0.2%. Specific sFGFR2-Fc induced ADCC was calculated as required by the manufacturer.

Results

Figure 16:
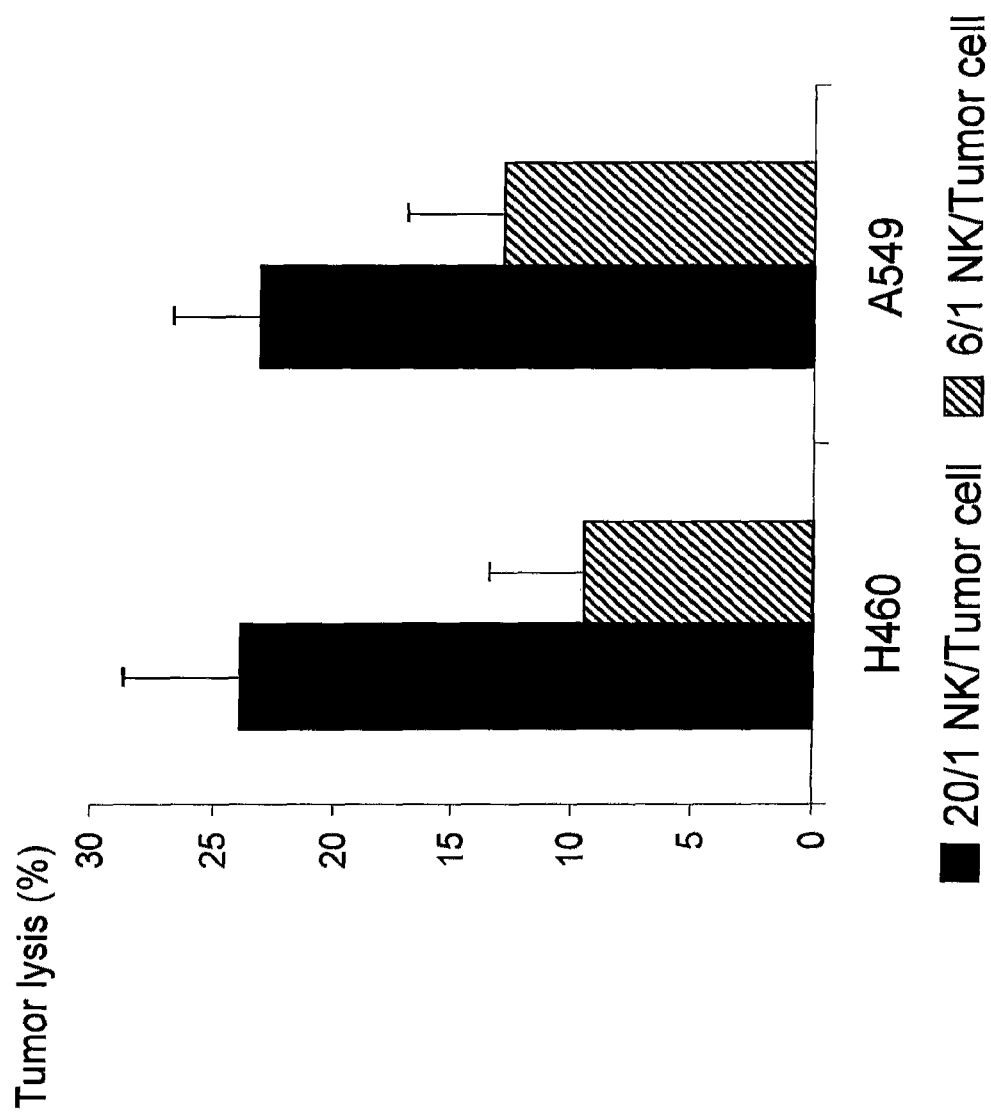
FIG. 16 is a graph of the evaluation of the in vitro ADCC activity of sFGFR2-Fc on H460 and A549 tumor cells.

The results illustrated on FIG. 16, show a tumor cell lysis mediated by natural killer cells (NK) in the presence of sFGFR2-Fc on both A549 and H460 tumor cells close to 25% in the 20/1 (NK/tumor cell) conditions, indicating that sFGFR2-Fc is able to mediate ADCC effect on these tumor cells.

Example 11

Evaluation of In Vivo ADCC and CDC Activities of sFGFR2-Fc Fusion Protein in A549 Subcutaneous Tumor Model In this example, sFGFR2-Fc is the fusion protein corresponding to amino acid sequence SEQ ID No. 2 with an average number of sialic acid per sFGFR2 N-glycan greater than 1.6.

A549 Subcutaneous Tumor Model

A549 cell line has been identified as a tumor cell line to assess the efficacy of sFGFR2-Fc, since these cells expressed high level of FGF2 in vivo and were sensitive to in vitro sFGFR2-Fc-mediated-ADCC.

Mouse Strains

Three different mouse strains (SCID, NOD/SCID and SCID/bg mice) were selected to evaluate the capacity of sFGFR2-Fc to mediate in vivo ADCC and/or CDC activities. SCID mice kept NK and complement functions and are able to develop ADCC and CDC responses and were selected as positive control. NOD/SCID mice have neither NK function nor the ability to stimulate complement activity and were unable to develop neither ADCC nor CDC activities. SCID/bg mice have no NK function and were unable to develop ADCC activity. In this experiment, the efficacy of sFGFR2-Fc molecule line was assessed on A549 tumor subcutaneously implanted in three different mouse strains. sFGFR2-Fc was injected subcutaneously twice a week at the dose of 5 mg/kg during the entire study course.

Experimental Design

A549 was subcutaneously implanted in SCID, NOD/SCID and SCID/bg mice as previously described (see example 8). The treatments have been administered twice a week by subcutaneously injections for 6 consecutive weeks. During the study course, the body weight and the tumor volume have been measured twice a week.

Results

Figures 17A, 17B:
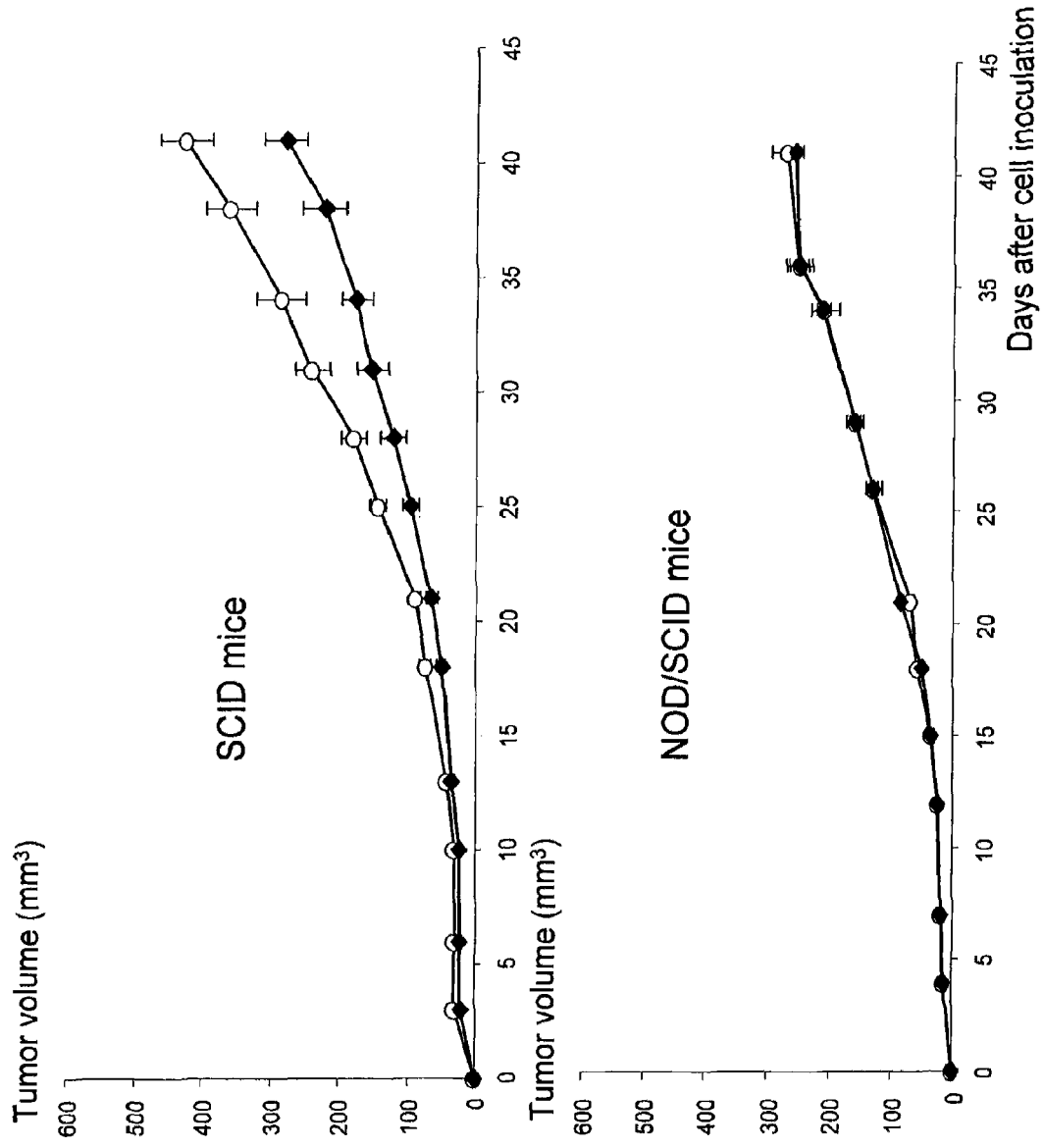
FIG. 17 shows graphs of the A549 tumor volume analysis when implanted in three mouse strains, i.e. SCID (FIG. 17A), NOD/SCID (FIG. 17B), and SCID/bg (FIG. 17C), up to day 41 (sFGFR2-Fc 100 µg/mouse/admin: diamonds; PBS control: open circles).
Figure 17C:
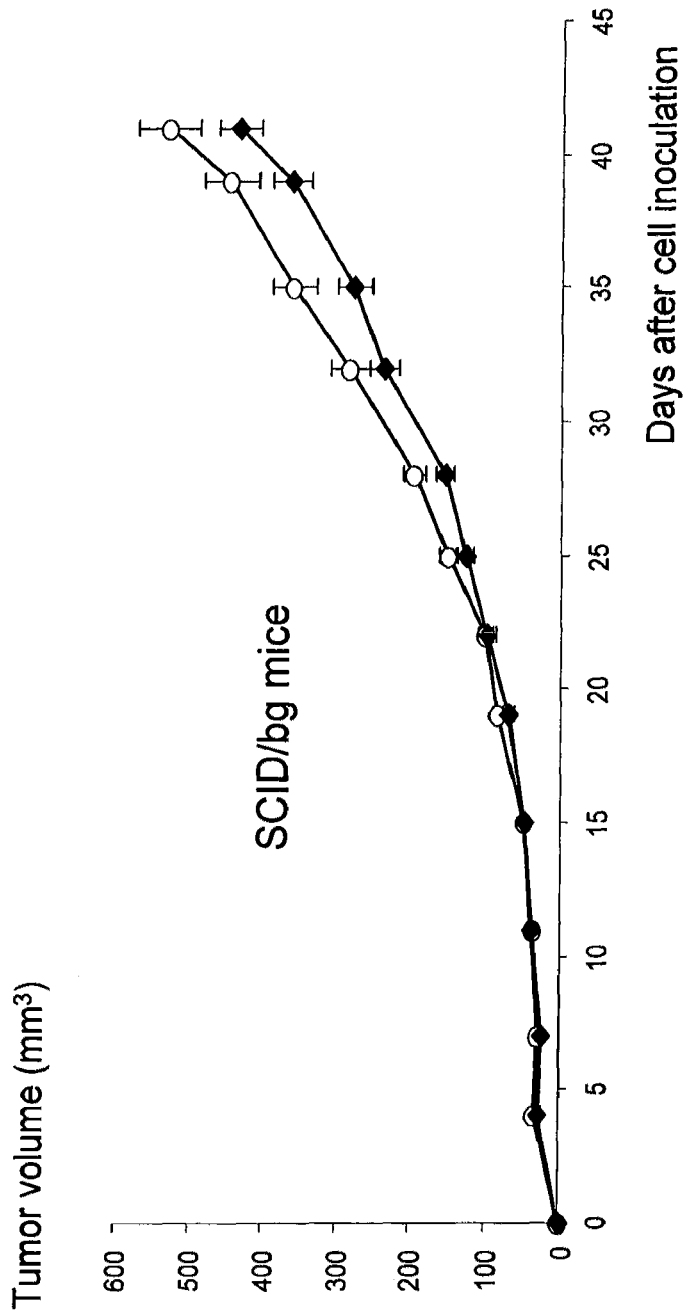

As shown in FIG. 17, the volume of the tumor was analyzed up to day 41 in the 3 experiments. In SCID mice, the group treated by sFGFR2-Fc at 5 mg/kg (diamonds) was statistically different from group control (open circles) and showed a tumor inhibition (calculated as 100−(Treated group volume/Control group volume×100)) of 39%. In the NOD/SCID mice, sFGFR2-Fc at 5 mg/kg exhibited no activity. In the SCID/bg mice, sFGFR2-Fc at 5 mg/kg recovered partially its activity (tumor inhibition=18%). According to these results, CDC and ADCC mechanisms were involved in sFGFR2-Fc efficacy.

Example 12

Evaluation of In Vivo ADCC and CDC Activities of sFGFR2-Fc Fusion Protein in H460 Subcutaneous Tumor Model In this example sFGFR2-Fc is the fusion protein corresponding to amino acid sequence SEQ ID No. 2 with an average number of sialic acid per sFGFR2 N-glycan greater than 1.6.

H460 Subcutaneous Tumor Model

H460 cell line has been identified as a tumor cell line to assess the efficacy of sFGFR2-Fc, these cells expressed high level of FGF2 in vivo and were sensitive to in vitro sFGFR2-Fc mediated-ADCC.

Mouse Strains

As previously described in example 11, three mouse strains with different immune functions (SCID, NOD/SCID and SCID/bg mice) were selected to evaluate the capacity of sFGFR2-Fc to mediate in vivo ADCC and/or CDC activities in H460. In this experiment, the efficacy of sFGFR2-Fc molecule was assessed on H460 tumor subcutaneously implanted in the three different mouse strains. sFGFR2-Fc was injected subcutaneously twice a week at the dose of 25 mg/kg during the entire study course.

Experimental Design

H460 was subcutaneously implanted in SCID, NOD/SCID and SCID/bg mice as previously described (see example 9). The treatments have been administered twice a week by subcutaneously injections for 3 consecutive weeks. During the study course, the body weight and the tumor volume have been measured twice a week.

Results

Figure 18A:
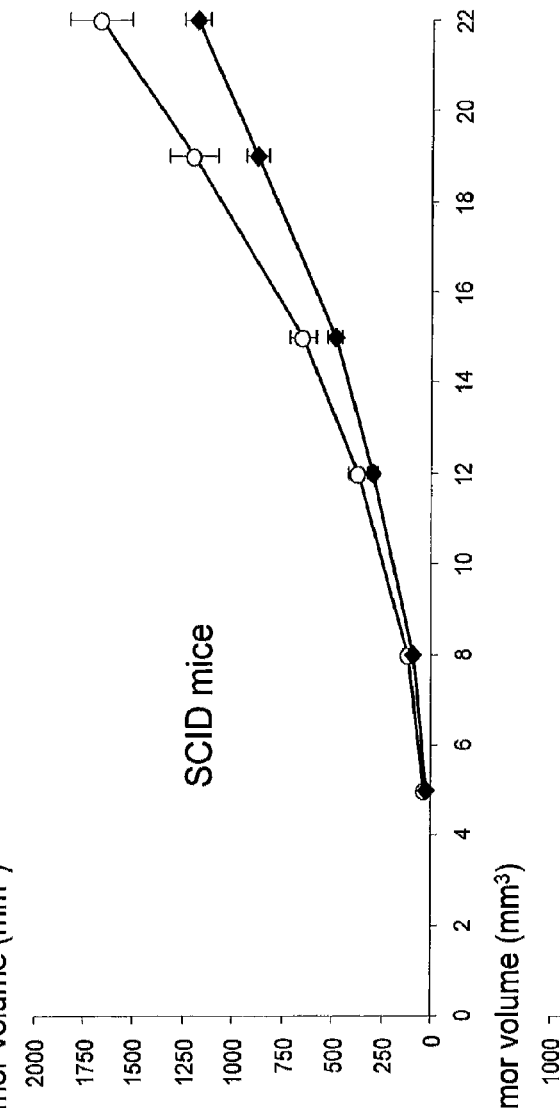
FIG. 18 shows graphs of the H460 tumor volume analysis when implanted in three mouse strains, i.e. SCID (FIG. 18A), NOD/SCID (FIG. 18B), and SCID/bg (FIG. 18C), up to day 22 (sFGFR2-Fc 100 µg/mouse/admin: diamonds; PBS control: open circles).
Figure 18B:
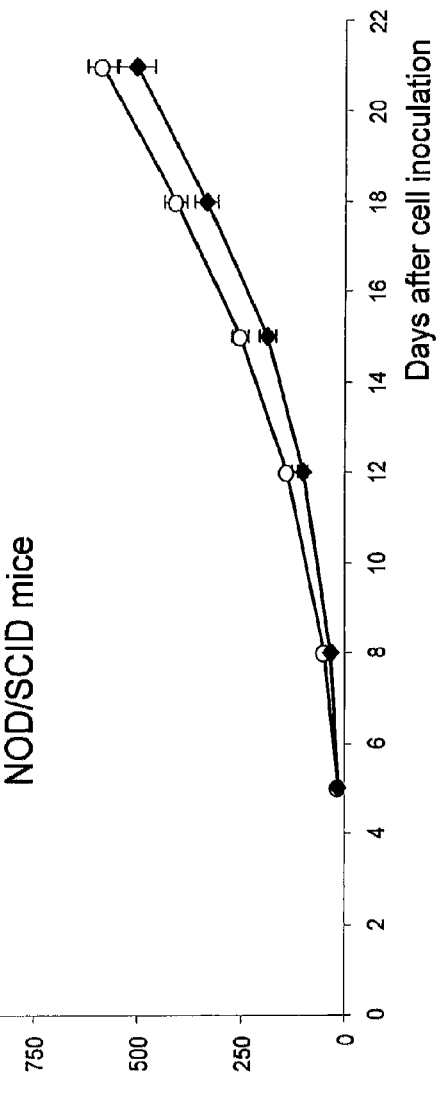
Figure 18C:
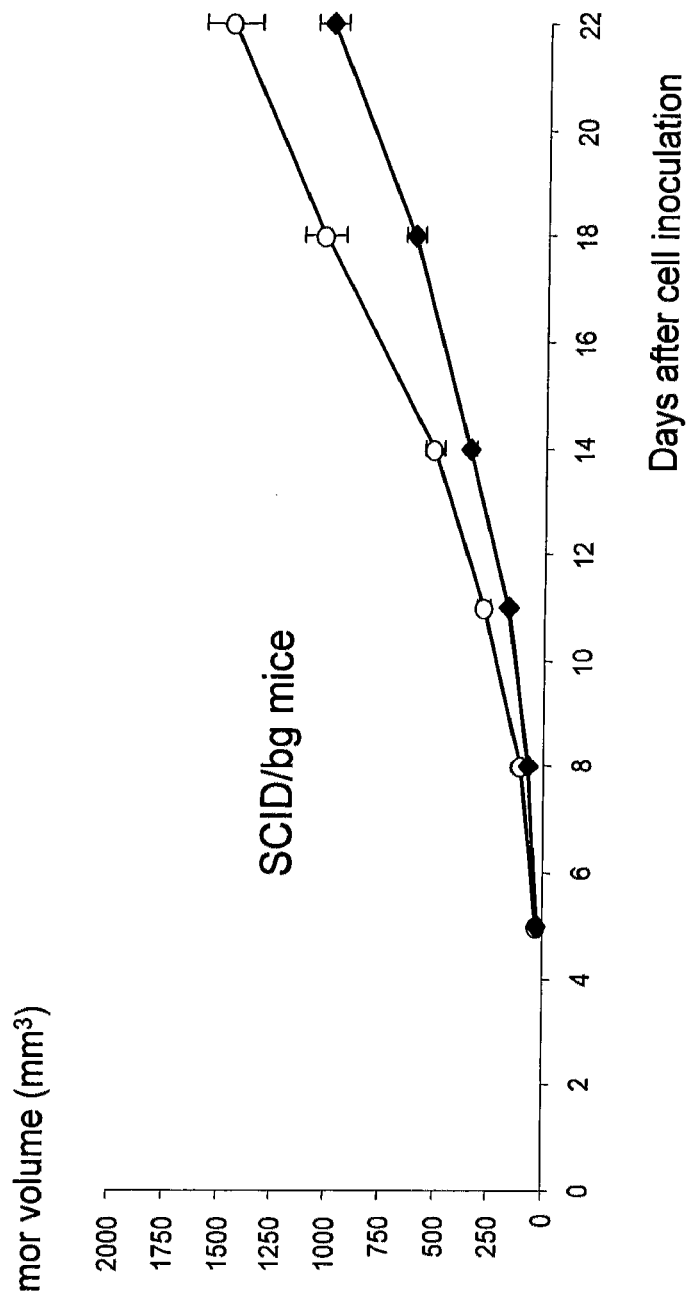

As shown in FIG. 18, the volume of the tumor was analyzed up to day 22 in the 3 experiments. In SCID mice, the group treated with sFGFR2-Fc at 25 mg/kg (diamonds) was statistically different from group control (open circles) and showed a tumor inhibition of 29%. In the NOD/SCID mice, sFGFR2-Fc at 5 mg/kg exhibited a lost of activity with a tumor inhibition of 14%. In the SCID/bg mice, sFGFR2-Fc at 5 mg/kg recovered all its activity (tumor inhibition=32%). In these studies, as observed in the A549 tumor model (see example 11), CDC and ADCC mechanisms were involved in sFGFR2-Fc efficacy.

Example 13

Evaluation of In Vivo Efficacy of sFGFR2-Fc Compared to sFGFR2-Fc (A265 Fc) in H460 Subcutaneous Tumor Model Shields at al. described a point mutation Asp265Ala in the Fc domain of human IgG1 named (A265 Fc) that conferred reduced binding to all FcγR receptors and very low antibody-dependent cell cytotoxicity (2001 J. Biol. Chem. 276:6591). This point mutation was introduced into the Fc domain of sFGFR2-Fc coding DNA sequence of plasmid pXL4547 (FIG. 19), resulting in the polynucleotide sequence represented by SEQ ID No. 13. Stable CHO/DHFR clones expressing sFGFR2-Fc (A265 Fc) (SEQ ID NO. 14) were generated using the DHFR selection and amplification system with the appropriate mammalian expression plasmids pXL4547 and plasmid pXL4417 as described in Example 3. The protein sFGFR2-Fc (A265 Fc) was then produced and purified for in vivo studies. It was verified that its glycan content was similar to the glycan content found for sFGFR2-Fc produced in Examples 3 or 5.

| Expressed protein from stable CHO-DHFR | sFGFR2-Fc (A265 Fc) |
|---|---|
| % sFGFR2-Fc sialylated species: | |
| 1-non sialylated | 40% |
| 2-Monosialylated | 28% |
| 3-Disialylated | 22% |
| 4-trisialylated | 10% |
| Monosaccharide composition of sFGFR2-Fc N-glycans per 3 mannoses | |
| 1-Glucosamine (number per 3 mannoses) | 4.35 |
| 2-Galactose (number per 3 mannoses) | 2.74 |
| 3-Fucose (number per 3 mannoses) | 0.89 |

460 Subcutaneous Tumor Model

H460 cell line has been identified as a tumor cell line to assess the efficacy of sFGFR2-Fc; these cells expressed high level of FGF2 in vivo and were sensitive to in vitro sFGFR2-Fc-mediated-ADCC.

In this experiment, the efficacy of sFGFR2-Fc molecule and the modified sFGFR2-Fc (A265 Fc) molecule was assessed on H460 tumor subcutaneously implanted in nude mice.

Experimental Design

H460 was subcutaneously implanted in nude Balb/C mice as previously described (see example 9). The treatments have been administered twice a week during the entire study course. During the study course, the body weight and the tumor volume have been measured twice a week.

Results

Figure 20:
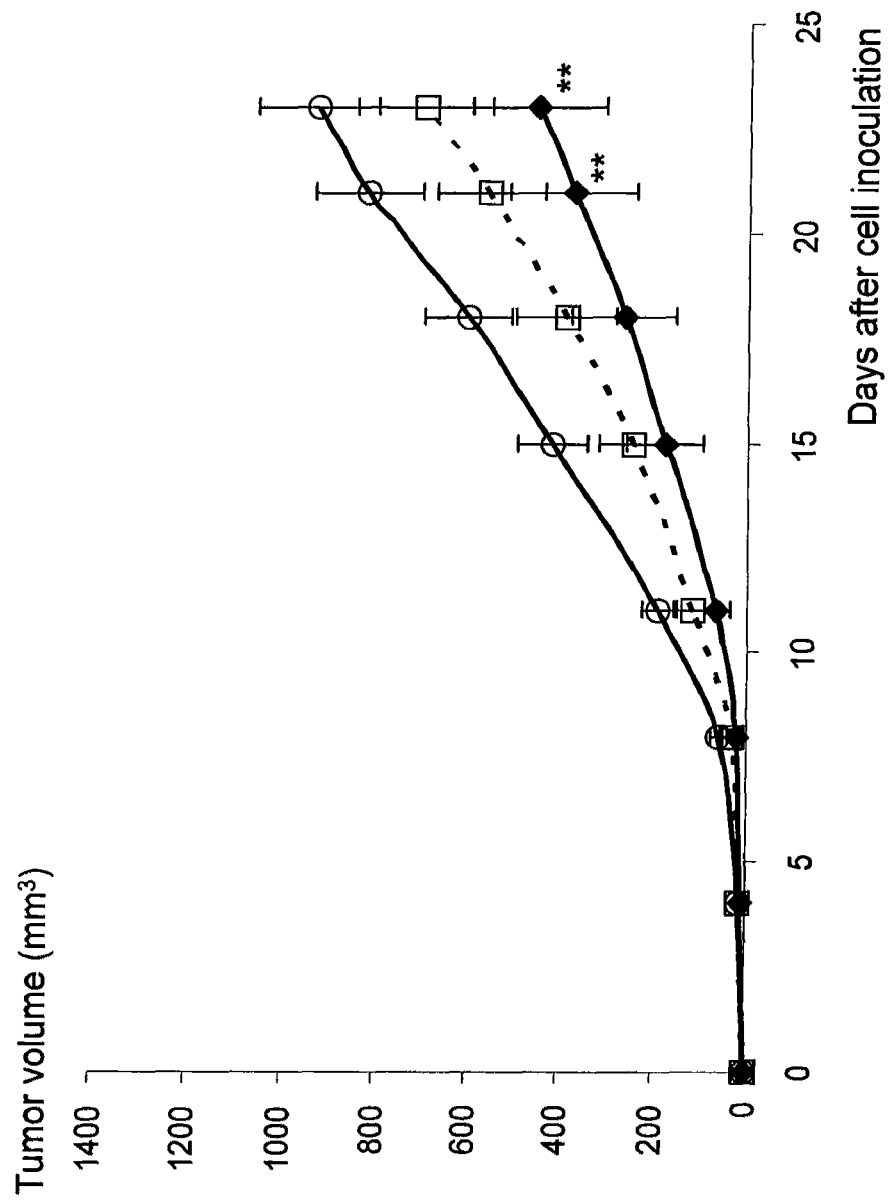
FIG. 20 is a graph showing the H460 tumor volume analysis when implanted in nude mouse strains up to day 23 (open circles: PBS control; diamonds: sFGFR2-Fc 500 µg/mouse/admin; open square: sFGFR2-Fc (A265Fc) 500 µg/mouse/admin). **: $p<0.01$ vs control Anova & Newman-Keuls post test)

As shown in FIG. 20, the volume of the tumor was analyzed up to day 23. The group treated by sFGFR2-Fc at 25 mg/kg (diamonds) was statistically different from the control group (open circles) and showed a tumor inhibition of 50%. The modified sFGFR2-Fc (A265 Fc) at 25 mg/kg exhibited a lost of activity with only a tumor inhibition of 25% (NS). The mutation within the Fc of sFGFR2-Fc (A265 Fc) induced a decrease of the activity.

Since this modification was shown to decrease antibody-dependent cell cytotoxicity, example 13 provides an indirect evidence that sFGFR2-Fc acted in vivo by a mechanism involving ADCC.

The invention claimed is:

1. A method for treating cancer overexpressing fibroblast growth factor 2 (FGF2) comprising administering to a subject with said cancer a therapeutically effective amount of a modified soluble FGF receptor Fc fusion comprising a fusion of a soluble FGF receptor 2 (sFGFR2) moiety with an Fc region of an immunoglobulin, wherein at least the $5^{th}$ N-glycosylation site of the FGFreeceptor moeity is occupied, and at most 45% of the N-glycans of the FGF receptor moiety have no sialyl group, wherein the FGF receptor Fc fusion binds FGF, and wherein the FGF receptor Fc fusion exhibits reduced aggregation or improved productivity relative to a soluble FGF receptor Fc fusion lacking the N-glycan at the 5th N-glycosylation site from the N-terminus.

2. The method of claim 1, further comprising administering an additional therapeutic agent.

3. The method of claim 2, wherein the additional therapeutic agent is an anti-angiogenic agent or a chemotherapeutic agent.

4. The method of claim 3, wherein the anti-angiogenic agent is tumor necrosis factor, an antagonist of an acidic or basic fibroblast growth factor (FGF), hepatocyte growth factor (HGF), tissue factor (TF), protein C, protein S, platelet-derived growth factor (PDGF), or HER2 receptor.

5. The method of claim 3, wherein the chemotherapeutic agent is selected from the group consisting of: anti-microtubule agents; platinum coordination complexes; alkylating agents; antibiotic agents; topoisomerase II inhibitors; antimetabolites; topoisomerase I inhibitors; hormones and hormone analogues; signal transduction pathway inhibitors; non-receptor tyrosine kinase angiogenesis inhibitors; immunotherapeutic agents; pro-apoptotic agents; and cell cycle signaling inhibitors.

6. The method of claim 3, wherein the chemotherapeutic agent is selected from the group consisting of: taxol and taxotere.

7. The method of claim 1, wherein the cancer is selected from the group consisting of: carcinoma, bladder cancer, breast cancer, colon cancer, cancer of the head and neck, kidney cancer, renal cell carcinoma, liver cancer, lung cancer, cancer of the ovary, cancer of the pancreas, stomach cancer, cancer of the cervix, thyroid cancer, skin cancer, squamous cell carcinoma, hematopoietic tumors of lymphoid lineage, leukemia, acute lymphocytic leukemia, acute lymphoblastic leukemia, B-cell lymphoma, T-cell lymphoma, Burkitt's lymphoma, hematopoietic tumors of myeloid lineage, acute and chronic myelogenous leukemias, promyelocytic leukemia, tumors of mesenchymal origin, fibrosarcoma, rhabdomyoscarcoma, melanoma, seminoma, tetratocarcinoma, neuroblastoma, glioma, tumors of the central and peripheral nervous system, astrocytoma, neuroblastoma, glioma, schwannomas, tumors of mesenchymal origin, fibrosarcoma, rhabdomyoscarama, osteosarcoma, melanoma, xeroderma pigmentosum, keratoactanthoma, seminoma, thyroid follicular cancer, and teratocarcinoma.

8. The method of claim 1, wherein the cancer is selected from the group consisting of: melanoma, leukemia, renal cancer, colon cancer, ovarian cancer, prostate cancer, lung cancer, bladder cancer, breast cancer, and head and neck cancer.

9. The method of claim 1, wherein, in addition, the $3^{rd}$, $4^{th}$, $6^{th}$, and $7^{th}$ N-glycosylation sites of the FGF receptor moiety are occupied with a N-glycan.

10. The method of claim 9, wherein at least 7 N-glycosylation sites of the FGF receptor moiety are occupied with a N-glycan.

11. The method of claim 10, wherein all N-glycosylation sites of the FGF receptor moiety are occupied with a N-glycan.

12. The method of claim 1, wherein the average number of sialic acid per N-glycan of the FGF receptor moiety is 0.9 or above.

13. The method of claim 12, wherein the average number of sialic acid per N-glycan of the FGF receptor moiety is 1.2 or above.

14. The method of claim 1, wherein the $K_D$ value of the fusion for FGF2 measured by Biacore™ is comprised between 1 and 5 nM.

15. The method of claim 14, wherein the $K_D$ value of the fusion for FGF2 measured by Biacore™ is around 1.5 nM.

16. The method of claim 1, wherein the fusion possesses ADCC and/or CDC activities.

17. The method of claim 1, wherein the N-glycans of the fusion are 60-100% fucosylated.

18. The method of claim 1, wherein the modified soluble FGF receptor Fc fusion comprises 3 mannose residues, a mean of 1.5 to 3.0 galactose residues, a mean of 3.5 to 5 of N-acetylglucosamine residues, and a mean of 0.6 to 1 fucose residues per molecule of glycan.

19. The method of claim 1, wherein the N-glycans of the fusion are 0-60% fucosylated.

20. The method of claim 1, wherein the FGF receptor is FGF receptor 2 isotype IIIc.

21. The method of claim 1, wherein the FGF receptor soluble domain has a sequence as set forth in SEQ ID NO: 4, or a sequence having an identity of at least 95% with SEQ ID NO: 4.

22. The method of claim 1, wherein the Fc portion has a sequence as set forth in SEQ ID NO: 6, or a sequence having an identity of at least 95% with the SEQ ID NO: 6.

23. The method of claim 1, wherein the modified soluble FGF receptor Fc fusion further comprises a linker sequence of at least 3 amino acid residues.

24. The method of claim 23, wherein the linker sequence is SAL (Ser-Ala-Leu).

25. The method of claim 1, wherein the modified soluble FGF receptor Fc fusion has a polypeptide sequence as set forth in SEQ ID NO: 2, or a sequence having an identity of at least 95% with the SEQ ID NO: 2.

26. The method of claim 1, wherein the modified soluble FGF receptor Fc fusion further comprises the signal peptide of SEQ ID NO: 8.

* * * * *

SEQUENCE LISTING

```
<160> NUMBER OF SEQ ID NOS: 14

<210> SEQ ID NO 1
<211> LENGTH: 1755
<212> TYPE: DNA
<213> ORGANISM: Homo sapiens
<220> FEATURE:
<221> NAME/KEY: CDS
<222> LOCATION: (1)..(1755)

<400> SEQUENCE: 1 tta gtt gag gat acc aca tta gag cca gaa gag cca cca act aaa tac     48
Leu Val Glu Asp Thr Thr Leu Glu Pro Glu Glu Pro Pro Thr Lys Tyr
1               5                   10                  15 caa atc tct caa cca gaa gtg tac gtg gct gca cca ggg gag tcg cta     96
Gln Ile Ser Gln Pro Glu Val Tyr Val Ala Ala Pro Gly Glu Ser Leu
            20                  25                  30 gag gtg cgc tgc ctg ttg aaa gat gcc gcc gtg atc agt tgg act aag    144
Glu Val Arg Cys Leu Leu Lys Asp Ala Ala Val Ile Ser Trp Thr Lys
        35                  40                  45 gat ggg gtg cac ttg ggg ccc aac aat agg aca gtg ctt att ggg gag    192
Asp Gly Val His Leu Gly Pro Asn Asn Arg Thr Val Leu Ile Gly Glu
    50                  55                  60 tac ttg cag ata aag ggc gcc acg cct aga gac tcc ggc ctc tat gct    240
Tyr Leu Gln Ile Lys Gly Ala Thr Pro Arg Asp Ser Gly Leu Tyr Ala
65                  70                  75                  80 tgt act gcc agt agg act gta gac agt gaa act tgg tac ttc atg gtg    288
Cys Thr Ala Ser Arg Thr Val Asp Ser Glu Thr Trp Tyr Phe Met Val
                85                  90                  95 aat gtc aca gat gcc atc tca tcc gga gat gat gag gat gac acc gat    336
Asn Val Thr Asp Ala Ile Ser Ser Gly Asp Asp Glu Asp Asp Thr Asp
            100                 105                 110 ggt gcg gaa gat ttt gtc agt gag aac agt aac aag aga gca cca        384
Gly Ala Glu Asp Phe Val Ser Glu Asn Ser Asn Asn Lys Arg Ala Pro
        115                 120                 125 tac tgg acc aac aca gaa aag atg gaa aag cgg ctc cat gct gtg cct    432
Tyr Trp Thr Asn Thr Glu Lys Met Glu Lys Arg Leu His Ala Val Pro
    130                 135                 140 gcg gcc aac act gtc aag ttt cgc tgc cca gcc ggg ggg aac cca atg    480
Ala Ala Asn Thr Val Lys Phe Arg Cys Pro Ala Gly Gly Asn Pro Met
145                 150                 155                 160 cca acc atg cgg tgg ctg aaa aac ggg aag gag ttt aag cag gag cat    528
Pro Thr Met Arg Trp Leu Lys Asn Gly Lys Glu Phe Lys Gln Glu His
                165                 170                 175 cgc att gga ggc tac aag gta cga aac cag cac tgg agc ctc att atg    576
Arg Ile Gly Gly Tyr Lys Val Arg Asn Gln His Trp Ser Leu Ile Met
            180                 185                 190 gaa agt gtg gtc cca tct gac aag gga aat tat acc tgt gtg gtg gag    624
Glu Ser Val Val Pro Ser Asp Lys Gly Asn Tyr Thr Cys Val Val Glu
        195                 200                 205 aat gaa tac ggg tcc atc aat cac acg tac cac ctg gat gtt gtg gag    672
Asn Glu Tyr Gly Ser Ile Asn His Thr Tyr His Leu Asp Val Val Glu
```

-continued

```
              210                 215                 220
cga tcg cct cac cgg ccc atc ctc caa gcc gga ctg ccg gca aat gcc    720
Arg Ser Pro His Arg Pro Ile Leu Gln Ala Gly Leu Pro Ala Asn Ala
225                 230                 235                 240 tcc aca gtg gtc gga gga gac gta gag ttt gtc tgc aag gtt tac agt    768
Ser Thr Val Val Gly Gly Asp Val Glu Phe Val Cys Lys Val Tyr Ser
                245                 250                 255 gat gcc cag ccc cac atc cag tgg atc aag cac gtg gaa aag aac ggc    816
Asp Ala Gln Pro His Ile Gln Trp Ile Lys His Val Glu Lys Asn Gly
            260                 265                 270 agt aaa tac ggg ccc gac ggg ctg ccc tac ctc aag gtt ctc aag gcc    864
Ser Lys Tyr Gly Pro Asp Gly Leu Pro Tyr Leu Lys Val Leu Lys Ala
        275                 280                 285 gcc ggt gtt aac acc acg gac aaa gag att gag gtt ctc tat att cgg    912
Ala Gly Val Asn Thr Thr Asp Lys Glu Ile Glu Val Leu Tyr Ile Arg
290                 295                 300 aat gta act ttt gag gac gct ggg gaa tat acg tgc ttg gcg ggt aat    960
Asn Val Thr Phe Glu Asp Ala Gly Glu Tyr Thr Cys Leu Ala Gly Asn
305                 310                 315                 320 tct att ggg ata tcc ttt cac tct gca tgg ttg aca gtt ctg cca gcg    1008
Ser Ile Gly Ile Ser Phe His Ser Ala Trp Leu Thr Val Leu Pro Ala
                325                 330                 335 cct gga aga gaa aag gag att aca gct tcc cca gac tac ctg tca gcg    1056
Pro Gly Arg Glu Lys Glu Ile Thr Ala Ser Pro Asp Tyr Leu Ser Ala
            340                 345                 350 cta gag ccc aaa tct tgt gac aaa act cac aca tgc cca ccg tgc cca    1104
Leu Glu Pro Lys Ser Cys Asp Lys Thr His Thr Cys Pro Pro Cys Pro
        355                 360                 365 gca cct gaa ctc ctg ggg gga ccg tca gtc ttc ctc ttc ccc cca aaa    1152
Ala Pro Glu Leu Leu Gly Gly Pro Ser Val Phe Leu Phe Pro Pro Lys
370                 375                 380 ccc aag gac acc ctc atg atc tcc cgg acc cct gag gtc aca tgc gtg    1200
Pro Lys Asp Thr Leu Met Ile Ser Arg Thr Pro Glu Val Thr Cys Val
385                 390                 395                 400 gtg gtg gac gtg agc cac gaa gac cct gag gtc aag ttc aac tgg tac    1248
Val Val Asp Val Ser His Glu Asp Pro Glu Val Lys Phe Asn Trp Tyr
                405                 410                 415 gtg gac ggc gtg gag gtg cat aat gcc aag aca aag ccg cgg gag gag    1296
Val Asp Gly Val Glu Val His Asn Ala Lys Thr Lys Pro Arg Glu Glu
            420                 425                 430 cag tac aac agc acg tac cgt gtg gtc agc gtc ctc acc gtc ctg cac    1344
Gln Tyr Asn Ser Thr Tyr Arg Val Val Ser Val Leu Thr Val Leu His
        435                 440                 445 cag gac tgg ctg aat ggc aag gag tac aag tgc aag gtc tcc aac aaa    1392
Gln Asp Trp Leu Asn Gly Lys Glu Tyr Lys Cys Lys Val Ser Asn Lys
450                 455                 460 gcc ctc cca gcc ccc atc gag aaa acc atc tcc aaa gcc aaa ggg cag    1440
Ala Leu Pro Ala Pro Ile Glu Lys Thr Ile Ser Lys Ala Lys Gly Gln
465                 470                 475                 480 ccc cga gaa cca cag gtg tac acc ctg ccc cca tcc cgg gat gag ctg    1488
Pro Arg Glu Pro Gln Val Tyr Thr Leu Pro Pro Ser Arg Asp Glu Leu
                485                 490                 495 acc aag aac cag gtc agc ctg acc tgc ctg gtc aaa ggc ttc tat ccc    1536
Thr Lys Asn Gln Val Ser Leu Thr Cys Leu Val Lys Gly Phe Tyr Pro
            500                 505                 510 agc gac atc gcc gtg gag tgg gag agc aat ggg cag ccg gag aac aac    1584
Ser Asp Ile Ala Val Glu Trp Glu Ser Asn Gly Gln Pro Glu Asn Asn
        515                 520                 525 tac aag acc acg cct ccc gtg ctg gac tcc gac ggc tcc ttc ttc ctc    1632
Tyr Lys Thr Thr Pro Pro Val Leu Asp Ser Asp Gly Ser Phe Phe Leu
```

```
                          530                  535                  540
tac agc aag ctc acc gtg gac aag agc agg tgg cag cag ggg aac gtc      1680
Tyr Ser Lys Leu Thr Val Asp Lys Ser Arg Trp Gln Gln Gly Asn Val
545                 550                  555                  560 ttc tca tgc tcc gtg atg cat gag gct ctg cac aac cac tac acg cag      1728
Phe Ser Cys Ser Val Met His Glu Ala Leu His Asn His Tyr Thr Gln
                565                  570                  575 aag agc ctc tcc ctg tct ccg ggt tga                                  1755
Lys Ser Leu Ser Leu Ser Pro Gly
            580

<210> SEQ ID NO 2
<211> LENGTH: 584
<212> TYPE: PRT
<213> ORGANISM: Homo sapiens

<400> SEQUENCE: 2

Leu Val Glu Asp Thr Thr Leu Glu Pro Glu Pro Pro Thr Lys Tyr
1               5                   10                  15

Gln Ile Ser Gln Pro Glu Val Tyr Val Ala Ala Pro Gly Glu Ser Leu
            20                  25                  30

Glu Val Arg Cys Leu Leu Lys Asp Ala Ala Val Ile Ser Trp Thr Lys
        35                  40                  45

Asp Gly Val His Leu Gly Pro Asn Asn Arg Thr Val Leu Ile Gly Glu
    50                  55                  60

Tyr Leu Gln Ile Lys Gly Ala Thr Pro Arg Asp Ser Gly Leu Tyr Ala
65                  70                  75                  80

Cys Thr Ala Ser Arg Thr Val Asp Ser Glu Thr Trp Tyr Phe Met Val
                85                  90                  95

Asn Val Thr Asp Ala Ile Ser Ser Gly Asp Asp Glu Asp Asp Thr Asp
            100                 105                 110

Gly Ala Glu Asp Phe Val Ser Glu Asn Ser Asn Asn Lys Arg Ala Pro
        115                 120                 125

Tyr Trp Thr Asn Thr Glu Lys Met Glu Lys Arg Leu His Ala Val Pro
    130                 135                 140

Ala Ala Asn Thr Val Lys Phe Arg Cys Pro Ala Gly Gly Asn Pro Met
145                 150                 155                 160

Pro Thr Met Arg Trp Leu Lys Asn Gly Lys Glu Phe Lys Gln Glu His
                165                 170                 175

Arg Ile Gly Gly Tyr Lys Val Arg Asn Gln His Trp Ser Leu Ile Met
            180                 185                 190

Glu Ser Val Val Pro Ser Asp Lys Gly Asn Tyr Thr Cys Val Val Glu
        195                 200                 205

Asn Glu Tyr Gly Ser Ile Asn His Thr Tyr His Leu Asp Val Val Glu
    210                 215                 220

Arg Ser Pro His Arg Pro Ile Leu Gln Ala Gly Leu Pro Ala Asn Ala
225                 230                 235                 240

Ser Thr Val Val Gly Gly Asp Val Glu Phe Val Cys Lys Val Tyr Ser
                245                 250                 255

Asp Ala Gln Pro His Ile Gln Trp Ile Lys His Val Glu Lys Asn Gly
            260                 265                 270

Ser Lys Tyr Gly Pro Asp Gly Leu Pro Tyr Leu Lys Val Leu Lys Ala
        275                 280                 285

Ala Gly Val Asn Thr Thr Asp Lys Glu Ile Glu Val Leu Tyr Ile Arg
    290                 295                 300

Asn Val Thr Phe Glu Asp Ala Gly Glu Tyr Thr Cys Leu Ala Gly Asn
```

```
                    305                 310                 315                 320
Ser Ile Gly Ile Ser Phe His Ser Ala Trp Leu Thr Val Leu Pro Ala
                325                 330                 335

Pro Gly Arg Glu Lys Glu Ile Thr Ala Ser Pro Asp Tyr Leu Ser Ala
            340                 345                 350

Leu Glu Pro Lys Ser Cys Asp Lys Thr His Thr Cys Pro Pro Cys Pro
        355                 360                 365

Ala Pro Glu Leu Leu Gly Gly Pro Ser Val Phe Leu Phe Pro Pro Lys
    370                 375                 380

Pro Lys Asp Thr Leu Met Ile Ser Arg Thr Pro Glu Val Thr Cys Val
385                 390                 395                 400

Val Val Asp Val Ser His Glu Asp Pro Glu Val Lys Phe Asn Trp Tyr
                405                 410                 415

Val Asp Gly Val Glu Val His Asn Ala Lys Thr Lys Pro Arg Glu Glu
            420                 425                 430

Gln Tyr Asn Ser Thr Tyr Arg Val Val Ser Val Leu Thr Val Leu His
        435                 440                 445

Gln Asp Trp Leu Asn Gly Lys Glu Tyr Lys Cys Lys Val Ser Asn Lys
    450                 455                 460

Ala Leu Pro Ala Pro Ile Glu Lys Thr Ile Ser Lys Ala Lys Gly Gln
465                 470                 475                 480

Pro Arg Glu Pro Gln Val Tyr Thr Leu Pro Pro Ser Arg Asp Glu Leu
                485                 490                 495

Thr Lys Asn Gln Val Ser Leu Thr Cys Leu Val Lys Gly Phe Tyr Pro
            500                 505                 510

Ser Asp Ile Ala Val Glu Trp Glu Ser Asn Gly Gln Pro Glu Asn Asn
        515                 520                 525

Tyr Lys Thr Thr Pro Pro Val Leu Asp Ser Asp Gly Ser Phe Phe Leu
    530                 535                 540

Tyr Ser Lys Leu Thr Val Asp Lys Ser Arg Trp Gln Gln Gly Asn Val
545                 550                 555                 560

Phe Ser Cys Ser Val Met His Glu Ala Leu His Asn His Tyr Thr Gln
                565                 570                 575

Lys Ser Leu Ser Leu Ser Pro Gly
            580

<210> SEQ ID NO 3
<211> LENGTH: 1050
<212> TYPE: DNA
<213> ORGANISM: Homo sapiens
<220> FEATURE:
<221> NAME/KEY: CDS
<222> LOCATION: (1)..(1050)

<400> SEQUENCE: 3 tta gtt gag gat acc aca tta gag cca gaa gag cca cca act aaa tac       48
Leu Val Glu Asp Thr Thr Leu Glu Pro Glu Glu Pro Pro Thr Lys Tyr
1               5                   10                  15 caa atc tct caa cca gaa gtg tac gtg gct gca cca ggg gag tcg cta       96
Gln Ile Ser Gln Pro Glu Val Tyr Val Ala Ala Pro Gly Glu Ser Leu
                20                  25                  30 gag gtg cgc tgc ctg ttg aaa gat gcc gcc gtg atc agt tgg act aag      144
Glu Val Arg Cys Leu Leu Lys Asp Ala Ala Val Ile Ser Trp Thr Lys
            35                  40                  45 gat ggg gtg cac ttg ggg ccc aac aat agg aca gtg ctt att ggg gag      192
Asp Gly Val His Leu Gly Pro Asn Asn Arg Thr Val Leu Ile Gly Glu
        50                  55                  60
```

```
tac ttg cag ata aag ggc gcc acg cct aga gac tcc ggc ctc tat gct       240
Tyr Leu Gln Ile Lys Gly Ala Thr Pro Arg Asp Ser Gly Leu Tyr Ala
 65                  70                  75                  80 tgt act gcc agt agg act gta gac agt gaa act tgg tac ttc atg gtg       288
Cys Thr Ala Ser Arg Thr Val Asp Ser Glu Thr Trp Tyr Phe Met Val
                 85                  90                  95 aat gtc aca gat gcc atc tca tcc gga gat gat gag gat gac acc gat       336
Asn Val Thr Asp Ala Ile Ser Ser Gly Asp Asp Glu Asp Asp Thr Asp
            100                 105                 110 ggt gcg gaa gat ttt gtc agt gag aac agt aac aac aag aga gca cca       384
Gly Ala Glu Asp Phe Val Ser Glu Asn Ser Asn Asn Lys Arg Ala Pro
        115                 120                 125 tac tgg acc aac aca gaa aag atg gaa aag cgg ctc cat gct gtg cct       432
Tyr Trp Thr Asn Thr Glu Lys Met Glu Lys Arg Leu His Ala Val Pro
130                 135                 140 gcg gcc aac act gtc aag ttt cgc tgc cca gcc ggg ggg aac cca atg       480
Ala Ala Asn Thr Val Lys Phe Arg Cys Pro Ala Gly Gly Asn Pro Met
145                 150                 155                 160 cca acc atg cgg tgg ctg aaa aac ggg aag gag ttt aag cag gag cat       528
Pro Thr Met Arg Trp Leu Lys Asn Gly Lys Glu Phe Lys Gln Glu His
                165                 170                 175 cgc att gga ggc tac aag gta cga aac cag cac tgg agc ctc att atg       576
Arg Ile Gly Gly Tyr Lys Val Arg Asn Gln His Trp Ser Leu Ile Met
            180                 185                 190 gaa agt gtg gtc cca tct gac aag gga aat tat acc tgt gtg gtg gag       624
Glu Ser Val Val Pro Ser Asp Lys Gly Asn Tyr Thr Cys Val Val Glu
        195                 200                 205 aat gaa tac ggg tcc atc aat cac acg tac cac ctg gat gtt gtg gag       672
Asn Glu Tyr Gly Ser Ile Asn His Thr Tyr His Leu Asp Val Val Glu
210                 215                 220 cga tcg cct cac cgg ccc atc ctc caa gcc gga ctg ccg gca aat gcc       720
Arg Ser Pro His Arg Pro Ile Leu Gln Ala Gly Leu Pro Ala Asn Ala
225                 230                 235                 240 tcc aca gtg gtc gga gga gac gta gag ttt gtc tgc aag gtt tac agt       768
Ser Thr Val Val Gly Gly Asp Val Glu Phe Val Cys Lys Val Tyr Ser
                245                 250                 255 gat gcc cag ccc cac atc cag tgg atc aag cac gtg gaa aag aac ggc       816
Asp Ala Gln Pro His Ile Gln Trp Ile Lys His Val Glu Lys Asn Gly
            260                 265                 270 agt aaa tac ggg ccc gac ggg ctg ccc tac ctc aag gtt ctc aag gcc       864
Ser Lys Tyr Gly Pro Asp Gly Leu Pro Tyr Leu Lys Val Leu Lys Ala
        275                 280                 285 gcc ggt gtt aac acc acg gac aaa gag att gag gtt ctc tat att cgg       912
Ala Gly Val Asn Thr Thr Asp Lys Glu Ile Glu Val Leu Tyr Ile Arg
290                 295                 300 aat gta act ttt gag gac gct ggg gaa tat acg tgc ttg gcg ggt aat       960
Asn Val Thr Phe Glu Asp Ala Gly Glu Tyr Thr Cys Leu Ala Gly Asn
305                 310                 315                 320 tct att ggg ata tcc ttt cac tct gca tgg ttg aca gtt ctg cca gcg      1008
Ser Ile Gly Ile Ser Phe His Ser Ala Trp Leu Thr Val Leu Pro Ala
                325                 330                 335 cct gga aga gaa aag gag att aca gct tcc cca gac tac ctg              1050
Pro Gly Arg Glu Lys Glu Ile Thr Ala Ser Pro Asp Tyr Leu
            340                 345                 350

<210> SEQ ID NO 4
<211> LENGTH: 350
<212> TYPE: PRT
<213> ORGANISM: Homo sapiens

<400> SEQUENCE: 4
```

```
Leu Val Glu Asp Thr Thr Leu Glu Pro Glu Pro Pro Thr Lys Tyr
 1               5                  10                  15

Gln Ile Ser Gln Pro Glu Val Tyr Val Ala Ala Pro Gly Glu Ser Leu
             20                  25                  30

Glu Val Arg Cys Leu Leu Lys Asp Ala Ala Val Ile Ser Trp Thr Lys
         35                  40                  45

Asp Gly Val His Leu Gly Pro Asn Asn Arg Thr Val Leu Ile Gly Glu
 50                  55                  60

Tyr Leu Gln Ile Lys Gly Ala Thr Pro Arg Asp Ser Gly Leu Tyr Ala
 65                  70                  75                  80

Cys Thr Ala Ser Arg Thr Val Asp Ser Glu Thr Trp Tyr Phe Met Val
             85                  90                  95

Asn Val Thr Asp Ala Ile Ser Ser Gly Asp Asp Glu Asp Asp Thr Asp
             100                 105                 110

Gly Ala Glu Asp Phe Val Ser Glu Asn Ser Asn Asn Lys Arg Ala Pro
         115                 120                 125

Tyr Trp Thr Asn Thr Glu Lys Met Glu Lys Arg Leu His Ala Val Pro
 130                 135                 140

Ala Ala Asn Thr Val Lys Phe Arg Cys Pro Ala Gly Gly Asn Pro Met
 145                 150                 155                 160

Pro Thr Met Arg Trp Leu Lys Asn Gly Lys Glu Phe Lys Gln Glu His
             165                 170                 175

Arg Ile Gly Gly Tyr Lys Val Arg Asn Gln His Trp Ser Leu Ile Met
             180                 185                 190

Glu Ser Val Val Pro Ser Asp Lys Gly Asn Tyr Thr Cys Val Val Glu
         195                 200                 205

Asn Glu Tyr Gly Ser Ile Asn His Thr Tyr His Leu Asp Val Val Glu
 210                 215                 220

Arg Ser Pro His Arg Pro Ile Leu Gln Ala Gly Leu Pro Ala Asn Ala
 225                 230                 235                 240

Ser Thr Val Val Gly Gly Asp Val Glu Phe Val Cys Lys Val Tyr Ser
             245                 250                 255

Asp Ala Gln Pro His Ile Gln Trp Ile Lys His Val Glu Lys Asn Gly
         260                 265                 270

Ser Lys Tyr Gly Pro Asp Gly Leu Pro Tyr Leu Lys Val Leu Lys Ala
 275                 280                 285

Ala Gly Val Asn Thr Thr Asp Lys Glu Ile Glu Val Leu Tyr Ile Arg
 290                 295                 300

Asn Val Thr Phe Glu Asp Ala Gly Glu Tyr Thr Cys Leu Ala Gly Asn
 305                 310                 315                 320

Ser Ile Gly Ile Ser Phe His Ser Ala Trp Leu Thr Val Leu Pro Ala
             325                 330                 335

Pro Gly Arg Glu Lys Glu Ile Thr Ala Ser Pro Asp Tyr Leu
         340                 345                 350

<210> SEQ ID NO 5
<211> LENGTH: 696
<212> TYPE: DNA
<213> ORGANISM: Homo sapiens
<220> FEATURE:
<221> NAME/KEY: CDS
<222> LOCATION: (1)..(696)

<400> SEQUENCE: 5 gag ccc aaa tct tgt gac aaa act cac aca tgc cca ccg tgc cca gca    48
Glu Pro Lys Ser Cys Asp Lys Thr His Thr Cys Pro Pro Cys Pro Ala
 1               5                  10                  15
```

```
cct gaa ctc ctg ggg gga ccg tca gtc ttc ctc ttc ccc cca aaa ccc    96
Pro Glu Leu Leu Gly Gly Pro Ser Val Phe Leu Phe Pro Pro Lys Pro
         20                  25                  30 aag gac acc ctc atg atc tcc cgg acc cct gag gtc aca tgc gtg gtg   144
Lys Asp Thr Leu Met Ile Ser Arg Thr Pro Glu Val Thr Cys Val Val
             35                  40                  45 gtg gac gtg agc cac gaa gac cct gag gtc aag ttc aac tgg tac gtg   192
Val Asp Val Ser His Glu Asp Pro Glu Val Lys Phe Asn Trp Tyr Val
 50                  55                  60 gac ggc gtg gag gtg cat aat gcc aag aca aag ccg cgg gag gag cag   240
Asp Gly Val Glu Val His Asn Ala Lys Thr Lys Pro Arg Glu Glu Gln
 65                  70                  75                  80 tac aac agc acg tac cgt gtg gtc agc gtc ctc acc gtc ctg cac cag   288
Tyr Asn Ser Thr Tyr Arg Val Val Ser Val Leu Thr Val Leu His Gln
                 85                  90                  95 gac tgg ctg aat ggc aag gag tac aag tgc aag gtc tcc aac aaa gcc   336
Asp Trp Leu Asn Gly Lys Glu Tyr Lys Cys Lys Val Ser Asn Lys Ala
            100                 105                 110 ctc cca gcc ccc atc gag aaa acc atc tcc aaa gcc aaa ggg cag ccc   384
Leu Pro Ala Pro Ile Glu Lys Thr Ile Ser Lys Ala Lys Gly Gln Pro
        115                 120                 125 cga gaa cca cag gtg tac acc ctg ccc cca tcc cgg gat gag ctg acc   432
Arg Glu Pro Gln Val Tyr Thr Leu Pro Pro Ser Arg Asp Glu Leu Thr
    130                 135                 140 aag aac cag gtc agc ctg acc tgc ctg gtc aaa ggc ttc tat ccc agc   480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac   528
Asp Ile Ala Val Glu Trp Glu Ser Asn Gly Gln Pro Glu Asn Asn Tyr
                165                 170                 175 aag acc acg cct ccc gtg ctg gac tcc gac ggc tcc ttc ttc ctc tac   576
Lys Thr Thr Pro Pro Val Leu Asp Ser Asp Gly Ser Phe Phe Leu Tyr
            180                 185                 190 agc aag ctc acc gtg gac aag agc agg tgg cag cag ggg aac gtc ttc   624
Ser Lys Leu Thr Val Asp Lys Ser Arg Trp Gln Gln Gly Asn Val Phe
        195                 200                 205 tca tgc tcc gtg atg cat gag gct ctg cac aac cac tac acg cag aag   672
Ser Cys Ser Val Met His Glu Ala Leu His Asn His Tyr Thr Gln Lys
    210                 215                 220 agc ctc tcc ctg tct ccg ggt tga                                   696
Ser Leu Ser Leu Ser Pro Gly
225                 230

<210> SEQ ID NO 6
<211> LENGTH: 231
<212> TYPE: PRT
<213> ORGANISM: Homo sapiens

<400> SEQUENCE: 6

Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80
```

-continued

```
Tyr Asn Ser Thr Tyr Arg Val Val Ser Val Leu Thr Val Leu His Gln
             85                  90                  95

Asp Trp Leu Asn Gly Lys Glu Tyr Lys Cys Lys Val Ser Asn Lys Ala
        100                 105                 110

Leu Pro Ala Pro Ile Glu Lys Thr Ile Ser Lys Ala Lys Gly Gln Pro
    115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 7
<211> LENGTH: 60
<212> TYPE: DNA
<213> ORGANISM: Homo sapiens
<220> FEATURE:
<221> NAME/KEY: CDS
<222> LOCATION: (1)..(60)

<400> SEQUENCE: 7 atg tac agg atg caa ctc ctg tct tgc att gca cta agt ctt gca ctt        48
Met Tyr Arg Met Gln Leu Leu Ser Cys Ile Ala Leu Ser Leu Ala Leu
1               5                   10                  15 gtc acg aat tca                                                         60
Val Thr Asn Ser
            20

<210> SEQ ID NO 8
<211> LENGTH: 20
<212> TYPE: PRT
<213> ORGANISM: Homo sapiens

<400> SEQUENCE: 8

Met Tyr Arg Met Gln Leu Leu Ser Cys Ile Ala Leu Ser Leu Ala Leu
1               5                   10                  15

Val Thr Asn Ser
            20

<210> SEQ ID NO 9
<211> LENGTH: 1197
<212> TYPE: DNA
<213> ORGANISM: Homo sapiens
<220> FEATURE:
<221> NAME/KEY: CDS
<222> LOCATION: (1)..(1197)

<400> SEQUENCE: 9 atg agg ctt cgg gag ccg ctc ctg agc ggc agc gcc gcg atg cca ggc        48
Met Arg Leu Arg Glu Pro Leu Leu Ser Gly Ser Ala Ala Met Pro Gly
1               5                   10                  15 gcg tcc cta cag cgg gcc tgc cgc ctg ctc gtg gcc gtc tgc gct ctg        96
Ala Ser Leu Gln Arg Ala Cys Arg Leu Leu Val Ala Val Cys Ala Leu
```

-continued

|  |  |  |  |  |  |  |  |  |  |  |  |  |  |  |  |
|---|---|---|---|---|---|---|---|---|---|---|---|---|---|---|---|
|  |  | 20 |  |  |  | 25 |  |  |  | 30 |  |  |  |  |  |

```
cac ctt ggc gtc acc ctc gtt tac tac ctg gct ggc cgc gac ctg agc      144
His Leu Gly Val Thr Leu Val Tyr Tyr Leu Ala Gly Arg Asp Leu Ser
         35                  40                  45 cgc ctg ccc caa ctg gtc gga gtc tcc aca ccg ctg cag ggc ggc tcg      192
Arg Leu Pro Gln Leu Val Gly Val Ser Thr Pro Leu Gln Gly Gly Ser
 50                  55                  60 aac agt gcc gcc gcc atc ggg cag tcc tcc ggg gag ctc cgg acc gga      240
Asn Ser Ala Ala Ala Ile Gly Gln Ser Ser Gly Glu Leu Arg Thr Gly
 65                  70                  75                  80 ggg gcc cgg ccg ccg cct cct cta ggc gcc tcc tcc cag ccg cgc ccg      288
Gly Ala Arg Pro Pro Pro Pro Leu Gly Ala Ser Ser Gln Pro Arg Pro
                 85                  90                  95 ggt ggc gac tcc agc cca gtc gtg gat tct ggc cct ggc ccc gct agc      336
Gly Gly Asp Ser Ser Pro Val Val Asp Ser Gly Pro Gly Pro Ala Ser
                100                 105                 110 aac ttg acc tcg gtc cca gtg ccc cac acc acc gca ctg tcg ctg ccc      384
Asn Leu Thr Ser Val Pro Val Pro His Thr Thr Ala Leu Ser Leu Pro
                115                 120                 125 gcc tgc cct gag gag tcc ccg ctg ctt gtg ggc ccc atg ctg att gag      432
Ala Cys Pro Glu Glu Ser Pro Leu Leu Val Gly Pro Met Leu Ile Glu
130                 135                 140 ttt aac atg cct gtg gac ctg gag ctc gtg gca aag cag aac cca aat      480
Phe Asn Met Pro Val Asp Leu Glu Leu Val Ala Lys Gln Asn Pro Asn
145                 150                 155                 160 gtg aag atg ggc ggc cgc tat gcc ccc agg gac tgc gtc tct cct cac      528
Val Lys Met Gly Gly Arg Tyr Ala Pro Arg Asp Cys Val Ser Pro His
                165                 170                 175 aag gtg gcc atc atc att cca ttc cgc aac cgg cag gag cac ctc aag      576
Lys Val Ala Ile Ile Ile Pro Phe Arg Asn Arg Gln Glu His Leu Lys
                180                 185                 190 tac tgg cta tat tat ttg cat cca gtc ctg cag cgc cag cag ctg gac      624
Tyr Trp Leu Tyr Tyr Leu His Pro Val Leu Gln Arg Gln Gln Leu Asp
                195                 200                 205 tat ggc atc tat gtt atc aac cag gcg gga gac act ata ttc aat cgt      672
Tyr Gly Ile Tyr Val Ile Asn Gln Ala Gly Asp Thr Ile Phe Asn Arg
                210                 215                 220 gct aag ctc ctc aat gtt ggc ttt caa gaa gcc ttg aag gac tat gac      720
Ala Lys Leu Leu Asn Val Gly Phe Gln Glu Ala Leu Lys Asp Tyr Asp
225                 230                 235                 240 tac acc tgc ttt gtg ttt agt gac gtg gac ctc att cca atg aat gac      768
Tyr Thr Cys Phe Val Phe Ser Asp Val Asp Leu Ile Pro Met Asn Asp
                245                 250                 255 cat aat gcg tac agg tgt ttt tca cag cca cgg cac att tcc gtt gca      816
His Asn Ala Tyr Arg Cys Phe Ser Gln Pro Arg His Ile Ser Val Ala
                260                 265                 270 atg gat aag ttt gga ttc agc cta cct tat gtt cag tat ttt gga ggt      864
Met Asp Lys Phe Gly Phe Ser Leu Pro Tyr Val Gln Tyr Phe Gly Gly
                275                 280                 285 gtc tct gct cta agt aaa caa cag ttt cta acc atc aat gga ttt cct      912
Val Ser Ala Leu Ser Lys Gln Gln Phe Leu Thr Ile Asn Gly Phe Pro
290                 295                 300 aat aat tat tgg ggc tgg gga gga gaa gat gat gac att ttt aac aga      960
Asn Asn Tyr Trp Gly Trp Gly Gly Glu Asp Asp Asp Ile Phe Asn Arg
305                 310                 315                 320 tta gtt ttt aga ggc atg tct ata tct cgc cca aat gct gtg gtc ggg     1008
Leu Val Phe Arg Gly Met Ser Ile Ser Arg Pro Asn Ala Val Val Gly
                325                 330                 335 agg tgt cgc atg atc cgc cac tca aga gac aag aaa aat gaa ccc aat     1056
Arg Cys Arg Met Ile Arg His Ser Arg Asp Lys Lys Asn Glu Pro Asn
```

```
                        340                 345                 350
cct cag agg ttt gac cga att gca cac aca aag gag aca atg ctc tct      1104
Pro Gln Arg Phe Asp Arg Ile Ala His Thr Lys Glu Thr Met Leu Ser
        355                 360                 365 gat ggt ttg aac tca ctc acc tac cag gtg ctg gat gta cag aga tac      1152
Asp Gly Leu Asn Ser Leu Thr Tyr Gln Val Leu Asp Val Gln Arg Tyr
370                 375                 380 cca ttg tat acc caa atc aca gtg gac atc ggg aca ccg agc tag          1197
Pro Leu Tyr Thr Gln Ile Thr Val Asp Ile Gly Thr Pro Ser
385                 390                 395
```

<210> SEQ ID NO 10
<211> LENGTH: 398
<212> TYPE: PRT
<213> ORGANISM: Homo sapiens

<400> SEQUENCE: 10

```
Met Arg Leu Arg Glu Pro Leu Ser Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Ser
        35                  40                  45

Arg Leu Pro Gln Leu Val Gly Val Ser Thr Pro Leu Gln Gly Gly Ser
50                  55                  60

Asn Ser Ala Ala Ala Ile Gly Gln Ser Ser Gly Glu Leu Arg Thr Gly
65                  70                  75                  80

Gly Ala Arg Pro Pro Pro Leu Gly Ala Ser Ser Gln Pro Arg Pro
                85                  90                  95

Gly Gly Asp Ser Ser Pro Val Val Asp Ser Gly Pro Gly Pro Ala Ser
            100                 105                 110

Asn Leu Thr Ser Val Pro Val Pro His Thr Thr Ala Leu Ser Leu Pro
        115                 120                 125

Ala Cys Pro Glu Glu Ser Pro Leu Leu Val Gly Pro Met Leu Ile Glu
    130                 135                 140

Phe Asn Met Pro Val Asp Leu Glu Leu Val Ala Lys Gln Asn Pro Asn
145                 150                 155                 160

Val Lys Met Gly Gly Arg Tyr Ala Pro Arg Asp Cys Val Ser Pro His
                165                 170                 175

Lys Val Ala Ile Ile Ile Pro Phe Arg Asn Arg Gln Glu His Leu Lys
            180                 185                 190

Tyr Trp Leu Tyr Tyr Leu His Pro Val Leu Gln Arg Gln Gln Leu Asp
        195                 200                 205

Tyr Gly Ile Tyr Val Ile Asn Gln Ala Gly Asp Thr Ile Phe Asn Arg
    210                 215                 220

Ala Lys Leu Leu Asn Val Gly Phe Gln Glu Ala Leu Lys Asp Tyr Asp
225                 230                 235                 240

Tyr Thr Cys Phe Val Phe Ser Asp Val Asp Leu Ile Pro Met Asn Asp
                245                 250                 255

His Asn Ala Tyr Arg Cys Phe Ser Gln Pro Arg His Ile Ser Val Ala
            260                 265                 270

Met Asp Lys Phe Gly Phe Ser Leu Pro Tyr Val Gln Tyr Phe Gly Gly
        275                 280                 285

Val Ser Ala Leu Ser Lys Gln Gln Phe Leu Thr Ile Asn Gly Phe Pro
    290                 295                 300

Asn Asn Tyr Trp Gly Trp Gly Gly Glu Asp Asp Asp Ile Phe Asn Arg
```

-continued

```
                305                 310                 315                 320
Leu Val Phe Arg Gly Met Ser Ile Ser Arg Pro Asn Ala Val Val Gly
                        325                 330                 335

Arg Cys Arg Met Ile Arg His Ser Arg Asp Lys Lys Asn Glu Pro Asn
                    340                 345                 350

Pro Gln Arg Phe Asp Arg Ile Ala His Thr Lys Glu Thr Met Leu Ser
                355                 360                 365

Asp Gly Leu Asn Ser Leu Thr Tyr Gln Val Leu Asp Val Gln Arg Tyr
            370                 375                 380

Pro Leu Tyr Thr Gln Ile Thr Val Asp Ile Gly Thr Pro Ser
385                 390                 395

<210> SEQ ID NO 11
<211> LENGTH: 1128
<212> TYPE: DNA
<213> ORGANISM: Homo sapiens
<220> FEATURE:
<221> NAME/KEY: CDS
<222> LOCATION: (1)..(1128)

<400> SEQUENCE: 11 atg gga ctc ttg gta ttt gtg cgc aat ctg ctg cta gcc ctc tgc ctc      48
Met Gly Leu Leu Val Phe Val Arg Asn Leu Leu Leu Ala Leu Cys Leu
1               5                   10                  15 ttt ctg gta ctg gga ttt ttg tat tat tct gcg tgg aag cta cac tta      96
Phe Leu Val Leu Gly Phe Leu Tyr Tyr Ser Ala Trp Lys Leu His Leu
            20                  25                  30 ctc cag tgg gag gag gac tcc aat tca gtg gtt ctt tcc ttt gac tcc     144
Leu Gln Trp Glu Glu Asp Ser Asn Ser Val Val Leu Ser Phe Asp Ser
        35                  40                  45 gct gga caa aca cta ggc tca gag tat gat cgg ttg ggc ttc ctc ctg     192
Ala Gly Gln Thr Leu Gly Ser Glu Tyr Asp Arg Leu Gly Phe Leu Leu
    50                  55                  60 aat ctg gac tct aaa ctg cct gct gaa tta gcc acc aag tac gca aac     240
Asn Leu Asp Ser Lys Leu Pro Ala Glu Leu Ala Thr Lys Tyr Ala Asn
65                  70                  75                  80 ttt tca gag gga gct tgc aag cct ggc tat gct tca gcc ttg atg acg     288
Phe Ser Glu Gly Ala Cys Lys Pro Gly Tyr Ala Ser Ala Leu Met Thr
                85                  90                  95 gcc atc ttc ccc cgg ttc tcc aag cca gca ccc atg ttc ctg gat gac     336
Ala Ile Phe Pro Arg Phe Ser Lys Pro Ala Pro Met Phe Leu Asp Asp
            100                 105                 110 tcc ttt cgc aag tgg gct aga atc cgg gag ttc gtg ccg cct ttt ggg     384
Ser Phe Arg Lys Trp Ala Arg Ile Arg Glu Phe Val Pro Pro Phe Gly
        115                 120                 125 atc aaa ggt caa gac aat ctg atc aaa gcc atc ttg tca gtc acc aaa     432
Ile Lys Gly Gln Asp Asn Leu Ile Lys Ala Ile Leu Ser Val Thr Lys
    130                 135                 140 gag tac cgc ctg acc cct gcc ttg gac agc ctc cgc tgc cgc gcc tgc     480
Glu Tyr Arg Leu Thr Pro Ala Leu Asp Ser Leu Arg Cys Arg Arg Cys
145                 150                 155                 160 atc atc gtg ggc aat gga ggc gtt ctt gcc aac aag tct ctg ggg tca     528
Ile Ile Val Gly Asn Gly Gly Val Leu Ala Asn Lys Ser Leu Gly Ser
                165                 170                 175 cga att gac gac tat gac att gtg gtg aga ctg aat tca gca cca gtg     576
Arg Ile Asp Asp Tyr Asp Ile Val Val Arg Leu Asn Ser Ala Pro Val
            180                 185                 190 aaa ggc ttt gag aag gac gtg ggc agc aaa acg aca ctg cgc atc acc     624
Lys Gly Phe Glu Lys Asp Val Gly Ser Lys Thr Thr Leu Arg Ile Thr
        195                 200                 205
```

| | | | | | | | | | | | | | | | | |
|---|---|---|---|---|---|---|---|---|---|---|---|---|---|---|---|---|
| tac | ccc | gag | ggc | gcc | atg | cag | cgg | cct | gag | cag | tac | gag | cgc | gat | tct | 672 |
| Tyr | Pro | Glu | Gly | Ala | Met | Gln | Arg | Pro | Glu | Gln | Tyr | Glu | Arg | Asp | Ser | |
| | 210 | | | | 215 | | | | | 220 | | | | | | |
| ctc | ttt | gtc | ctc | gcc | ggc | ttc | aag | tgg | cag | gac | ttt | aag | tgg | ttg | aaa | 720 |
| Leu | Phe | Val | Leu | Ala | Gly | Phe | Lys | Trp | Gln | Asp | Phe | Lys | Trp | Leu | Lys | |
| 225 | | | | | 230 | | | | | 235 | | | | | 240 | |
| tac | atc | gtc | tac | aag | gag | aga | gtg | agt | gca | tcg | gat | ggc | ttc | tgg | aaa | 768 |
| Tyr | Ile | Val | Tyr | Lys | Glu | Arg | Val | Ser | Ala | Ser | Asp | Gly | Phe | Trp | Lys | |
| | | | | 245 | | | | | 250 | | | | | 255 | | |
| tct | gtg | gcc | act | cga | gtg | ccc | aag | gag | ccc | cct | gag | att | cga | atc | ctc | 816 |
| Ser | Val | Ala | Thr | Arg | Val | Pro | Lys | Glu | Pro | Pro | Glu | Ile | Arg | Ile | Leu | |
| | | | 260 | | | | | 265 | | | | | 270 | | | |
| aac | cca | tat | ttc | atc | cag | gag | gcc | gcc | ttc | acc | ctc | att | ggc | ctg | ccc | 864 |
| Asn | Pro | Tyr | Phe | Ile | Gln | Glu | Ala | Ala | Phe | Thr | Leu | Ile | Gly | Leu | Pro | |
| | | 275 | | | | | 280 | | | | | 285 | | | | |
| ttc | aac | aat | ggc | ctc | atg | ggc | cgg | ggg | aac | atc | cct | acc | ctt | ggc | agt | 912 |
| Phe | Asn | Asn | Gly | Leu | Met | Gly | Arg | Gly | Asn | Ile | Pro | Thr | Leu | Gly | Ser | |
| | 290 | | | | 295 | | | | | 300 | | | | | | |
| gtg | gca | gtg | acc | atg | gca | cta | cac | ggc | tgt | gac | gag | gtg | gca | gtc | gca | 960 |
| Val | Ala | Val | Thr | Met | Ala | Leu | His | Gly | Cys | Asp | Glu | Val | Ala | Val | Ala | |
| 305 | | | | | 310 | | | | | 315 | | | | | 320 | |
| gga | ttt | ggc | tat | gac | atg | agc | aca | ccc | aac | gca | ccc | ctg | cac | tac | tat | 1008 |
| Gly | Phe | Gly | Tyr | Asp | Met | Ser | Thr | Pro | Asn | Ala | Pro | Leu | His | Tyr | Tyr | |
| | | | | 325 | | | | | 330 | | | | | 335 | | |
| gag | acc | gtt | cgc | atg | gca | gcc | atc | aaa | gag | tcc | tgg | acg | cac | aat | atc | 1056 |
| Glu | Thr | Val | Arg | Met | Ala | Ala | Ile | Lys | Glu | Ser | Trp | Thr | His | Asn | Ile | |
| | | | 340 | | | | | 345 | | | | | 350 | | | |
| cag | cga | gag | aaa | gag | ttt | ctg | cgg | aag | ctg | gtg | aaa | gct | cgc | gtc | atc | 1104 |
| Gln | Arg | Glu | Lys | Glu | Phe | Leu | Arg | Lys | Leu | Val | Lys | Ala | Arg | Val | Ile | |
| | | 355 | | | | | 360 | | | | | 365 | | | | |
| act | gat | cta | agc | agt | ggc | atc | tga | | | | | | | | | 1128 |
| Thr | Asp | Leu | Ser | Ser | Gly | Ile | | | | | | | | | | |
| | 370 | | | | 375 | | | | | | | | | | | |

<210> SEQ ID NO 12
<211> LENGTH: 375
<212> TYPE: PRT
<213> ORGANISM: Homo sapiens

<400> SEQUENCE: 12

Met Gly Leu Leu Val Phe Val Arg Asn Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Glu Asp Ser Asn Ser Val Val Leu Ser Phe Asp Ser
        35                  40                  45

Ala Gly Gln Thr Leu Gly Ser Glu Tyr Asp Arg Leu Gly Phe Leu Leu
    50                  55                  60

Asn Leu Asp Ser Lys Leu Pro Ala Glu Leu Ala Thr Lys Tyr Ala Asn
65                  70                  75                  80

Phe Ser Glu Gly Ala Cys Lys Pro Gly Tyr Ala Ser Ala Leu Met Thr
                85                  90                  95

Ala Ile Phe Pro Arg Phe Ser Lys Pro Ala Pro Met Phe Leu Asp Asp
            100                 105                 110

Ser Phe Arg Lys Trp Ala Arg Ile Arg Glu Phe Val Pro Pro Phe Gly
        115                 120                 125

Ile Lys Gly Gln Asp Asn Leu Ile Lys Ala Ile Leu Ser Val Thr Lys
    130                 135                 140

Glu Tyr Arg Leu Thr Pro Ala Leu Asp Ser Leu Arg Cys Arg Arg Cys

```
                145                 150                 155                 160
        Ile Ile Val Gly Asn Gly Gly Val Leu Ala Asn Lys Ser Leu Gly Ser
                        165                 170                 175

Arg Ile Asp Asp Tyr Asp Ile Val Val Arg Leu Asn Ser Ala Pro Val
                    180                 185                 190

Lys Gly Phe Glu Lys Asp Val Gly Ser Lys Thr Thr Leu Arg Ile Thr
                195                 200                 205

Tyr Pro Glu Gly Ala Met Gln Arg Pro Glu Gln Tyr Glu Arg Asp Ser
            210                 215                 220

Leu Phe Val Leu Ala Gly Phe Lys Trp Gln Asp Phe Lys Trp Leu Lys
        225                 230                 235                 240

Tyr Ile Val Tyr Lys Glu Arg Val Ser Ala Ser Asp Gly Phe Trp Lys
                        245                 250                 255

Ser Val Ala Thr Arg Val Pro Lys Glu Pro Pro Glu Ile Arg Ile Leu
                    260                 265                 270

Asn Pro Tyr Phe Ile Gln Glu Ala Ala Phe Thr Leu Ile Gly Leu Pro
                275                 280                 285

Phe Asn Asn Gly Leu Met Gly Arg Gly Asn Ile Pro Thr Leu Gly Ser
        290                 295                 300

Val Ala Val Thr Met Ala Leu His Gly Cys Asp Glu Val Ala Val Ala
        305                 310                 315                 320

Gly Phe Gly Tyr Asp Met Ser Thr Pro Asn Ala Pro Leu His Tyr Tyr
                        325                 330                 335

Glu Thr Val Arg Met Ala Ala Ile Lys Glu Ser Trp Thr His Asn Ile
                    340                 345                 350

Gln Arg Glu Lys Glu Phe Leu Arg Lys Leu Val Lys Ala Arg Val Ile
                355                 360                 365

Thr Asp Leu Ser Ser Gly Ile
            370                 375

<210> SEQ ID NO 13
<211> LENGTH: 1722
<212> TYPE: DNA
<213> ORGANISM: Homo sapiens
<220> FEATURE:
<221> NAME/KEY: CDS
<222> LOCATION: (1)..(1722)

<400> SEQUENCE: 13 tta gtt gag gat acc aca tta gag cca gaa gag cca cca act aaa tac        48
Leu Val Glu Asp Thr Thr Leu Glu Pro Glu Glu Pro Pro Thr Lys Tyr
1               5                   10                  15 caa atc tct caa cca gaa gtg tac gtg gct gca ccg ggg gag tcg cta        96
Gln Ile Ser Gln Pro Glu Val Tyr Val Ala Ala Pro Gly Glu Ser Leu
            20                  25                  30 gag gtg cgc tgc ctg ttg aaa gat gcc gcc gtg atc agt tgg act aag       144
Glu Val Arg Cys Leu Leu Lys Asp Ala Ala Val Ile Ser Trp Thr Lys
        35                  40                  45 gat ggg gtg cac ttg ggg ccc aac aat agg aca gtg ctt att ggg gag       192
Asp Gly Val His Leu Gly Pro Asn Asn Arg Thr Val Leu Ile Gly Glu
    50                  55                  60 tac ttg cag ata aag ggc gcc acg cct aga gac tcc ggc ctc tat gct       240
Tyr Leu Gln Ile Lys Gly Ala Thr Pro Arg Asp Ser Gly Leu Tyr Ala
65                  70                  75                  80 tgt act gcc agt agg act gta gac agt gaa act tgg tac ttc atg gtg       288
Cys Thr Ala Ser Arg Thr Val Asp Ser Glu Thr Trp Tyr Phe Met Val
                85                  90                  95 aat gtc aca gat gcc atc tca tcc gga gat gat gag gat gac acc gat       336
```

```
            Asn Val Thr Asp Ala Ile Ser Ser Gly Asp Asp Glu Asp Thr Asp
                            100                 105                 110 gtt gcg gaa gat ttt gtc agt gag aac agt aac aac aag aga gca cca        384
Gly Ala Glu Asp Phe Val Ser Glu Asn Ser Asn Asn Lys Arg Ala Pro
            115                 120                 125 tac tgg acc aac aca gaa aag atg gaa aag cgg ctc cat gct gtg cct        432
Tyr Trp Thr Asn Thr Glu Lys Met Glu Lys Arg Leu His Ala Val Pro
            130                 135                 140 gcg gcc aac act gtc aag ttt cgc tgc cca gcc ggg ggg aac cca atg        480
Ala Ala Asn Thr Val Lys Phe Arg Cys Pro Ala Gly Gly Asn Pro Met
145                 150                 155                 160 cca acc atg cgg tgg ctg aaa aac ggg aag gag ttt aag cag gag cat        528
Pro Thr Met Arg Trp Leu Lys Asn Gly Lys Glu Phe Lys Gln Glu His
            165                 170                 175 cgc att gga ggc tac aag gta cga aac cag cac tgg agc ctc att atg        576
Arg Ile Gly Gly Tyr Lys Val Arg Asn Gln His Trp Ser Leu Ile Met
            180                 185                 190 gaa agt gtg gtc cca tct gac aag gga aat tat acc tgt gtg gtg gag        624
Glu Ser Val Val Pro Ser Asp Lys Gly Asn Tyr Thr Cys Val Val Glu
            195                 200                 205 aat gaa tac ggg tcc atc aat cac acg tac cac ctg gat gtt gtg gag        672
Asn Glu Tyr Gly Ser Ile Asn His Thr Tyr His Leu Asp Val Val Glu
210                 215                 220 cga tcg cct cac cgg ccc atc ctc caa gcc gga ctg ccg gca aat gcc        720
Arg Ser Pro His Arg Pro Ile Leu Gln Ala Gly Leu Pro Ala Asn Ala
225                 230                 235                 240 tcc aca gtg gtc gga gga gac gta gag ttt gtc tgc aag gtt tac agt        768
Ser Thr Val Val Gly Gly Asp Val Glu Phe Val Cys Lys Val Tyr Ser
            245                 250                 255 gat gcc cag ccc cac atc cag tgg atc aag cac gtg gaa aag aac ggc        816
Asp Ala Gln Pro His Ile Gln Trp Ile Lys His Val Glu Lys Asn Gly
            260                 265                 270 agt aaa tac ggg ccc gac ggg ctg ccc tac ctc aag gtt ctc aag gcc        864
Ser Lys Tyr Gly Pro Asp Gly Leu Pro Tyr Leu Lys Val Leu Lys Ala
            275                 280                 285 gcc ggt gtt aac acc acg gac aaa gag att gag gtt ctc tat att cgg        912
Ala Gly Val Asn Thr Thr Asp Lys Glu Ile Glu Val Leu Tyr Ile Arg
            290                 295                 300 aat gta act ttt gag gac gct ggg gaa tat acg tgc ttg gcg ggt aat        960
Asn Val Thr Phe Glu Asp Ala Gly Glu Tyr Thr Cys Leu Ala Gly Asn
305                 310                 315                 320 tct att ggg ata tcc ttt cac tct gca tgg ttg aca gtt ctg cca gcg       1008
Ser Ile Gly Ile Ser Phe His Ser Ala Trp Leu Thr Val Leu Pro Ala
            325                 330                 335 cct gga aga gaa aag gag att aca gct tcc cca gac aaa act cac aca       1056
Pro Gly Arg Glu Lys Glu Ile Thr Ala Ser Pro Asp Lys Thr His Thr
            340                 345                 350 tgc cca ccg tgc cca gca cct gaa ctc ctg ggg gga ccg tca gtc ttc       1104
Cys Pro Pro Cys Pro Ala Pro Glu Leu Leu Gly Gly Pro Ser Val Phe
            355                 360                 365 ctc ttc ccc cca aaa ccc aag gac acc ctc atg atc tcc cgg acc cct       1152
Leu Phe Pro Pro Lys Pro Lys Asp Thr Leu Met Ile Ser Arg Thr Pro
370                 375                 380 gag gtc aca tgc gtg gtg gtg gcc gtg agc cac gaa gac cct gag gtc       1200
Glu Val Thr Cys Val Val Val Ala Val Ser His Glu Asp Pro Glu Val
385                 390                 395                 400 aag ttc aac tgg tac gtg gac ggc gtg gag gtg cat aat gcc aag aca       1248
Lys Phe Asn Trp Tyr Val Asp Gly Val Glu Val His Asn Ala Lys Thr
            405                 410                 415 aag ccg cgg gag gag cag tac aac agc acg tac cgt gtg gtc agc gtc       1296
```

```
                                                              -continued
Lys Pro Arg Glu Glu Gln Tyr Asn Ser Thr Tyr Arg Val Val Ser Val
            420                 425                 430 ctc acc gtc ctg cac cag gac tgg ctg aat ggc aag gag tac aag tgc     1344
Leu Thr Val Leu His Gln Asp Trp Leu Asn Gly Lys Glu Tyr Lys Cys
                435                 440                 445 aag gtc tcc aac aaa gcc ctc cca gcc ccc atc gag aaa acc atc tcc     1392
Lys Val Ser Asn Lys Ala Leu Pro Ala Pro Ile Glu Lys Thr Ile Ser
450                 455                 460 aaa gcc aaa ggg cag ccc cga gaa cca cag gtg tac acc ctg ccc cca     1440
Lys Ala Lys Gly Gln Pro Arg Glu Pro Gln Val Tyr Thr Leu Pro Pro
465                 470                 475                 480 tcc cgg gat gag ctg acc aag aac cag gtc agc ctg acc tgc ctg gtc     1488
Ser Arg Asp Glu Leu Thr Lys Asn Gln Val Ser Leu Thr Cys Leu Val
                485                 490                 495 aaa ggc ttc tat ccc agc gac atc gcc gtg gag tgg gag agc aat ggg     1536
Lys Gly Phe Tyr Pro Ser Asp Ile Ala Val Glu Trp Glu Ser Asn Gly
                500                 505                 510 cag ccg gag aac aac tac aag acc acg cct ccc gtg ctg gac tcc gac     1584
Gln Pro Glu Asn Asn Tyr Lys Thr Thr Pro Pro Val Leu Asp Ser Asp
            515                 520                 525 ggc tcc ttc ttc ctc tac agc aag ctc acc gtg gac aag agc agg tgg     1632
Gly Ser Phe Phe Leu Tyr Ser Lys Leu Thr Val Asp Lys Ser Arg Trp
530                 535                 540 cag cag ggg aac gtc ttc tca tgc tcc gtg atg cat gag gct ctg cac     1680
Gln Gln Gly Asn Val Phe Ser Cys Ser Val Met His Glu Ala Leu His
545                 550                 555                 560 aac cac tac acg cag aag agc ctc tcc ctg tct ccg ggt tga              1722
Asn His Tyr Thr Gln Lys Ser Leu Ser Leu Ser Pro Gly
                565                 570

<210> SEQ ID NO 14
<211> LENGTH: 573
<212> TYPE: PRT
<213> ORGANISM: Homo sapiens

<400> SEQUENCE: 14

Leu Val Glu Asp Thr Thr Leu Glu Pro Glu Glu Pro Pro Thr Lys Tyr
1               5                   10                  15

Gln Ile Ser Gln Pro Glu Val Tyr Val Ala Ala Pro Gly Glu Ser Leu
                20                  25                  30

Glu Val Arg Cys Leu Leu Lys Asp Ala Ala Val Ile Ser Trp Thr Lys
            35                  40                  45

Asp Gly Val His Leu Gly Pro Asn Asn Arg Thr Val Leu Ile Gly Glu
        50                  55                  60

Tyr Leu Gln Ile Lys Gly Ala Thr Pro Arg Asp Ser Gly Leu Tyr Ala
65                  70                  75                  80

Cys Thr Ala Ser Arg Thr Val Asp Ser Glu Thr Trp Tyr Phe Met Val
                85                  90                  95

Asn Val Thr Asp Ala Ile Ser Ser Gly Asp Asp Glu Asp Asp Thr Asp
                100                 105                 110

Gly Ala Glu Asp Phe Val Ser Glu Asn Ser Asn Asn Lys Arg Ala Pro
            115                 120                 125

Tyr Trp Thr Asn Thr Glu Lys Met Glu Lys Arg Leu His Ala Val Pro
        130                 135                 140

Ala Ala Asn Thr Val Lys Phe Arg Cys Pro Ala Gly Gly Asn Pro Met
145                 150                 155                 160

Pro Thr Met Arg Trp Leu Lys Asn Gly Lys Glu Phe Lys Gln Glu His
                165                 170                 175
```

-continued

```
Arg Ile Gly Gly Tyr Lys Val Arg Asn Gln His Trp Ser Leu Ile Met
            180                 185                 190

Glu Ser Val Val Pro Ser Asp Lys Gly Asn Tyr Thr Cys Val Val Glu
            195                 200                 205

Asn Glu Tyr Gly Ser Ile Asn His Thr Tyr His Leu Asp Val Val Glu
            210                 215                 220

Arg Ser Pro His Arg Pro Ile Leu Gln Ala Gly Leu Pro Ala Asn Ala
225                 230                 235                 240

Ser Thr Val Val Gly Gly Asp Val Glu Phe Val Cys Lys Val Tyr Ser
            245                 250                 255

Asp Ala Gln Pro His Ile Gln Trp Ile Lys His Val Glu Lys Asn Gly
            260                 265                 270

Ser Lys Tyr Gly Pro Asp Gly Leu Pro Tyr Leu Lys Val Leu Lys Ala
            275                 280                 285

Ala Gly Val Asn Thr Thr Asp Lys Glu Ile Glu Val Leu Tyr Ile Arg
            290                 295                 300

Asn Val Thr Phe Glu Asp Ala Gly Glu Tyr Thr Cys Leu Ala Gly Asn
305                 310                 315                 320

Ser Ile Gly Ile Ser Phe His Ser Ala Trp Leu Thr Val Leu Pro Ala
            325                 330                 335

Pro Gly Arg Glu Lys Glu Ile Thr Ala Ser Pro Asp Lys Thr His Thr
            340                 345                 350

Cys Pro Pro Cys Pro Ala Pro Glu Leu Leu Gly Gly Pro Ser Val Phe
            355                 360                 365

Leu Phe Pro Pro Lys Pro Lys Asp Thr Leu Met Ile Ser Arg Thr Pro
            370                 375                 380

Glu Val Thr Cys Val Val Val Ala Val Ser His Glu Asp Pro Glu Val
385                 390                 395                 400

Lys Phe Asn Trp Tyr Val Asp Gly Val Glu Val His Asn Ala Lys Thr
            405                 410                 415

Lys Pro Arg Glu Glu Gln Tyr Asn Ser Thr Tyr Arg Val Val Ser Val
            420                 425                 430

Leu Thr Val Leu His Gln Asp Trp Leu Asn Gly Lys Glu Tyr Lys Cys
            435                 440                 445

Lys Val Ser Asn Lys Ala Leu Pro Ala Pro Ile Glu Lys Thr Ile Ser
450                 455                 460

Lys Ala Lys Gly Gln Pro Arg Glu Pro Gln Val Tyr Thr Leu Pro Pro
465                 470                 475                 480

Ser Arg Asp Glu Leu Thr Lys Asn Gln Val Ser Leu Thr Cys Leu Val
            485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
            515                 520                 525

Gly Ser Phe Phe Leu Tyr Ser Lys Leu Thr Val Asp Lys Ser Arg Trp
            530                 535                 540

Gln Gln Gly Asn Val Phe Ser Cys Ser Val Met His Glu Ala Leu His
545                 550                 555                 560

Asn His Tyr Thr Gln Lys Ser Leu Ser Leu Ser Pro Gly
            565                 570
```